United States Patent [19]

Ruoslahti et al.

[11] Patent Number: 5,705,609
[45] Date of Patent: Jan. 6, 1998

[54] DECORIN FRAGMENTS INHIBITING CELL REGULATORY FACTORS

[75] Inventors: Erkki I. Ruoslahti, Rancho Santa Fe; Michael D. Pierschbacher, San Diego; Jose Cardenas, San Diego; William Craig, San Diego; Daniel G. Mullen, San Diego, all of Calif.

[73] Assignee: La Jolla Cancer Research Foundation, La Jolla, Calif.

[21] Appl. No.: 442,063

[22] Filed: May 16, 1995

Related U.S. Application Data

[63] Continuation of Ser. No. 865,652, Apr. 3, 1992, abandoned, which is a continuation-in-part of Ser. No. 792,192, Nov. 14, 1991, abandoned, which is a continuation-in-part of Ser. No. 467,888, Jan. 22, 1990, abandoned, which is a continuation-in-part of Ser. No. 212,702, Jun. 28, 1988, abandoned.

[51] Int. Cl.$^6$ .................. C07K 7/06; C07K 14/435; A61K 38/08; A61K 38/17
[52] U.S. Cl. .................. 530/329; 530/324; 530/399; 930/10; 514/17
[58] Field of Search .................. 530/300, 350, 530/380, 324, 325, 326, 327, 328, 329, 399; 435/71; 930/10; 514/2, 8, 12, 17

[56] References Cited

U.S. PATENT DOCUMENTS

| | | | |
|---|---|---|---|
| 5,171,674 | 12/1992 | Stevens et al. | 435/69.1 |
| 5,229,495 | 7/1993 | Ichijo et al. | 530/350 |

FOREIGN PATENT DOCUMENTS

| | | |
|---|---|---|
| WO 91/10727 | 1/1991 | WIPO . |
| PCT/US93/03171 | 4/1993 | WIPO . |

OTHER PUBLICATIONS

Krusius et al *Proc Natl Acad Sci* 83: 7683–7688 (1986).
Ruoslahti *Ann Rev Cell Biol* 4: 229–55 (1988).
Kahari et al. *J of Biol Chem* 266(16):10608–15 (1991).
Yamaguchi et al *Nature* 346: 281–284 (1990).
Krusius et al. Biochem. 83: 7683–7687, 1986.
Fisher et al. J. Biol. Chem. 264(8): 4571–4576, 1989.
Cheifetz et al. J. Biol. Chem. 263(22):10783–10789, 1988.
Cheifetz et al. J. Biol. Chem. 263(32):16984–16991, 1988.
Pearson et al. J. Biol. Chem. 258(24):15101–15104, 1983.
Fritze et al. J. Biol. Chem. 100:1041–1049, 1985.
Castellot et al. Am. J. Pathol. 125:493–500, 1986.
Castellot et al. J. Biol. Chem. 257(19):11256–11260, 1982.
Vogel et al. Biochem J. 223:587–597, 1984.
Massagué et al. J. Biol. Chem 260(5):2636–2645, 1985.
Andres et al. J. Cell Biol. 109(6): 3137–3145, 1989.
Kanzaki et al. Cell 61: 1051–1061, 1990.
Brennan et al. Can. Res. 43: 4302–4307, 1983.
Brennan et al. J. Biol. Chem 258(22): 13742–13750, 1984.
Kresse et al. Am. J. Hum. Genet. 41, 1987.
Yamaguchi et al. Nature 336: 244–246, 1983.
Patthy, L. J. Mol. Biol. 198: 567–577, 1987.
Bassols et al. J. Biol Chem. 263(6):3039–3045, 1988.
Segarini et al. J. Biol. Chem. 263(17): 8366–8370, 1988.
Cheifetz et al. Cell: 409–415, 1987.
Ishihara et al. J. Biol. Chem. 262(10): 4708–4716, 1987.
Day et al. Biochem J. 248:801–805, 1987.

*Primary Examiner*—Vasu S. Jagannathan
*Assistant Examiner*—Christine Saoud
*Attorney, Agent, or Firm*—Campbell & Flores, LLP

[57] ABSTRACT

The present invention provides a method of inhibiting an activity of a cell regulatory factor comprising contacting the cell regulatory factor with a purified polypeptide, wherein the polypeptide comprises a cell regulatory factor binding domain of a protein. The protein is characterized by a leucine-rich repeat of about 24 amino acids. In a specific embodiment, the present invention relates to the ability of decorin, a 40,000 dalton protein that usually carries a glycosaminoglycan chain, and more specifically to active fragments of decorin or its functional equivalents to bind TGFβ. The invention also provides a novel cell regulatory factor designated MRF. Also provided are methods of identifying, detecting and purifying cell regulatory factors and proteins which bind and affect the activity of cell regulatory factors.

5 Claims, 10 Drawing Sheets

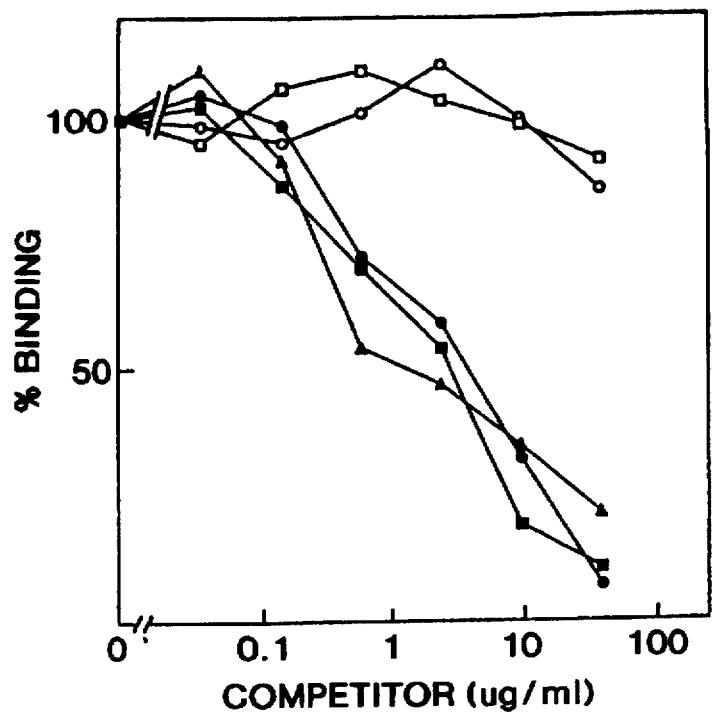
FIG. 3A
FIG. 3B
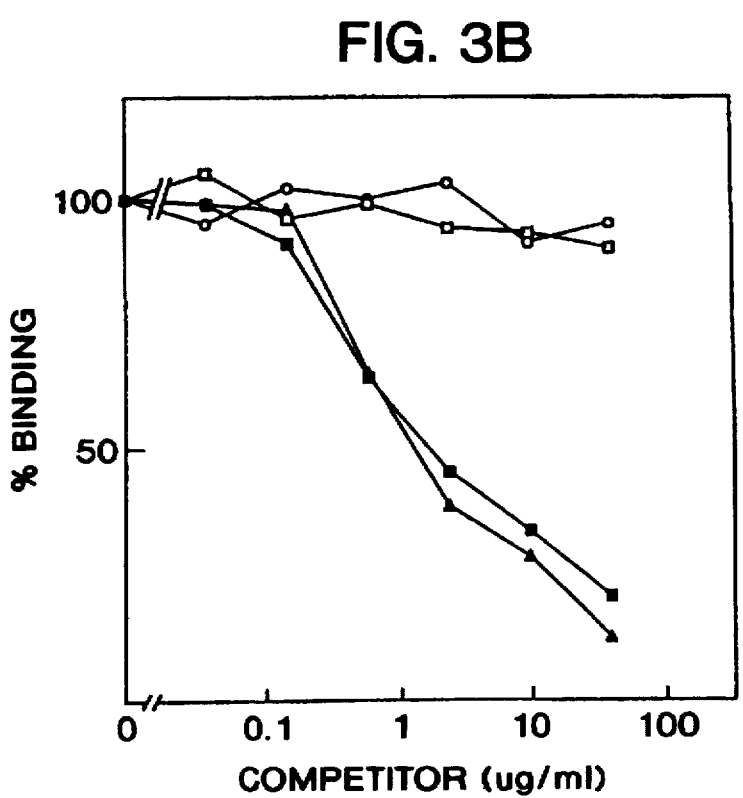

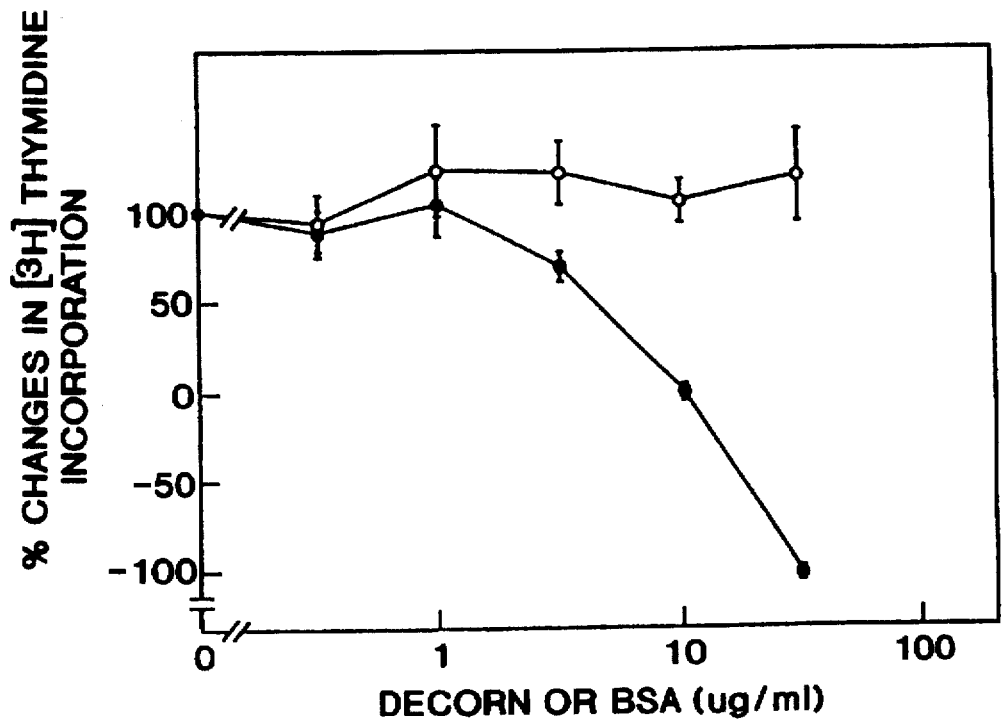
FIG. 4A
FIG. 4B
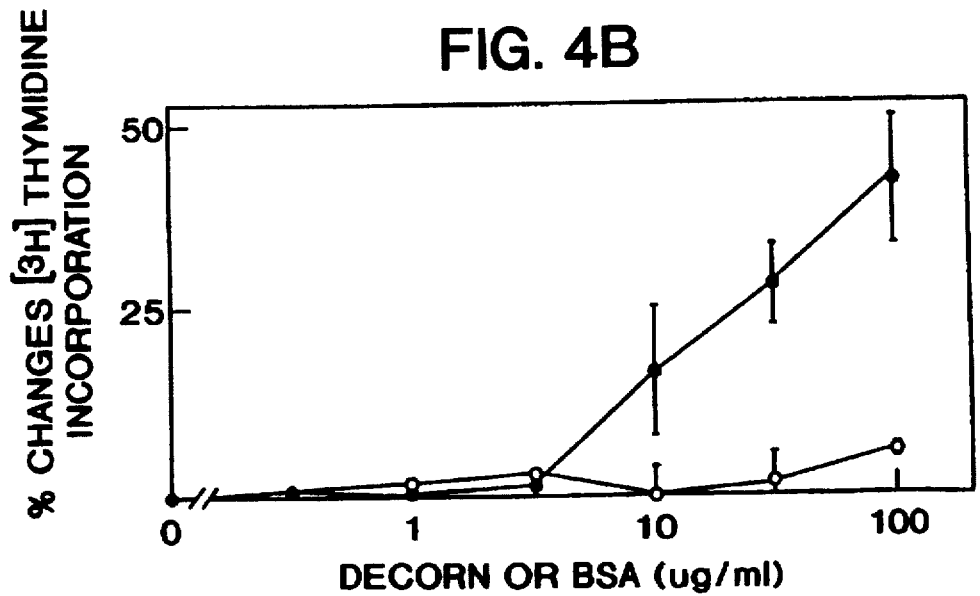

SEQUENCE LISTING ( 1 ) GENERAL INFORMATION:

( i i i ) NUMBER OF SEQUENCES: 62

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:1:

```
Asp Glu Ala Ser Gly Ile Gly Pro Glu Val Pro Asp Asp Arg Asp
 1           5                  10                  15
```

( 2 ) INFORMATION FOR SEQ ID NO:2:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
GGGAATTCGA TGAGGCTTCT GGGATAGGC                                    29
```

( 2 ) INFORMATION FOR SEQ ID NO:3:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
GGTCTAGACT ACTTACTTAT AGTTTCCGAG TTGAATGG                          38
```

( 2 ) INFORMATION FOR SEQ ID NO:4:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
GGTCTAGATT AGTCCAGACC CAAATCAGAA C                                 31
```

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GGTCTAGATT AAGGACTAAC TTTGCTAATT TTATTG  36

( 2 ) INFORMATION FOR SEQ ID NO:6:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GGTCTAGATT ATTTTCGCAC TTTGGTGATC TC  32

( 2 ) INFORMATION FOR SEQ ID NO:7:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GGTCTAGATT AGCTGGTGAT ATTGGTATCA GC  32

( 2 ) INFORMATION FOR SEQ ID NO:8:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GGTCTAGATT AATTGTCAAC AGCAGAGATG CT  32

( 2 ) INFORMATION FOR SEQ ID NO:9:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GGTCTAGATT ATCCAACTAC AGAGATATTG TTG  33

( 2 ) INFORMATION FOR SEQ ID NO:10:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GGTCTAGATT ACGGGTTGCT GAAAAGACTC AC  32

( 2 ) INFORMATION FOR SEQ ID NO:11:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
GGTCTAGATT AGTCCAGACC CAAATCAGAA GACTGGACCA CTCGAAGATG GGATTGAGAG    60
CGGAAGGGGG ACACTGG                                                  77
```

( 2 ) INFORMATION FOR SEQ ID NO:12:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
GGTCTAGATT AGTCCAGACC CAAATCAGAA CACTGGACCA CTCGAAGATG GGATTGAGAG    60
CGGAA                                                               65
```

( 2 ) INFORMATION FOR SEQ ID NO:13:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
GGGAATTCTC AAGTGACTTC TGCCCACCT                                     29
```

( 2 ) INFORMATION FOR SEQ ID NO:14:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
GGGAATTCTC AAGTGACTTC TCCCCACCT                                     29
```

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
AATTTATCGA GGGTAGGGGT GAATTCTAAT                                    30
```

( 2 ) INFORMATION FOR SEQ ID NO:16:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:16:

CTAGATTAGA ATTCACCCCT ACCCTCGATA    30

( 2 ) INFORMATION FOR SEQ ID NO:17:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:17:

His Leu Arg Val Val Gln Ser
1                5

( 2 ) INFORMATION FOR SEQ ID NO:18:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:18:

Pro Phe Arg Ser Gln Ser His Leu Arg Val Val Gln
1                5                          10

( 2 ) INFORMATION FOR SEQ ID NO:19:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:19:

His Leu Arg Val Val Gln Ser Ser Asp Leu Gly Leu
1                5                          10

( 2 ) INFORMATION FOR SEQ ID NO:20:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:20:

Pro Phe Arg Cys Gln Cys His Leu Arg Val Val Gln
1                5                          10

( 2 ) INFORMATION FOR SEQ ID NO:21:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:21:

```
Asp Glu Ala Ser Gly Ile Gly Pro Glu Val Pro Asp Asp Arg Asp
 1               5                  10                   15
```

( 2 ) INFORMATION FOR SEQ ID NO:22:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:22:

```
Val Pro Asp Asp Arg Asp Phe Glu Pro Ser Leu Gly
 1               5                  10
```

( 2 ) INFORMATION FOR SEQ ID NO:23:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:23:

```
Phe Glu Pro Ser Leu Gly Pro Val Cys Pro Phe Arg
 1               5                  10
```

( 2 ) INFORMATION FOR SEQ ID NO:24:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:24:

```
His Leu Arg Val Val Gln Cys Ser Asp Leu Gly Leu
 1               5                  10
```

( 2 ) INFORMATION FOR SEQ ID NO:25:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:25:

```
Cys Ser Asp Leu Gly Leu Asp Lys Val Pro Lys Asp Leu Pro Pro Asp
1               5                   10                  15
```

( 2 ) INFORMATION FOR SEQ ID NO:26:

( i ) SEQUENCE CHARACTERISTICS:
        ( A ) LENGTH: 1002 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: join(1..993, 997..1002)

( x i ) SEQUENCE DESCRIPTION: SEQ ID NO:26:

```
GAA TTC GAT GAG GCT TCT GGG ATA GGC CCA GAA GTT CCT GAT GAC CGC      48
Glu Phe Asp Glu Ala Ser Gly Ile Gly Pro Glu Val Pro Asp Asp Arg
1               5                   10                  15

GAC TTC GAG CCC TCC CTA GGC CCA GTG TGC CCC TTC CGC TGT CAA TGC      96
Asp Phe Glu Pro Ser Leu Gly Pro Val Cys Pro Phe Arg Cys Gln Cys
                20                  25                  30

CAT CTT CGA GTG GTC CAG TGT TCT GAT TTG GGT CTG GAC AAA GTG CCA     144
His Leu Arg Val Val Gln Cys Ser Asp Leu Gly Leu Asp Lys Val Pro
            35                  40                  45

AAG GAT CTT CCC CCT GAC ACA ACT CTG CTA GAC CTG CAA AAC AAC AAA     192
Lys Asp Leu Pro Pro Asp Thr Thr Leu Leu Asp Leu Gln Asn Asn Lys
50                  55                  60

ATA ACC GAA ATC AAA GAT GGA GAC TTT AAG AAC CTG AAG AAC CTT CAC     240
Ile Thr Glu Ile Lys Asp Gly Asp Phe Lys Asn Leu Lys Asn Leu His
65                  70                  75                  80

GCA TTG ATT CTT GTC AAC AAT AAA ATT AGC AAA GTT AGT CCT GGA GCA     288
Ala Leu Ile Leu Val Asn Asn Lys Ile Ser Lys Val Ser Pro Gly Ala
                85                  90                  95

TTT ACA CCT TTG GTG AAG TTG GAA CGA CTT TAT CTG TCC AAG AAT CAG     336
Phe Thr Pro Leu Val Lys Leu Glu Arg Leu Tyr Leu Ser Lys Asn Gln
                100                 105                 110

CTG AAG GAA TTG CCA GAA AAA ATG CCC AAA ACT CTT CAG GAG CTG CGT     384
Leu Lys Glu Leu Pro Glu Lys Met Pro Lys Thr Leu Gln Glu Leu Arg
            115                 120                 125

GCC CAT GAG AAT GAG ATC ACC AAA GTG CGA AAA GTT ACT TTC AAT GGA     432
Ala His Glu Asn Glu Ile Thr Lys Val Arg Lys Val Thr Phe Asn Gly
130                 135                 140

CTG AAC CAG ATG ATT GTC ATA GAA CTG GGC ACC AAT CCG CTG AAG AGC     480
Leu Asn Gln Met Ile Val Ile Glu Leu Gly Thr Asn Pro Leu Lys Ser
145                 150                 155                 160

TCA GGA ATT GAA AAT GGG GCT TTC CAG GGA ATG AAG AAG CTC TCC TAC     528
Ser Gly Ile Glu Asn Gly Ala Phe Gln Gly Met Lys Lys Leu Ser Tyr
                165                 170                 175

ATC CGC ATT GCT GAT ACC AAT ATC ACC AGC ATT CCT CAA GGT CTT CCT     576
Ile Arg Ile Ala Asp Thr Asn Ile Thr Ser Ile Pro Gln Gly Leu Pro
                180                 185                 190

CCT TCC CTT ACG GAA TTA CAT CTT GAT GGC AAC AAA ATC AGC AGA GTT     624
Pro Ser Leu Thr Glu Leu His Leu Asp Gly Asn Lys Ile Ser Arg Val
            195                 200                 205

GAT GCA GCT AGC CTG AAA GGA CTG AAT AAT TTG GCT AAG TTG GGA TTG     672
Asp Ala Ala Ser Leu Lys Gly Leu Asn Asn Leu Ala Lys Leu Gly Leu
210                 215                 220

AGT TTC AAC AGC ATC TCT GCT GTT GAC AAT GGC TCT CTG GCC AAC ACG     720
```

```
Ser  Phe  Asn  Ser  Ile  Ser  Ala  Val  Asp  Asn  Gly  Ser  Leu  Ala  Asn  Thr
225                 230                      235                      240

CCT  CAT  CTG  AGG  GAG  CTT  CAC  TTG  GAC  AAC  AAC  AAG  CTT  ACC  AGA  GTA              768
Pro  His  Leu  Arg  Glu  Leu  His  Leu  Asp  Asn  Asn  Lys  Leu  Thr  Arg  Val
                    245                      250                      255

CCT  GGT  GGG  CTG  GCA  GAG  CAT  AAG  TAC  ATC  CAG  GTT  GTC  TAC  CTT  CAT              816
Pro  Gly  Gly  Leu  Ala  Glu  His  Lys  Tyr  Ile  Gln  Val  Val  Tyr  Leu  His
                260                      265                      270

AAC  AAC  AAT  ATC  TCT  GTA  GTT  GGA  TCA  AGT  GAC  TTC  TGC  CCA  CCT  GGA              864
Asn  Asn  Asn  Ile  Ser  Val  Val  Gly  Ser  Ser  Asp  Phe  Cys  Pro  Pro  Gly
           275                      280                      285

CAC  AAC  ACC  AAA  AAG  GCT  TCT  TAT  TCG  GGT  GTG  AGT  CTT  TTC  AGC  AAC              912
His  Asn  Thr  Lys  Lys  Ala  Ser  Tyr  Ser  Gly  Val  Ser  Leu  Phe  Ser  Asn
290                      295                      300

CCG  GTC  CAG  TAC  TGG  GAG  ATA  CAG  CCA  TCC  ACC  TTC  AGA  TGT  GTC  TAC              960
Pro  Val  Gln  Tyr  Trp  Glu  Ile  Gln  Pro  Ser  Thr  Phe  Arg  Cys  Val  Tyr
305                      310                      315                      320

GTG  CGC  TCT  GCC  ATT  CAA  CTC  GGA  AAC  TAT  AAG  TAA  TCT  AGA                        1002
Val  Arg  Ser  Ala  Ile  Gln  Leu  Gly  Asn  Tyr  Lys       Ser  Arg
                    325                      330
```

( 2 ) INFORMATION FOR SEQ ID NO:27:

( i ) SEQUENCE CHARACTERISTICS:
        ( A ) LENGTH: 333 amino acids
        ( B ) TYPE: amino acid
        ( D ) TOPOLOGY: linear ( i i ) MOLECULE TYPE: protein ( x i ) SEQUENCE DESCRIPTION: SEQ ID NO:27:

```
Glu  Phe  Asp  Glu  Ala  Ser  Gly  Ile  Gly  Pro  Glu  Val  Pro  Asp  Asp  Arg
1                   5                        10                      15

Asp  Phe  Glu  Pro  Ser  Leu  Gly  Pro  Val  Cys  Pro  Phe  Arg  Cys  Gln  Cys
                20                       25                      30

His  Leu  Arg  Val  Val  Gln  Cys  Ser  Asp  Leu  Gly  Leu  Asp  Lys  Val  Pro
               35                       40                      45

Lys  Asp  Leu  Pro  Pro  Asp  Thr  Thr  Leu  Leu  Asp  Leu  Gln  Asn  Asn  Lys
50                            55                      60

Ile  Thr  Glu  Ile  Lys  Asp  Gly  Asp  Phe  Lys  Asn  Leu  Lys  Asn  Leu  His
65                       70                      75                       80

Ala  Leu  Ile  Leu  Val  Asn  Asn  Lys  Ile  Ser  Lys  Val  Ser  Pro  Gly  Ala
                    85                       90                      95

Phe  Thr  Pro  Leu  Val  Lys  Leu  Glu  Arg  Leu  Tyr  Leu  Ser  Lys  Asn  Gln
                100                      105                     110

Leu  Lys  Glu  Leu  Pro  Glu  Lys  Met  Pro  Lys  Thr  Leu  Gln  Glu  Leu  Arg
               115                      120                     125

Ala  His  Glu  Asn  Glu  Ile  Thr  Lys  Val  Arg  Lys  Val  Thr  Phe  Asn  Gly
130                           135                     140

Leu  Asn  Gln  Met  Ile  Val  Ile  Glu  Leu  Gly  Thr  Asn  Pro  Leu  Lys  Ser
145                      150                     155                      160

Ser  Gly  Ile  Glu  Asn  Gly  Ala  Phe  Gln  Gly  Met  Lys  Lys  Leu  Ser  Tyr
                    165                      170                     175

Ile  Arg  Ile  Ala  Asp  Thr  Asn  Ile  Thr  Ser  Ile  Pro  Gln  Gly  Leu  Pro
                180                      185                     190

Pro  Ser  Leu  Thr  Glu  Leu  His  Leu  Asp  Gly  Asn  Lys  Ile  Ser  Arg  Val
               195                      200                     205

Asp  Ala  Ala  Ser  Leu  Lys  Gly  Leu  Asn  Asn  Leu  Ala  Lys  Leu  Gly  Leu
210                           215                     220
```

| Ser 225 | Phe | Asn | Ser | Ile 230 | Ser | Ala | Val | Asp | Asn 235 | Gly | Ser | Leu | Ala | Asn 240 | Thr |
| | | | | | | | | | | | | | | | |
| Pro | His | Leu | Arg | Glu 245 | Leu | His | Leu | Asp | Asn 250 | Lys | Leu | Thr | Arg 255 | Val | |
| Pro | Gly | Gly | Leu 260 | Ala | Glu | His | Lys | Tyr 265 | Ile | Gln | Val | Val | Tyr 270 | Leu | His |
| Asn | Asn | Asn 275 | Ile | Ser | Val | Val | Gly 280 | Ser | Ser | Asp | Phe | Cys 285 | Pro | Pro | Gly |
| His | Asn 290 | Thr | Lys | Lys | Ala | Ser 295 | Tyr | Ser | Gly | Val | Ser 300 | Leu | Phe | Ser | Asn |
| Pro 305 | Val | Gln | Tyr | Trp | Glu 310 | Ile | Gln | Pro | Ser | Thr 315 | Phe | Arg | Cys | Val | Tyr 320 |
| Val | Arg | Ser | Ala | Ile 325 | Gln | Leu | Gly | Asn | Tyr 330 | Lys | Ser | Arg | | | |

( 2 ) INFORMATION FOR SEQ ID NO:28:

( i ) SEQUENCE CHARACTERISTICS:
( A ) LENGTH: 1002 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:28:

```
CTTAAGCTAC TCCGAAGACC CTATCCGGGT CTTCAAGGAC TACTGGCGCT GAAGCTCGGG    60
AGGGATCCGG GTCACACGGG GAAGGCGACA GTTACGGTAG AAGCTCACCA GGTCACAAGA   120
CTAAACCCAG ACCTGTTTCA CGGTTTCCTA GAAGGGGGAC TGTGTTGAGA CGATCTGGAC   180
GTTTTGTTGT TTTATTGGCT TTAGTTTCTA CCTCTGAAAT TCTTGGACTT CTTGGAAGTG   240
CGTAACTAAG AACAGTTGTT ATTTAATCG TTTCAATCAG GACCTCGTAA ATGTGGAAAC   300
CACTTCAACC TTGCTGAAAT AGACAGGTTC TTAGTCGACT TCCTTAACGG TCTTTTTTAC   360
GGGTTTTGAG AAGTCCTCGA CGCACGGGTA CTCTTACTCT AGTGGTTTCA CGCTTTTCAA   420
TGAAAGTTAC CTGACTTGGT CTACTAACAG TATCTTGACC CGTGGTTAGG CGACTTCTCG   480
AGTCCTTAAC TTTTACCCCG AAAGGTCCCT TACTTCTTCG AGAGGATGTA GGCGTAACGA   540
CTATGGTTAT AGTGGTCGTA AGGAGTTCCA GAAGGAGGAA GGGAATGCCT TAATGTAGAA   600
CTACCGTTGT TTTAGTCGTC TCAACTACGT CGATCGGACT TTCCTGACTT ATTAAACCGA   660
TTCAACCCTA ACTCAAAGTT GTCGTAGAGA CGACAACTGT TACCGAGAGA CCGGTTGTGC   720
GGAGTAGACT CCCTCGAAGT GAACCTGTTG TTGTTCGAAT GGTCTCATGG ACCACCCGAC   780
CGTCTCGTAT TCATGTAGGT CCAACAGATG GAAGTATTGT TGTTATAGAG ACATCAACCT   840
AGTTCACTGA AGACGGGTGG ACCTGTGTTG TGGTTTTTCC GAAGAATAAG CCCACACTCA   900
GAAAAGTCGT TGGGCCAGGT CATGACCCTC TATGTCGGTA GGTGGAAGTC TACACAGATG   960
CACGCGAGAC GGTAAGTTGA GCCTTTGATA TTCATTAGAT CT                     1002
```

( 2 ) INFORMATION FOR SEQ ID NO:29:

( i ) SEQUENCE CHARACTERISTICS:
( A ) LENGTH: 144 base pairs
( B ) TYPE: nucleic acid
( C ) STRANDEDNESS: double
( D ) TOPOLOGY: linear ( i i ) MOLECULE TYPE: cDNA ( i x ) FEATURE:
    ( A ) NAME/KEY: CDS
    ( B ) LOCATION: join(1..135, 139..144)

( x i ) SEQUENCE DESCRIPTION: SEQ ID NO:29:

```
GAA TTC GAT GAG GCT TCT GGG ATA GGC CCA GAA GTT CCT GAT GAC CGC    48
Glu Phe Asp Glu Ala Ser Gly Ile Gly Pro Glu Val Pro Asp Asp Arg
 1               5                  10                  15

GAC TTC GAG CCC TCC CTA GGC CCA GTG TAC CCC TTC CGC TGT CAA TGC    96
Asp Phe Glu Pro Ser Leu Gly Pro Val Tyr Pro Phe Arg Cys Gln Cys
             20                  25                  30

CAT CTT CGA GTG GTC CAG TGT TCT GAT TTG GGT CTG GAC TAA TCT AGA   144
His Leu Arg Val Val Gln Cys Ser Asp Leu Gly Leu Asp     Ser Arg
         35                  40                  45
```

( 2 ) INFORMATION FOR SEQ ID NO:30:

( i ) SEQUENCE CHARACTERISTICS:
        ( A ) LENGTH: 47 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

```
Glu Phe Asp Glu Ala Ser Gly Ile Gly Pro Glu Val Pro Asp Asp Arg
 1               5                  10                  15

Asp Phe Glu Pro Ser Leu Gly Pro Val Tyr Pro Phe Arg Cys Gln Cys
             20                  25                  30

His Leu Arg Val Val Gln Cys Ser Asp Leu Gly Leu Asp Ser Arg
         35                  40                  45
```

( 2 ) INFORMATION FOR SEQ ID NO:31:

( i ) SEQUENCE CHARACTERISTICS:
        ( A ) LENGTH: 144 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:31:

```
CTTAAGCTAC TCCGAAGACC CTATCCGGGT CTTCAAGGAC TACTGGCGCT GAAGCTCGGG     60

AGGGATCCGG GTCACATGGG GAAGGCGACA GTTACGGTAG AAGCTCACCA GGTCACAAGA    120

CTAAACCCAG ACCTGATTAG ATCT                                           144
```

( 2 ) INFORMATION FOR SEQ ID NO:32:

( i ) SEQUENCE CHARACTERISTICS:
        ( A ) LENGTH: 291 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: join(1..282, 286..291)

( x i ) SEQUENCE DESCRIPTION: SEQ ID NO:32:

```
GAA TTC GAT GAG GCT TCT GGG ATA GGC CCA GAA GTT CCT GAT GAC CGC    48
Glu Phe Asp Glu Ala Ser Gly Ile Gly Pro Glu Val Pro Asp Asp Arg
 1               5                  10                  15

GAC TTC GAG CCC TCC CTA GGC CCA GTG TGC CCC TTC CGC TGT CAA TGC    96
```

```
                                    Asp  Phe  Glu  Pro  Ser  Leu  Gly  Pro  Val  Cys  Pro  Phe  Arg  Cys  Gln  Cys
                                                    20                        25                        30

CAT  CTT  CGA  GTG  GTC  CAG  TGT  TCT  GAT  TTG  GGT  CTG  GAC  AAA  GTG  CCA                                        144
His  Leu  Arg  Val  Val  Gln  Cys  Ser  Asp  Leu  Gly  Leu  Asp  Lys  Val  Pro
               35                        40                        45

AAG  GAT  CTT  CCC  CCT  GAC  ACA  ACT  CTG  CTA  GAC  CTG  CAA  AAC  AAC  AAA                                        192
Lys  Asp  Leu  Pro  Pro  Asp  Thr  Thr  Leu  Leu  Asp  Leu  Gln  Asn  Asn  Lys
          50                        55                        60

ATA  ACC  GAA  ATC  AAA  GAT  GGA  GAC  TTT  AAG  AAC  CTG  AAG  AAC  CTT  CAC                                        240
Ile  Thr  Glu  Ile  Lys  Asp  Gly  Asp  Phe  Lys  Asn  Leu  Lys  Asn  Leu  His
65                        70                        75                        80

GCA  TTG  ATT  CTT  GTC  AAC  AAT  AAA  ATT  AGC  AAA  GTT  AGT  CCT                                                  282
Ala  Leu  Ile  Leu  Val  Asn  Asn  Lys  Ile  Ser  Lys  Val  Ser  Pro
                    85                        90

TAA  TCT  AGA                                                                                                         291
     Ser  Arg
     95
```

( 2 ) INFORMATION FOR SEQ ID NO:33:

( i ) SEQUENCE CHARACTERISTICS:
            ( A ) LENGTH: 96 amino acids
            ( B ) TYPE: amino acid
            ( D ) TOPOLOGY: linear ( i i ) MOLECULE TYPE: protein ( x i ) SEQUENCE DESCRIPTION: SEQ ID NO:33:

```
Glu  Phe  Asp  Glu  Ala  Ser  Gly  Ile  Gly  Pro  Glu  Val  Pro  Asp  Asp  Arg
 1                   5                        10                        15

Asp  Phe  Glu  Pro  Ser  Leu  Gly  Pro  Val  Cys  Pro  Phe  Arg  Cys  Gln  Cys
                    20                        25                        30

His  Leu  Arg  Val  Val  Gln  Cys  Ser  Asp  Leu  Gly  Leu  Asp  Lys  Val  Pro
               35                        40                        45

Lys  Asp  Leu  Pro  Pro  Asp  Thr  Thr  Leu  Leu  Asp  Leu  Gln  Asn  Asn  Lys
          50                        55                        60

Ile  Thr  Glu  Ile  Lys  Asp  Gly  Asp  Phe  Lys  Asn  Leu  Lys  Asn  Leu  His
65                        70                        75                        80

Ala  Leu  Ile  Leu  Val  Asn  Asn  Lys  Ile  Ser  Lys  Val  Ser  Pro  Ser  Arg
                    85                        90                        95
```

( 2 ) INFORMATION FOR SEQ ID NO:34:

( i ) SEQUENCE CHARACTERISTICS:
            ( A ) LENGTH: 291 base pairs
            ( B ) TYPE: nucleic acid
            ( C ) STRANDEDNESS: double
            ( D ) TOPOLOGY: linear ( i i ) MOLECULE TYPE: cDNA ( x i ) SEQUENCE DESCRIPTION: SEQ ID NO:34:

```
CTTAAGCTAC   TCCGAAGACC   CTATCCGGGT   CTTCAAGGAC   TACTGGCGCT   GAAGCTCGGG     60
AGGGATCCGG   GTCACACGGG   GAAGGCGACA   GTTACGGTAG   AAGCTCACCA   GGTCACAAGA    120
CTAAACCCAG   ACCTGTTTCA   CGGTTTCCTA   GAAGGGGGAC   TGTGTTGAGA   CGATCTGGAC    180
GTTTTGTTGT   TTTATTGGCT   TTAGTTTCTA   CCTCTGAAAT   TCTTGGACTT   CTTGGAAGTG    240
CGTAACTAAG   AACAGTTGTT   ATTTAATCG    TTTCAATCAG   GAATTAGATC   T              291
```

( 2 ) INFORMATION FOR SEQ ID NO:35:

( i ) SEQUENCE CHARACTERISTICS:

(A) LENGTH: 426 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: join(1..417, 421..426)

(xi) SEQUENCE DESCRIPTION: SEQ ID NO:35:

| GAA | TTC | GAT | GAG | GCT | TCT | GGG | ATA | GGC | CCA | GAA | GTT | CCT | GAT | GAC | CGC | 48 |
| Glu | Phe | Asp | Glu | Ala | Ser | Gly | Ile | Gly | Pro | Glu | Val | Pro | Asp | Asp | Arg | |
| 1 | | | | 5 | | | | | 10 | | | | | 15 | | |

| GAC | TTC | GAG | CCC | TCC | CTA | GGC | CCA | GTG | TGC | CCC | TTC | CGC | TGT | CAA | TGC | 96 |
| Asp | Phe | Glu | Pro | Ser | Leu | Gly | Pro | Val | Cys | Pro | Phe | Arg | Cys | Gln | Cys | |
| | | 20 | | | | | 25 | | | | | | 30 | | | |

| CAT | CTT | CGA | GTG | GTC | CAG | TGT | TCT | GAT | TTG | GGT | CTG | GAC | AAA | GTG | CCA | 144 |
| His | Leu | Arg | Val | Val | Gln | Cys | Ser | Asp | Leu | Gly | Leu | Asp | Lys | Val | Pro | |
| | | 35 | | | | | 40 | | | | | 45 | | | | |

| AAG | GAT | CTT | CCC | CCT | GAC | ACA | ACT | CTG | CTA | GAC | CTG | CAA | AAC | AAC | AAA | 192 |
| Lys | Asp | Leu | Pro | Pro | Asp | Thr | Thr | Leu | Leu | Asp | Leu | Gln | Asn | Asn | Lys | |
| | 50 | | | | | 55 | | | | | 60 | | | | | |

| ATA | ACC | GAA | ATC | AAA | GAT | GGA | GAC | TTT | AAG | AAC | CTG | AAG | AAC | CTT | CAC | 240 |
| Ile | Thr | Glu | Ile | Lys | Asp | Gly | Asp | Phe | Lys | Asn | Leu | Lys | Asn | Leu | His | |
| 65 | | | | | 70 | | | | | 75 | | | | | 80 | |

| GCA | TTG | ATT | CTT | GTC | AAC | AAT | AAA | ATT | AGC | AAA | GTT | AGT | CCT | GGA | GCA | 288 |
| Ala | Leu | Ile | Leu | Val | Asn | Asn | Lys | Ile | Ser | Lys | Val | Ser | Pro | Gly | Ala | |
| | | | | 85 | | | | | 90 | | | | | 95 | | |

| TTT | ACA | CCT | TTG | GTG | AAG | TTG | GAA | CGA | CTT | TAT | CTG | TCC | AAG | AAT | CAG | 336 |
| Phe | Thr | Pro | Leu | Val | Lys | Leu | Glu | Arg | Leu | Tyr | Leu | Ser | Lys | Asn | Gln | |
| | | | 100 | | | | | 105 | | | | | 110 | | | |

| CTG | AAG | GAA | TTG | CCA | GAA | AAA | ATG | CCC | AAA | ACT | CTT | CAG | GAG | CTG | CGT | 384 |
| Leu | Lys | Glu | Leu | Pro | Glu | Lys | Met | Pro | Lys | Thr | Leu | Gln | Glu | Leu | Arg | |
| | | 115 | | | | | 120 | | | | | 125 | | | | |

| GCC | CAT | GAG | AAT | GAG | ATC | ACC | AAA | GTG | CGA | AAA | TAA | TCT | AGA | | | 426 |
| Ala | His | Glu | Asn | Glu | Ile | Thr | Lys | Val | Arg | Lys | | Ser | Arg | | | |
| | 130 | | | | | 135 | | | | | | 140 | | | | |

(2) INFORMATION FOR SEQ ID NO:36:

(i) SEQUENCE CHARACTERISTICS:
(A) LENGTH: 141 amino acids
(B) TYPE: amino acid
(D) TOPOLOGY: linear (ii) MOLECULE TYPE: protein (xi) SEQUENCE DESCRIPTION: SEQ ID NO:36:

| Glu | Phe | Asp | Glu | Ala | Ser | Gly | Ile | Gly | Pro | Glu | Val | Pro | Asp | Asp | Arg |
| 1 | | | | 5 | | | | | 10 | | | | | 15 | |

| Asp | Phe | Glu | Pro | Ser | Leu | Gly | Pro | Val | Cys | Pro | Phe | Arg | Cys | Gln | Cys |
| | | 20 | | | | | 25 | | | | | | 30 | | |

| His | Leu | Arg | Val | Val | Gln | Cys | Ser | Asp | Leu | Gly | Leu | Asp | Lys | Val | Pro |
| | | 35 | | | | | 40 | | | | | 45 | | | |

| Lys | Asp | Leu | Pro | Pro | Asp | Thr | Thr | Leu | Leu | Asp | Leu | Gln | Asn | Asn | Lys |
| | 50 | | | | | 55 | | | | | 60 | | | | |

| Ile | Thr | Glu | Ile | Lys | Asp | Gly | Asp | Phe | Lys | Asn | Leu | Lys | Asn | Leu | His |
| 65 | | | | | 70 | | | | | 75 | | | | | 80 |

| Ala | Leu | Ile | Leu | Val | Asn | Asn | Lys | Ile | Ser | Lys | Val | Ser | Pro | Gly | Ala |
| | | | | 85 | | | | | 90 | | | | | 95 | |

| Phe | Thr | Pro | Leu | Val | Lys | Leu | Glu | Arg | Leu | Tyr | Leu | Ser | Lys | Asn | Gln |

|     |     |     |     |     |     |     | 100 |     |     |     |     | 105 |     |     |     |     | 110 |     |     |
| --- | --- | --- | --- | --- | --- | --- | --- | --- | --- | --- | --- | --- | --- | --- | --- | --- | --- | --- | --- |

Leu Lys Glu Leu Pro Glu Lys Met Pro Lys Thr Leu Gln Glu Leu Arg
        115             120             125

Ala His Glu Asn Glu Ile Thr Lys Val Arg Lys Ser Arg
  130            135            140

( 2 ) INFORMATION FOR SEQ ID NO:37:

( i ) SEQUENCE CHARACTERISTICS:
      ( A ) LENGTH: 426 base pairs
      ( B ) TYPE: nucleic acid
      ( C ) STRANDEDNESS: double
      ( D ) TOPOLOGY: linear ( i i ) MOLECULE TYPE: cDNA ( x i ) SEQUENCE DESCRIPTION: SEQ ID NO:37:

```
CTTAAGCTAC TCCGAAGACC CTATCCGGGT CTTCAAGGAC TACTGGCGCT GAAGCTCGGG      60
AGGGATCCGG GTCACACGGG GAAGGCGACA GTTACGGTAG AAGCTCACCA GGTCACAAGA     120
CTAAACCCAG ACCTGTTTCA CGGTTTCCTA GAAGGGGGAC TGTGTTGAGA CGATCTGGAC     180
GTTTTGTTGT TTTATTGGCT TTAGTTTCTA CCTCTGAAAT TCTTGGACTT CTTGGAAGTG     240
CGTAACTAAG AACAGTTGTT ATTTTAATCG TTTCAATCAG GACCTCGTAA ATGTGGAAAC     300
CACTTCAACC TTGCTGAAAT AGACAGGTTC TTAGTCGACT TCCTTAACGG TCTTTTTTAC     360
GGGTTTTGAG AAGTCCTCGA CGCACGGGTA CTCTTACTCT AGTGGTTTCA CGCTTTTATT     420
AGATCT                                                               426
```

( 2 ) INFORMATION FOR SEQ ID NO:38:

( i ) SEQUENCE CHARACTERISTICS:
      ( A ) LENGTH: 567 base pairs
      ( B ) TYPE: nucleic acid
      ( C ) STRANDEDNESS: double
      ( D ) TOPOLOGY: linear ( i i ) MOLECULE TYPE: cDNA ( i x ) FEATURE:
      ( A ) NAME/KEY: CDS
      ( B ) LOCATION: join(1..558, 562..567)

( x i ) SEQUENCE DESCRIPTION: SEQ ID NO:38:

```
GAA TTC GAT GAG GCT TCT GGG ATA GGC CCA GAA GTT CCT GAT GAC CGC       48
Glu Phe Asp Glu Ala Ser Gly Ile Gly Pro Glu Val Pro Asp Asp Arg
 1               5                  10                  15

GAC TTC GAG CCC TCC CTA GGC CCA GTG TGC CCC TTC CGC TGT CAA TGC       96
Asp Phe Glu Pro Ser Leu Gly Pro Val Cys Pro Phe Arg Cys Gln Cys
            20                  25                  30

CAT CTT CGA GTG GTC CAG TGT TCT GAT TTG GGT CTG GAC AAA GTG CCA      144
His Leu Arg Val Val Gln Cys Ser Asp Leu Gly Leu Asp Lys Val Pro
         35                  40                  45

AAG GAT CTT CCC CCT GAC ACA ACT CTG CTA GAC CTG CAA AAC AAC AAA      192
Lys Asp Leu Pro Pro Asp Thr Thr Leu Leu Asp Leu Gln Asn Asn Lys
     50                  55                  60

ATA ACC GAA ATC AAA GAT GGA GAC TTT AAG AAC CTG AAG AAC CTT CAC      240
Ile Thr Glu Ile Lys Asp Gly Asp Phe Lys Asn Leu Lys Asn Leu His
 65                  70                  75                  80

GCA TTG ATT CTT GTC AAC AAT AAA ATT AGC AAA GTT AGT CCT GGA GCA      288
Ala Leu Ile Leu Val Asn Asn Lys Ile Ser Lys Val Ser Pro Gly Ala
                 85                  90                  95

TTT ACA CCT TTG GTG AAG TTG GAA CGA CTT TAT CTG TCC AAG AAT CAG      336
Phe Thr Pro Leu Val Lys Leu Glu Arg Leu Tyr Leu Ser Lys Asn Gln
```

```
                        100                         105                         110
CTG   AAG   GAA   TTG   CCA   GAA   AAA   ATG   CCC   AAA   ACT   CTT   CAG   GAG   CTG   CGT      384
Leu   Lys   Glu   Leu   Pro   Glu   Lys   Met   Pro   Lys   Thr   Leu   Gln   Glu   Leu   Arg
            115                           120                     125

GCC   CAT   GAG   AAT   GAG   ATC   ACC   AAA   GTG   CGA   AAA   GTT   ACT   TTC   AAT   GGA      432
Ala   His   Glu   Asn   Glu   Ile   Thr   Lys   Val   Arg   Lys   Val   Thr   Phe   Asn   Gly
      130                           135                           140

CTG   AAC   CAG   ATG   ATT   GTC   ATA   GAA   CTG   GGC   ACC   AAT   CCG   CTG   AAG   AGC      480
Leu   Asn   Gln   Met   Ile   Val   Ile   Glu   Leu   Gly   Thr   Asn   Pro   Leu   Lys   Ser
145                           150                           155                           160

TCA   GGA   ATT   GAA   AAT   GGG   GCT   TTC   CAG   GGA   ATG   AAG   AAG   CTC   TCC   TAC      528
Ser   Gly   Ile   Glu   Asn   Gly   Ala   Phe   Gln   Gly   Met   Lys   Lys   Leu   Ser   Tyr
                        165                           170                           175

ATC   CGC   ATT   GCT   GAT   ACC   AAT   ATC   ACC   AGC   TAA   TCT   AGA                       567
Ile   Arg   Ile   Ala   Asp   Thr   Asn   Ile   Thr   Ser         Ser   Arg
                  180                           185
```

( 2 ) INFORMATION FOR SEQ ID NO:39:

( i ) SEQUENCE CHARACTERISTICS:
        ( A ) LENGTH: 188 amino acids
        ( B ) TYPE: amino acid
        ( D ) TOPOLOGY: linear ( i i ) MOLECULE TYPE: protein ( x i ) SEQUENCE DESCRIPTION: SEQ ID NO:39:

```
Glu   Phe   Asp   Glu   Ala   Ser   Gly   Ile   Gly   Pro   Glu   Val   Pro   Asp   Asp   Arg
1                       5                           10                          15

Asp   Phe   Glu   Pro   Ser   Leu   Gly   Pro   Val   Cys   Pro   Phe   Arg   Cys   Gln   Cys
                  20                          25                          30

His   Leu   Arg   Val   Val   Gln   Cys   Ser   Asp   Leu   Gly   Leu   Asp   Lys   Val   Pro
            35                          40                          45

Lys   Asp   Leu   Pro   Pro   Asp   Thr   Thr   Leu   Leu   Asp   Leu   Gln   Asn   Asn   Lys
      50                          55                          60

Ile   Thr   Glu   Ile   Lys   Asp   Gly   Asp   Phe   Lys   Asn   Leu   Lys   Asn   Leu   His
65                          70                          75                          80

Ala   Leu   Ile   Leu   Val   Asn   Asn   Lys   Ile   Ser   Lys   Val   Ser   Pro   Gly   Ala
                        85                          90                          95

Phe   Thr   Pro   Leu   Val   Lys   Leu   Glu   Arg   Leu   Tyr   Leu   Ser   Lys   Asn   Gln
                  100                         105                         110

Leu   Lys   Glu   Leu   Pro   Glu   Lys   Met   Pro   Lys   Thr   Leu   Gln   Glu   Leu   Arg
            115                         120                         125

Ala   His   Glu   Asn   Glu   Ile   Thr   Lys   Val   Arg   Lys   Val   Thr   Phe   Asn   Gly
      130                         135                         140

Leu   Asn   Gln   Met   Ile   Val   Ile   Glu   Leu   Gly   Thr   Asn   Pro   Leu   Lys   Ser
145                         150                         155                         160

Ser   Gly   Ile   Glu   Asn   Gly   Ala   Phe   Gln   Gly   Met   Lys   Lys   Leu   Ser   Tyr
                        165                         170                         175

Ile   Arg   Ile   Ala   Asp   Thr   Asn   Ile   Thr   Ser   Ser   Arg
                  180                         185
```

( 2 ) INFORMATION FOR SEQ ID NO:40:

( i ) SEQUENCE CHARACTERISTICS:
        ( A ) LENGTH: 567 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:40:

| | | | | | |
|---|---|---|---|---|---|
| CTTAAGCTAC | TCCGAAGACC | CTATCCGGGT | CTTCAAGGAC | TACTGGCGCT | GAAGCTCGGG | 60 |
| AGGGATCCGG | GTCACACGGG | GAAGGCGACA | GTTACGGTAG | AAGCTCACCA | GGTCACAAGA | 120 |
| CTAAACCCAG | ACCTGTTTCA | CGGTTTCCTA | GAAGGGGGAC | TGTGTTGAGA | CGATCTGGAC | 180 |
| GTTTTGTTGT | TTTATTGGCT | TTAGTTTCTA | CCTCTGAAAT | TCTTGGACTT | CTTGGAAGTG | 240 |
| CGTAACTAAG | AACAGTTGTT | ATTTTAATCG | TTTCAATCAG | GACCTCGTAA | ATGTGGAAAC | 300 |
| CACTTCAACC | TTGCTGAAAT | AGACAGGTTC | TTAGTCGACT | TCCTTAACGG | TCTTTTTTAC | 360 |
| GGGTTTTGAG | AAGTCCTCGA | CGCACGGGTA | CTCTTACTCT | AGTGGTTTCA | CGCTTTTCAA | 420 |
| TGAAAGTTAC | CTGACTTGGT | CTACTAACAG | TATCTTGACC | CGTGGTTAGG | CGACTTCTCG | 480 |
| AGTCCTTAAC | TTTTACCCCG | AAAGGTCCCT | TACTTCTTCG | AGAGGATGTA | GGCGTAACGA | 540 |
| CTATGGTTAT | AGTGGTCGAT | TAGATCT | | | | 567 |

( 2 ) INFORMATION FOR SEQ ID NO:41:

( i ) SEQUENCE CHARACTERISTICS:
        ( A ) LENGTH: 711 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: join(1..702, 706..711)

( x i ) SEQUENCE DESCRIPTION: SEQ ID NO:41:

| GAA | TTC | GAT | GAG | GCT | TCT | GGG | ATA | GGC | CCA | GAA | GTT | CCT | GAT | GAC | CGC | 48 |
|---|---|---|---|---|---|---|---|---|---|---|---|---|---|---|---|---|
| Glu | Phe | Asp | Glu | Ala | Ser | Gly | Ile | Gly | Pro | Glu | Val | Pro | Asp | Asp | Arg | |
| 1 | | | | 5 | | | | | 10 | | | | | 15 | | |

| GAC | TTC | GAG | CCC | TCC | CTA | GGC | CCA | GTG | TGC | CCC | TTC | CGC | TGT | CAA | TGC | 96 |
|---|---|---|---|---|---|---|---|---|---|---|---|---|---|---|---|---|
| Asp | Phe | Glu | Pro | Ser | Leu | Gly | Pro | Val | Cys | Pro | Phe | Arg | Cys | Gln | Cys | |
| | | 20 | | | | | 25 | | | | | 30 | | | | |

| CAT | CTT | CGA | GTG | GTC | CAG | TGT | TCT | GAT | TTG | GGT | CTG | GAC | AAA | GTG | CCA | 144 |
|---|---|---|---|---|---|---|---|---|---|---|---|---|---|---|---|---|
| His | Leu | Arg | Val | Val | Gln | Cys | Ser | Asp | Leu | Gly | Leu | Asp | Lys | Val | Pro | |
| | | 35 | | | | | 40 | | | | | 45 | | | | |

| AAG | GAT | CTT | CCC | CCT | GAC | ACA | ACT | CTG | CTA | GAC | CTG | CAA | AAC | AAC | AAA | 192 |
|---|---|---|---|---|---|---|---|---|---|---|---|---|---|---|---|---|
| Lys | Asp | Leu | Pro | Pro | Asp | Thr | Thr | Leu | Leu | Asp | Leu | Gln | Asn | Asn | Lys | |
| 50 | | | | | 55 | | | | | 60 | | | | | | |

| ATA | ACC | GAA | ATC | AAA | GAT | GGA | GAC | TTT | AAG | AAC | CTG | AAG | AAC | CTT | CAC | 240 |
|---|---|---|---|---|---|---|---|---|---|---|---|---|---|---|---|---|
| Ile | Thr | Glu | Ile | Lys | Asp | Gly | Asp | Phe | Lys | Asn | Leu | Lys | Asn | Leu | His | |
| 65 | | | | | 70 | | | | | 75 | | | | | 80 | |

| GCA | TTG | ATT | CTT | GTC | AAC | AAT | AAA | ATT | AGC | AAA | GTT | AGT | CCT | GGA | GCA | 288 |
|---|---|---|---|---|---|---|---|---|---|---|---|---|---|---|---|---|
| Ala | Leu | Ile | Leu | Val | Asn | Asn | Lys | Ile | Ser | Lys | Val | Ser | Pro | Gly | Ala | |
| | | | | 85 | | | | | 90 | | | | | 95 | | |

| TTT | ACA | CCT | TTG | GTG | AAG | TTG | GAA | CGA | CTT | TAT | CTG | TCC | AAG | AAT | CAG | 336 |
|---|---|---|---|---|---|---|---|---|---|---|---|---|---|---|---|---|
| Phe | Thr | Pro | Leu | Val | Lys | Leu | Glu | Arg | Leu | Tyr | Leu | Ser | Lys | Asn | Gln | |
| | | | | 100 | | | | | 105 | | | | | 110 | | |

| CTG | AAG | GAA | TTG | CCA | GAA | AAA | ATG | CCC | AAA | ACT | CTT | CAG | GAG | CTG | CGT | 384 |
|---|---|---|---|---|---|---|---|---|---|---|---|---|---|---|---|---|
| Leu | Lys | Glu | Leu | Pro | Glu | Lys | Met | Pro | Lys | Thr | Leu | Gln | Glu | Leu | Arg | |
| | | 115 | | | | | 120 | | | | | 125 | | | | |

| GCC | CAT | GAG | AAT | GAG | ATC | ACC | AAA | GTG | CGA | AAA | GTT | ACT | TTC | AAT | GGA | 432 |
|---|---|---|---|---|---|---|---|---|---|---|---|---|---|---|---|---|
| Ala | His | Glu | Asn | Glu | Ile | Thr | Lys | Val | Arg | Lys | Val | Thr | Phe | Asn | Gly | |
| | | 130 | | | | | 135 | | | | | 140 | | | | |

| CTG | AAC | CAG | ATG | ATT | GTC | ATA | GAA | CTG | GGC | ACC | AAT | CCG | CTG | AAG | AGC | 480 |
|---|---|---|---|---|---|---|---|---|---|---|---|---|---|---|---|---|
| Leu | Asn | Gln | Met | Ile | Val | Ile | Glu | Leu | Gly | Thr | Asn | Pro | Leu | Lys | Ser | |
| 145 | | | | | 150 | | | | | 155 | | | | | 160 | |

```
TCA GGA ATT GAA AAT GGG GCT TTC CAG GGA ATG AAG AAG CTC TCC TAC          528
Ser Gly Ile Glu Asn Gly Ala Phe Gln Gly Met Lys Lys Leu Ser Tyr
        165                 170                 175

ATC CGC ATT GCT GAT ACC AAT ATC ACC AGC ATT CCT CAA GGT CTT CCT          576
Ile Arg Ile Ala Asp Thr Asn Ile Thr Ser Ile Pro Gln Gly Leu Pro
            180                 185                 190

CCT TCC CTT ACG GAA TTA CAT CTT GAT GGC AAC AAA ATC AGC AGA GTT          624
Pro Ser Leu Thr Glu Leu His Leu Asp Gly Asn Lys Ile Ser Arg Val
        195                 200                 205

GAT GCA GCT AGC CTG AAA GGA CTG AAT AAT TTG GCT AAG TTG GGA TTG          672
Asp Ala Ala Ser Leu Lys Gly Leu Asn Asn Leu Ala Lys Leu Gly Leu
    210                 215                 220

AGT TTC AAC AGC ATC TCT GCT GTT GAC AAT TAA TCT AGA                      711
Ser Phe Asn Ser Ile Ser Ala Val Asp Asn     Ser Arg
225                 230                     235
```

(2) INFORMATION FOR SEQ ID NO:42:

(i) SEQUENCE CHARACTERISTICS:
        (A) LENGTH: 236 amino acids
        (B) TYPE: amino acid
        (D) TOPOLOGY: linear (ii) MOLECULE TYPE: protein (xi) SEQUENCE DESCRIPTION: SEQ ID NO:42:

```
Glu Phe Asp Glu Ala Ser Gly Ile Gly Pro Glu Val Pro Asp Asp Arg
 1               5                  10                  15

Asp Phe Glu Pro Ser Leu Gly Pro Val Cys Pro Phe Arg Cys Gln Cys
            20                  25                  30

His Leu Arg Val Val Gln Cys Ser Asp Leu Gly Leu Asp Lys Val Pro
        35                  40                  45

Lys Asp Leu Pro Pro Asp Thr Thr Leu Leu Asp Leu Gln Asn Asn Lys
    50                  55                  60

Ile Thr Glu Ile Lys Asp Gly Asp Phe Lys Asn Leu Lys Asn Leu His
65                  70                  75                  80

Ala Leu Ile Leu Val Asn Asn Lys Ile Ser Lys Val Ser Pro Gly Ala
                85                  90                  95

Phe Thr Pro Leu Val Lys Leu Glu Arg Leu Tyr Leu Ser Lys Asn Gln
            100                 105                 110

Leu Lys Glu Leu Pro Glu Lys Met Pro Lys Thr Leu Gln Glu Leu Arg
        115                 120                 125

Ala His Glu Asn Glu Ile Thr Lys Val Arg Lys Val Thr Phe Asn Gly
    130                 135                 140

Leu Asn Gln Met Ile Val Ile Glu Leu Gly Thr Asn Pro Leu Lys Ser
145                 150                 155                 160

Ser Gly Ile Glu Asn Gly Ala Phe Gln Gly Met Lys Lys Leu Ser Tyr
                165                 170                 175

Ile Arg Ile Ala Asp Thr Asn Ile Thr Ser Ile Pro Gln Gly Leu Pro
            180                 185                 190

Pro Ser Leu Thr Glu Leu His Leu Asp Gly Asn Lys Ile Ser Arg Val
        195                 200                 205

Asp Ala Ala Ser Leu Lys Gly Leu Asn Asn Leu Ala Lys Leu Gly Leu
    210                 215                 220

Ser Phe Asn Ser Ile Ser Ala Val Asp Asn Ser Arg
225                 230                 235
```

(2) INFORMATION FOR SEQ ID NO:43:

( i ) SEQUENCE CHARACTERISTICS:
    ( A ) LENGTH: 711 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:43:

```
CTTAAGCTAC TCCGAAGACC CTATCCGGGT CTTCAAGGAC TACTGGCGCT GAAGCTCGGG    60
AGGGATCCGG GTCACACGGG GAAGGCGACA GTTACGGTAG AAGCTCACCA GGTCACAAGA   120
CTAAACCCAG ACCTGTTTCA CGGTTTCCTA GAAGGGGAC TGTGTTGAGA CGATCTGGAC    180
GTTTGTTGT TTTATTGGCT TTAGTTTCTA CCTCTGAAAT TCTTGGACTT CTTGGAAGTG    240
CGTAACTAAG AACAGTTGTT ATTTAATCG TTTCAATCAG GACCTCGTAA ATGTGGAAAC    300
CACTTCAACC TTGCTGAAAT AGACAGGTTC TTAGTCGACT TCCTTAACGG TCTTTTTTAC   360
GGGTTTGAG AAGTCCTCGA CGCACGGGTA CTCTTACTCT AGTGGTTTCA CGCTTTTCAA    420
TGAAAGTTAC CTGACTTGGT CTACTAACAG TATCTTGACC CGTGGTTAGG CGACTTCTCG   480
AGTCCTTAAC TTTTACCCCG AAAGGTCCCT TACTTCTTCG AGAGGATGTA GGCGTAACGA   540
CTATGGTTAT AGTGGTCGTA AGGAGTTCCA GAAGGAGGAA GGGAATGCCT TAATGTAGAA   600
CTACCGTTGT TTTAGTCGTC TCAACTACGT CGATCGGACT TTCCTGACTT ATTAAACCGA   660
TTCAACCCTA ACTCAAAGTT GTCGTAGAGA CGACAACTGT TAATTAGATC T            711
```

( 2 ) INFORMATION FOR SEQ ID NO:44:

( i ) SEQUENCE CHARACTERISTICS:
        ( A ) LENGTH: 849 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: join(1..840, 844..849)

( x i ) SEQUENCE DESCRIPTION: SEQ ID NO:44:

```
GAA TTC GAT GAG GCT TCT GGG ATA GGC CCA GAA GTT CCT GAT GAC CGC                48
Glu Phe Asp Glu Ala Ser Gly Ile Gly Pro Glu Val Pro Asp Asp Arg
  1               5                  10                  15

GAC TTC GAG CCC TCC CTA GGC CCA GTG TGC CCC TTC CGC TGT CAA TGC                96
Asp Phe Glu Pro Ser Leu Gly Pro Val Cys Pro Phe Arg Cys Gln Cys
             20                  25                  30

CAT CTT CGA GTG GTC CAG TGT TCT GAT TTG GGT CTG GAC AAA GTG CCA               144
His Leu Arg Val Val Gln Cys Ser Asp Leu Gly Leu Asp Lys Val Pro
         35                  40                  45

AAG GAT CTT CCC CCT GAC ACA ACT CTG CTA GAC CTG CAA AAC AAC AAA               192
Lys Asp Leu Pro Pro Asp Thr Thr Leu Leu Asp Leu Gln Asn Asn Lys
     50                  55                  60

ATA ACC GAA ATC AAA GAT GGA GAC TTT AAG AAC CTG AAG AAC CTT CAC               240
Ile Thr Glu Ile Lys Asp Gly Asp Phe Lys Asn Leu Lys Asn Leu His
 65                  70                  75                  80

GCA TTG ATT CTT GTC AAC AAT AAA ATT AGC AAA GTT AGT CCT GGA GCA               288
Ala Leu Ile Leu Val Asn Asn Lys Ile Ser Lys Val Ser Pro Gly Ala
                 85                  90                  95

TTT ACA CCT TTG GTG AAG TTG GAA CGA CTT TAT CTG TCC AAG AAT CAG               336
Phe Thr Pro Leu Val Lys Leu Glu Arg Leu Tyr Leu Ser Lys Asn Gln
            100                 105                 110

CTG AAG GAA TTG CCA GAA AAA ATG CCC AAA ACT CTT CAG GAG CTG CGT               384
```

```
Leu  Lys  Glu  Leu  Pro  Glu  Lys  Met  Pro  Lys  Thr  Leu  Gln  Glu  Leu  Arg
          115                      120                      125

GCC  CAT  GAG  AAT  GAG  ATC  ACC  AAA  GTG  CGA  AAA  GTT  ACT  TTC  AAT  GGA        432
Ala  His  Glu  Asn  Glu  Ile  Thr  Lys  Val  Arg  Lys  Val  Thr  Phe  Asn  Gly
     130                      135                      140

CTG  AAC  CAG  ATG  ATT  GTC  ATA  GAA  CTG  GGC  ACC  AAT  CCG  CTG  AAG  AGC        480
Leu  Asn  Gln  Met  Ile  Val  Ile  Glu  Leu  Gly  Thr  Asn  Pro  Leu  Lys  Ser
145                      150                      155                      160

TCA  GGA  ATT  GAA  AAT  GGG  GCT  TTC  CAG  GGA  ATG  AAG  AAG  CTC  TCC  TAC        528
Ser  Gly  Ile  Glu  Asn  Gly  Ala  Phe  Gln  Gly  Met  Lys  Lys  Leu  Ser  Tyr
                    165                      170                      175

ATC  CGC  ATT  GCT  GAT  ACC  AAT  ATC  ACC  AGC  ATT  CCT  CAA  GGT  CTT  CCT        576
Ile  Arg  Ile  Ala  Asp  Thr  Asn  Ile  Thr  Ser  Ile  Pro  Gln  Gly  Leu  Pro
               180                      185                      190

CCT  TCC  CTT  ACG  GAA  TTA  CAT  CTT  GAT  GGC  AAC  AAA  ATC  AGC  AGA  GTT        624
Pro  Ser  Leu  Thr  Glu  Leu  His  Leu  Asp  Gly  Asn  Lys  Ile  Ser  Arg  Val
          195                      200                      205

GAT  GCA  GCT  AGC  CTG  AAA  GGA  CTG  AAT  AAT  TTG  GCT  AAG  TTG  GGA  TTG        672
Asp  Ala  Ala  Ser  Leu  Lys  Gly  Leu  Asn  Asn  Leu  Ala  Lys  Leu  Gly  Leu
     210                      215                      220

AGT  TTC  AAC  AGC  ATC  TCT  GCT  GTT  GAC  AAT  GGC  TCT  CTG  GCC  AAC  ACG        720
Ser  Phe  Asn  Ser  Ile  Ser  Ala  Val  Asp  Asn  Gly  Ser  Leu  Ala  Asn  Thr
225                      230                      235                      240

CCT  CAT  CTG  AGG  GAG  CTT  CAC  TTG  GAC  AAC  AAC  AAG  CTT  ACC  AGA  GTA        768
Pro  His  Leu  Arg  Glu  Leu  His  Leu  Asp  Asn  Asn  Lys  Leu  Thr  Arg  Val
                    245                      250                      255

CCT  GGT  GGG  CTG  GCA  GAG  CAT  AAG  TAC  ATC  CAG  GTT  GTC  TAC  CTT  CAT        816
Pro  Gly  Gly  Leu  Ala  Glu  His  Lys  Tyr  Ile  Gln  Val  Val  Tyr  Leu  His
               260                      265                      270

AAC  AAC  AAT  ATC  TCT  GTA  GTT  GGA  TAA  TCT  AGA                                  849
Asn  Asn  Asn  Ile  Ser  Val  Val  Gly       Ser  Arg
          275                      280
```

( 2 ) INFORMATION FOR SEQ ID NO:45:

( i ) SEQUENCE CHARACTERISTICS:
        ( A ) LENGTH: 282 amino acids
        ( B ) TYPE: amino acid
        ( D ) TOPOLOGY: linear ( i i ) MOLECULE TYPE: protein ( x i ) SEQUENCE DESCRIPTION: SEQ ID NO:45:

```
Glu  Phe  Asp  Glu  Ala  Ser  Gly  Ile  Gly  Pro  Glu  Val  Pro  Asp  Asp  Arg
1                   5                    10                       15

Asp  Phe  Glu  Pro  Ser  Leu  Gly  Pro  Val  Cys  Pro  Phe  Arg  Cys  Gln  Cys
               20                       25                       30

His  Leu  Arg  Val  Val  Gln  Cys  Ser  Asp  Leu  Gly  Leu  Asp  Lys  Val  Pro
          35                       40                       45

Lys  Asp  Leu  Pro  Pro  Asp  Thr  Thr  Leu  Leu  Asp  Leu  Gln  Asn  Asn  Lys
     50                       55                       60

Ile  Thr  Glu  Ile  Lys  Asp  Gly  Asp  Phe  Lys  Asn  Leu  Lys  Asn  Leu  His
65                       70                       75                       80

Ala  Leu  Ile  Leu  Val  Asn  Asn  Lys  Ile  Ser  Lys  Val  Ser  Pro  Gly  Ala
                    85                       90                       95

Phe  Thr  Pro  Leu  Val  Lys  Leu  Glu  Arg  Leu  Tyr  Leu  Ser  Lys  Asn  Gln
               100                      105                      110

Leu  Lys  Glu  Leu  Pro  Glu  Lys  Met  Pro  Lys  Thr  Leu  Gln  Glu  Leu  Arg
          115                      120                      125

Ala  His  Glu  Asn  Glu  Ile  Thr  Lys  Val  Arg  Lys  Val  Thr  Phe  Asn  Gly
```

```
                130                          135                          140
Leu  Asn  Gln  Met  Ile  Val  Ile  Glu  Leu  Gly  Thr  Asn  Pro  Leu  Lys  Ser
145                      150                     155                          160

Ser  Gly  Ile  Glu  Asn  Gly  Ala  Phe  Gln  Gly  Met  Lys  Lys  Leu  Ser  Tyr
                    165                     170                     175

Ile  Arg  Ile  Ala  Asp  Thr  Asn  Ile  Thr  Ser  Ile  Pro  Gln  Gly  Leu  Pro
               180                     185                     190

Pro  Ser  Leu  Thr  Glu  Leu  His  Leu  Asp  Gly  Asn  Lys  Ile  Ser  Arg  Val
          195                     200                     205

Asp  Ala  Ala  Ser  Leu  Lys  Gly  Leu  Asn  Asn  Leu  Ala  Lys  Leu  Gly  Leu
     210                     215                     220

Ser  Phe  Asn  Ser  Ile  Ser  Ala  Val  Asp  Asn  Gly  Ser  Leu  Ala  Asn  Thr
225                     230                     235                          240

Pro  His  Leu  Arg  Glu  Leu  His  Leu  Asp  Asn  Asn  Lys  Leu  Thr  Arg  Val
               245                     250                     255

Pro  Gly  Gly  Leu  Ala  Glu  His  Lys  Tyr  Ile  Gln  Val  Val  Tyr  Leu  His
               260                     265                     270

Asn  Asn  Asn  Ile  Ser  Val  Val  Gly  Ser  Arg
               275                     280
```

( 2 ) INFORMATION FOR SEQ ID NO:46:

( i ) SEQUENCE CHARACTERISTICS:
        ( A ) LENGTH: 849 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:46:

```
CTTAAGCTAC  TCCGAAGACC  CTATCCGGGT  CTTCAAGGAC  TACTGGCGCT  GAAGCTCGGG    60
AGGGATCCGG  GTCACACGGG  GAAGGCGACA  GTTACGGTAG  AAGCTCACCA  GGTCACAAGA   120
CTAAACCCAG  ACCTGTTTCA  CGGTTTCCTA  GAAGGGGGAC  TGTGTTGAGA  CGATCTGGAC   180
GTTTTGTTGT  TTTATTGGCT  TTAGTTTCTA  CCTCTGAAAT  TCTTGGACTT  CTTGGAAGTG   240
CGTAACTAAG  AACAGTTGTT  ATTTTAATCG  TTTCAATCAG  GACCTCGTAA  ATGTGGAAAC   300
CACTTCAACC  TTGCTGAAAT  AGACAGGTTC  TTAGTCGACT  TCCTTAACGG  TCTTTTTTAC   360
GGGTTTTGAG  AAGTCCTCGA  CGCACGGGTA  CTCTTACTCT  AGTGGTTTCA  CGCTTTTCAA   420
TGAAAGTTAC  CTGACTTGGT  CTACTAACAG  TATCTTGACC  CGTGGTTAGG  CGACTTCTCG   480
AGTCCTTAAC  TTTTACCCCG  AAAGGTCCCT  TACTTCTTCG  AGAGGATGTA  GGCGTAACGA   540
CTATGGTTAT  AGTGGTCGTA  AGGAGTTCCA  GAAGGAGGAA  GGGAATGCCT  TAATGTAGAA   600
CTACCGTTGT  TTTAGTCGTC  TCAACTACGT  CGATCGGACT  TTCCTGACTT  ATTAAACCGA   660
TTCAACCCTA  ACTCAAAGTT  GTCGTAGAGA  CGACAACTGT  TACCGAGAGA  CCGGTTGTGC   720
GGAGTAGACT  CCCTCGAAGT  GAACCTGTTG  TTGTTCGAAT  GGTCTCATGG  ACCACCCGAC   780
CGTCTCGTAT  TCATGTAGGT  CCAACAGATG  GAAGTATTGT  TGTTATAGAG  ACATCAACCT   840
ATTAGATCT                                                               849
```

( 2 ) INFORMATION FOR SEQ ID NO:47:

( i ) SEQUENCE CHARACTERISTICS:
        ( A ) LENGTH: 924 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
  ( A ) NAME/KEY: CDS
  ( B ) LOCATION: join(1..915, 919..924)

( x i ) SEQUENCE DESCRIPTION: SEQ ID NO:47:

```
GAA TTC GAT GAG GCT TCT GGG ATA GGC CCA GAA GTT CCT GAT GAC CGC          48
Glu Phe Asp Glu Ala Ser Gly Ile Gly Pro Glu Val Pro Asp Asp Arg
  1           5              10                  15

GAC TTC GAG CCC TCC CTA GGC CCA GTG TGC CCC TTC CGC TGT CAA TGC          96
Asp Phe Glu Pro Ser Leu Gly Pro Val Cys Pro Phe Arg Cys Gln Cys
             20              25                  30

CAT CTT CGA GTG GTC CAG TGT TCT GAT TTG GGT CTG GAC AAA GTG CCA         144
His Leu Arg Val Val Gln Cys Ser Asp Leu Gly Leu Asp Lys Val Pro
         35              40                  45

AAG GAT CTT CCC CCT GAC ACA ACT CTG CTA GAC CTG CAA AAC AAC AAA         192
Lys Asp Leu Pro Pro Asp Thr Thr Leu Leu Asp Leu Gln Asn Asn Lys
     50              55                  60

ATA ACC GAA ATC AAA GAT GGA GAC TTT AAG AAC CTG AAG AAC CTT CAC         240
Ile Thr Glu Ile Lys Asp Gly Asp Phe Lys Asn Leu Lys Asn Leu His
 65              70                  75                  80

GCA TTG ATT CTT GTC AAC AAT AAA ATT AGC AAA GTT AGT CCT GGA GCA         288
Ala Leu Ile Leu Val Asn Asn Lys Ile Ser Lys Val Ser Pro Gly Ala
                 85                  90                  95

TTT ACA CCT TTG GTG AAG TTG GAA CGA CTT TAT CTG TCC AAG AAT CAG         336
Phe Thr Pro Leu Val Lys Leu Glu Arg Leu Tyr Leu Ser Lys Asn Gln
            100                 105                 110

CTG AAG GAA TTG CCA GAA AAA ATG CCC AAA ACT CTT CAG GAG CTG CGT         384
Leu Lys Glu Leu Pro Glu Lys Met Pro Lys Thr Leu Gln Glu Leu Arg
        115                 120                 125

GCC CAT GAG AAT GAG ATC ACC AAA GTG CGA AAA GTT ACT TTC AAT GGA         432
Ala His Glu Asn Glu Ile Thr Lys Val Arg Lys Val Thr Phe Asn Gly
    130                 135                 140

CTG AAC CAG ATG ATT GTC ATA GAA CTG GGC ACC AAT CCG CTG AAG AGC         480
Leu Asn Gln Met Ile Val Ile Glu Leu Gly Thr Asn Pro Leu Lys Ser
145                 150                 155                 160

TCA GGA ATT GAA AAT GGG GCT TTC CAG GGA ATG AAG AAG CTC TCC TAC         528
Ser Gly Ile Glu Asn Gly Ala Phe Gln Gly Met Lys Lys Leu Ser Tyr
                165                 170                 175

ATC CGC ATT GCT GAT ACC AAT ATC ACC AGC ATT CCT CAA GGT CTT CCT         576
Ile Arg Ile Ala Asp Thr Asn Ile Thr Ser Ile Pro Gln Gly Leu Pro
            180                 185                 190

CCT TCC CTT ACG GAA TTA CAT CTT GAT GGC AAC AAA ATC AGC AGA GTT         624
Pro Ser Leu Thr Glu Leu His Leu Asp Gly Asn Lys Ile Ser Arg Val
        195                 200                 205

GAT GCA GCT AGC CTG AAA GGA CTG AAT AAT TTG GCT AAG TTG GGA TTG         672
Asp Ala Ala Ser Leu Lys Gly Leu Asn Asn Leu Ala Lys Leu Gly Leu
    210                 215                 220

AGT TTC AAC AGC ATC TCT GCT GTT GAC AAT GGC TCT CTG GCC AAC ACG         720
Ser Phe Asn Ser Ile Ser Ala Val Asp Asn Gly Ser Leu Ala Asn Thr
225                 230                 235                 240

CCT CAT CTG AGG GAG CTT CAC TTG GAC AAC AAC AAG CTT ACC AGA GTA         768
Pro His Leu Arg Glu Leu His Leu Asp Asn Asn Lys Leu Thr Arg Val
                245                 250                 255

CCT GGT GGG CTG GCA GAG CAT AAG TAC ATC CAG GTT GTC TAC CTT CAT         816
Pro Gly Gly Leu Ala Glu His Lys Tyr Ile Gln Val Val Tyr Leu His
            260                 265                 270

AAC AAC AAT ATC TCT GTA GTT GGA TCA AGT GAC TTC TGC CCA CCT GGA         864
Asn Asn Asn Ile Ser Val Val Gly Ser Ser Asp Phe Cys Pro Pro Gly
        275                 280                 285
```

| | | | | | | | | | | | | | | | | |
|---|---|---|---|---|---|---|---|---|---|---|---|---|---|---|---|---|
| CAC | AAC | ACC | AAA | AAG | GCT | TCT | TAT | TCG | GGT | GTG | AGT | CTT | TTC | AGC | AAC | 912 |
| His | Asn | Thr | Lys | Lys | Ala | Ser | Tyr | Ser | Gly | Val | Ser | Leu | Phe | Ser | Asn | |
| | 290 | | | | 295 | | | | | 300 | | | | | | |

| | | | | |
|---|---|---|---|---|
| CCG | TAA | TCT | AGA | 924 |
| Pro | | Ser | Arg | |
| 305 | | | | |

(2) INFORMATION FOR SEQ ID NO:48:

(i) SEQUENCE CHARACTERISTICS:
        (A) LENGTH: 307 amino acids
        (B) TYPE: amino acid
        (D) TOPOLOGY: linear (ii) MOLECULE TYPE: protein (xi) SEQUENCE DESCRIPTION: SEQ ID NO:48:

| | | | | | | | | | | | | | | |
|---|---|---|---|---|---|---|---|---|---|---|---|---|---|---|
| Glu | Phe | Asp | Glu | Ala | Ser | Gly | Ile | Gly | Pro | Glu | Val | Pro | Asp | Asp | Arg |
| 1 | | | | 5 | | | | | 10 | | | | | 15 | |
| Asp | Phe | Glu | Pro | Ser | Leu | Gly | Pro | Val | Cys | Pro | Phe | Arg | Cys | Gln | Cys |
| | | | 20 | | | | | 25 | | | | | 30 | | |
| His | Leu | Arg | Val | Val | Gln | Cys | Ser | Asp | Leu | Gly | Leu | Asp | Lys | Val | Pro |
| | | 35 | | | | | 40 | | | | | 45 | | | |
| Lys | Asp | Leu | Pro | Pro | Asp | Thr | Thr | Leu | Leu | Asp | Leu | Gln | Asn | Asn | Lys |
| | 50 | | | | | 55 | | | | | 60 | | | | |
| Ile | Thr | Glu | Ile | Lys | Asp | Gly | Asp | Phe | Lys | Asn | Leu | Lys | Asn | Leu | His |
| 65 | | | | | 70 | | | | | 75 | | | | | 80 |
| Ala | Leu | Ile | Leu | Val | Asn | Asn | Lys | Ile | Ser | Lys | Val | Ser | Pro | Gly | Ala |
| | | | | 85 | | | | | 90 | | | | | 95 | |
| Phe | Thr | Pro | Leu | Val | Lys | Leu | Glu | Arg | Leu | Tyr | Leu | Ser | Lys | Asn | Gln |
| | | | | 100 | | | | | 105 | | | | | 110 | |
| Leu | Lys | Glu | Leu | Pro | Glu | Lys | Met | Pro | Lys | Thr | Leu | Gln | Glu | Leu | Arg |
| | | 115 | | | | | 120 | | | | | 125 | | | |
| Ala | His | Glu | Asn | Glu | Ile | Thr | Lys | Val | Arg | Lys | Val | Thr | Phe | Asn | Gly |
| | 130 | | | | | 135 | | | | | 140 | | | | |
| Leu | Asn | Gln | Met | Ile | Val | Ile | Glu | Leu | Gly | Thr | Asn | Pro | Leu | Lys | Ser |
| 145 | | | | | 150 | | | | | 155 | | | | | 160 |
| Ser | Gly | Ile | Glu | Asn | Gly | Ala | Phe | Gln | Gly | Met | Lys | Lys | Leu | Ser | Tyr |
| | | | | 165 | | | | | 170 | | | | | 175 | |
| Ile | Arg | Ile | Ala | Asp | Thr | Asn | Ile | Thr | Ser | Ile | Pro | Gln | Gly | Leu | Pro |
| | | | 180 | | | | | 185 | | | | | 190 | | |
| Pro | Ser | Leu | Thr | Glu | Leu | His | Leu | Asp | Gly | Asn | Lys | Ile | Ser | Arg | Val |
| | | | 195 | | | | | 200 | | | | | 205 | | |
| Asp | Ala | Ala | Ser | Leu | Lys | Gly | Leu | Asn | Asn | Leu | Ala | Lys | Leu | Gly | Leu |
| | 210 | | | | | 215 | | | | | 220 | | | | |
| Ser | Phe | Asn | Ser | Ile | Ser | Ala | Val | Asp | Asn | Gly | Ser | Leu | Ala | Asn | Thr |
| 225 | | | | | 230 | | | | | 235 | | | | | 240 |
| Pro | His | Leu | Arg | Glu | Leu | His | Leu | Asp | Asn | Asn | Lys | Leu | Thr | Arg | Val |
| | | | 245 | | | | | 250 | | | | | 255 | | |
| Pro | Gly | Gly | Leu | Ala | Glu | His | Lys | Tyr | Ile | Gln | Val | Val | Tyr | Leu | His |
| | | | 260 | | | | | 265 | | | | | 270 | | |
| Asn | Asn | Asn | Ile | Ser | Val | Val | Gly | Ser | Ser | Asp | Phe | Cys | Pro | Pro | Gly |
| | | 275 | | | | | 280 | | | | | 285 | | | |
| His | Asn | Thr | Lys | Lys | Ala | Ser | Tyr | Ser | Gly | Val | Ser | Leu | Phe | Ser | Asn |
| | 290 | | | | | 295 | | | | | 300 | | | | |
| Pro | Ser | Arg | | | | | | | | | | | | | |
| 305 | | | | | | | | | | | | | | | |

( 2 ) INFORMATION FOR SEQ ID NO:49:

( i ) SEQUENCE CHARACTERISTICS:
    ( A ) LENGTH: 924 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:49:

```
CTTAAGCTAC TCCGAAGACC CTATCCGGGT CTTCAAGGAC TACTGGCGCT GAAGCTCGGG      60
AGGGATCCGG GTCACACGGG GAAGGCGACA GTTACGGTAG AAGCTCACCA GGTCACAAGA     120
CTAAACCCAG ACCTGTTTCA CGGTTTCCTA GAAGGGGGAC TGTGTTGAGA CGATCTGGAC     180
GTTTTGTTGT TTTATTGGCT TTAGTTTCTA CCTCTGAAAT TCTTGGACTT CTTGGAAGTG     240
CGTAACTAAG AACAGTTGTT ATTTAATCG TTTCAATCAG GACCTCGTAA ATGTGGAAAC      300
CACTTCAACC TTGCTGAAAT AGACAGGTTC TTAGTCGACT TCCTTAACGG TCTTTTTTAC     360
GGGTTTTGAG AAGTCCTCGA CGCACGGGTA CTCTTACTCT AGTGGTTTCA CGCTTTTCAA     420
TGAAAGTTAC CTGACTTGGT CTACTAACAG TATCTTGACC CGTGGTTAGG CGACTTCTCG     480
AGTCCTTAAC TTTTACCCCG AAAGGTCCCT TACTTCTTCG AGAGGATGTA GGCGTAACGA     540
CTATGGTTAT AGTGGTCGTA AGGAGTTCCA GAAGGAGGAA GGGAATGCCT TAATGTAGAA     600
CTACCGTTGT TTTAGTCGTC TCAACTACGT CGATCGGACT TTCCTGACTT ATTAAACCGA     660
TTCAACCCTA ACTCAAAGTT GTCGTAGAGA CGACAACTGT TACCGAGAGA CCGGTTGTGC     720
GGAGTAGACT CCCTCGAAGT GAACCTGTTG TTGTTCGAAT GGTCTCATGG ACCACCCGAC     780
CGTCTCGTAT TCATGTAGGT CCAACAGATG GAAGTATTGT TGTTATAGAG ACATCAACCT     840
AGTTCACTGA AGACGGGTGG ACCTGTGTTG TGGTTTTCC GAAGAATAAG CCCACACTCA      900
GAAAAGTCGT TGGGCATTAG ATCT                                           924
```

( 2 ) INFORMATION FOR SEQ ID NO:50:

( i ) SEQUENCE CHARACTERISTICS:
    ( A ) LENGTH: 144 base pairs
    ( B ) TYPE: nucleic acid
    ( C ) STRANDEDNESS: double
    ( D ) TOPOLOGY: linear ( i i ) MOLECULE TYPE: cDNA ( v ) FRAGMENT TYPE: N-terminal ( i x ) FEATURE:
    ( A ) NAME/KEY: CDS
    ( B ) LOCATION: join(1..135, 139..144)

( x i ) SEQUENCE DESCRIPTION: SEQ ID NO:50:

```
GAA TTC GAT GAG GCT TCT GGG ATA GGC CCA GAA GTT CCT GAT GAC CGC       48
Glu Phe Asp Glu Ala Ser Gly Ile Gly Pro Glu Val Pro Asp Asp Arg
  1               5                  10                  15

GAC TTC GAG CCC TCC CTA GGC CCA GTG TCC CCC TTC CGC TCT CAA TCC       96
Asp Phe Glu Pro Ser Leu Gly Pro Val Ser Pro Phe Arg Ser Gln Ser
             20                  25                  30

CAT CTT CGA GTG GTC CAG TCT TCT GAT TTG GGT CTG GAC TAA TCT AGA      144
His Leu Arg Val Val Gln Ser Ser Asp Leu Gly Leu Asp     Ser Arg
         35                  40                  45
```

( 2 ) INFORMATION FOR SEQ ID NO:51:

( i ) SEQUENCE CHARACTERISTICS:
    ( A ) LENGTH: 47 amino acids
    ( B ) TYPE: amino acid
    ( D ) TOPOLOGY: linear ( i i ) MOLECULE TYPE: protein ( x i ) SEQUENCE DESCRIPTION: SEQ ID NO:51:

```
Glu  Phe  Asp  Glu  Ala  Ser  Gly  Ile  Gly  Pro  Glu  Val  Pro  Asp  Asp  Arg
 1                    5                        10                       15

Asp  Phe  Glu  Pro  Ser  Leu  Gly  Pro  Val  Ser  Pro  Phe  Arg  Ser  Gln  Ser
               20                        25                        30

His  Leu  Arg  Val  Val  Gln  Ser  Ser  Asp  Leu  Gly  Leu  Asp  Ser  Arg
               35                        40                        45
```

( 2 ) INFORMATION FOR SEQ ID NO:52:

( i ) SEQUENCE CHARACTERISTICS:
    ( A ) LENGTH: 144 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:52:

```
CTTAAGCTAC  TCCGAAGACC  CTATCCGGGT  CTTCAAGGAC  TACTGGCGCT  GAAGCTCGGG      60

AGGGATCCGG  GTCACAGGGG  GAAGGCGAGA  GTTAGGGTAG  AAGCTCACCA  GGTCAGAAGA     120

CTAAACCCAG  ACCTGATTAG  ATCT                                              144
```

( 2 ) INFORMATION FOR SEQ ID NO:53:

( i ) SEQUENCE CHARACTERISTICS:
    ( A ) LENGTH: 144 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: CDS
    ( B ) LOCATION: join(1..135, 139..144)

( x i ) SEQUENCE DESCRIPTION: SEQ ID NO:53:

```
GAA  TTC  GAT  GAG  GCT  TCT  GGG  ATA  GGC  CCA  GAA  GTT  CCT  GAT  GAC  CGC    48
Glu  Phe  Asp  Glu  Ala  Ser  Gly  Ile  Gly  Pro  Glu  Val  Pro  Asp  Asp  Arg
 1                    5                        10                       15

GAC  TTC  GAG  CCC  TCC  CTA  GGC  CCA  GTG  TGC  CCC  TTC  CGC  TCT  CAA  TCC    96
Asp  Phe  Glu  Pro  Ser  Leu  Gly  Pro  Val  Cys  Pro  Phe  Arg  Ser  Gln  Ser
               20                        25                        30

CAT  CTT  CGA  GTG  GTC  CAG  TGT  TCT  GAT  TTG  GGT  CTG  GAC  TAA  TCT  AGA   144
His  Leu  Arg  Val  Val  Gln  Cys  Ser  Asp  Leu  Gly  Leu  Asp       Ser  Arg
               35                        40                   45
```

( 2 ) INFORMATION FOR SEQ ID NO:54:

( i ) SEQUENCE CHARACTERISTICS:
    ( A ) LENGTH: 47 amino acids
    ( B ) TYPE: amino acid
    ( D ) TOPOLOGY: linear ( i i ) MOLECULE TYPE: protein ( x i ) SEQUENCE DESCRIPTION: SEQ ID NO:54:

```
Glu  Phe  Asp  Glu  Ala  Ser  Gly  Ile  Gly  Pro  Glu  Val  Pro  Asp  Asp  Arg
 1                    5                        10                       15
```

```
Asp Phe Glu Pro Ser Leu Gly Pro Val Cys Pro Phe Arg Ser Gln Ser
            20                  25                  30

His Leu Arg Val Val Gln Cys Ser Asp Leu Gly Leu Asp Ser Arg
            35                  40                  45
```

( 2 ) INFORMATION FOR SEQ ID NO:55:

( i ) SEQUENCE CHARACTERISTICS:
        ( A ) LENGTH: 144 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:55:

```
CTTAAGCTAC TCCGAAGACC CTATCCGGGT CTTCAAGGAC TACTGGCGCT GAAGCTCGGG      60

AGGGATCCGG GTCACACGGG GAAGGCGAGA GTTAGGGTAG AAGCTCACCA GGTCACAAGA     120

CTAAACCCAG ACCTGATTAG ATCT                                            144
```

( 2 ) INFORMATION FOR SEQ ID NO:56:

( i ) SEQUENCE CHARACTERISTICS:
        ( A ) LENGTH: 168 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: join(1..159, 163..168)

( x i ) SEQUENCE DESCRIPTION: SEQ ID NO:56:

```
GAA TTC TCA AGT GAC TTC TGC CCA CCT GGA CAC AAC ACC AAA AAG GCT       48
Glu Phe Ser Ser Asp Phe Cys Pro Pro Gly His Asn Thr Lys Lys Ala
 1               5                  10                  15

TCT TAT TCG GGT GTG AGT CTT TTC AGC AAC CCG GTC CAG TAC TGG GAG       96
Ser Tyr Ser Gly Val Ser Leu Phe Ser Asn Pro Val Gln Tyr Trp Glu
            20                  25                  30

ATA CAG CCA TCC ACC TTC AGA TGT GTC TAC GTG CGC TCT GCC ATT CAA      144
Ile Gln Pro Ser Thr Phe Arg Cys Val Tyr Val Arg Ser Ala Ile Gln
            35                  40                  45

CTC GGA AAC TAT AAG TAA TCT AGA                                      168
Leu Gly Asn Tyr Lys     Ser Arg
            50                  55
```

( 2 ) INFORMATION FOR SEQ ID NO:57:

( i ) SEQUENCE CHARACTERISTICS:
        ( A ) LENGTH: 55 amino acids
        ( B ) TYPE: amino acid
        ( D ) TOPOLOGY: linear ( i i ) MOLECULE TYPE: protein ( x i ) SEQUENCE DESCRIPTION: SEQ ID NO:57:

```
Glu Phe Ser Ser Asp Phe Cys Pro Pro Gly His Asn Thr Lys Lys Ala
 1               5                  10                  15

Ser Tyr Ser Gly Val Ser Leu Phe Ser Asn Pro Val Gln Tyr Trp Glu
            20                  25                  30

Ile Gln Pro Ser Thr Phe Arg Cys Val Tyr Val Arg Ser Ala Ile Gln
            35                  40                  45
```

```
Leu Gly Asn Tyr Lys Ser Arg
    50                  55
```

( 2 ) INFORMATION FOR SEQ ID NO:58:

( i ) SEQUENCE CHARACTERISTICS:
        ( A ) LENGTH: 168 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:58:

```
CTTAAGAGTT CACTGAAGAC GGGTGGACCT GTGTTGTGGT TTTTCCGAAG AATAAGCCCA    60

CACTCAGAAA AGTCGTTGGG CCAGGTCATG ACCCTCTATG TCGGTAGGTG GAAGTCTACA   120

CAGATGCACG CGAGACGGTA AGTTGAGCCT TTGATATTCA TTAGATCT                168
```

( 2 ) INFORMATION FOR SEQ ID NO:59:

( i ) SEQUENCE CHARACTERISTICS:
        ( A ) LENGTH: 168 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: join(1..159, 163..168)

( x i ) SEQUENCE DESCRIPTION: SEQ ID NO:59:

```
GAA TTC TCA AGT GAC TTC TCC CCA CCT GGA CAC AAC ACC AAA AAG GCT     48
Glu Phe Ser Ser Asp Phe Ser Pro Pro Gly His Asn Thr Lys Lys Ala
 1               5                  10                  15

TCT TAT TCG GGT GTG AGT CTT TTC AGC AAC CCG GTC CAG TAC TGG GAG     96
Ser Tyr Ser Gly Val Ser Leu Phe Ser Asn Pro Val Gln Tyr Trp Glu
             20                  25                  30

ATA CAG CCA TCC ACC TTC AGA TGT GTC TAC GTG CGC TCT GCC ATT CAA    144
Ile Gln Pro Ser Thr Phe Arg Cys Val Tyr Val Arg Ser Ala Ile Gln
         35                  40                  45

CTC GGA AAC TAT AAG TAA TCT AGA                                    168
Leu Gly Asn Tyr Lys     Ser Arg
     50                      55
```

( 2 ) INFORMATION FOR SEQ ID NO:60:

( i ) SEQUENCE CHARACTERISTICS:
        ( A ) LENGTH: 55 amino acids
        ( B ) TYPE: amino acid
        ( D ) TOPOLOGY: linear ( i i ) MOLECULE TYPE: protein ( x i ) SEQUENCE DESCRIPTION: SEQ ID NO:60:

```
Glu Phe Ser Ser Asp Phe Ser Pro Pro Gly His Asn Thr Lys Lys Ala
 1               5                  10                  15

Ser Tyr Ser Gly Val Ser Leu Phe Ser Asn Pro Val Gln Tyr Trp Glu
             20                  25                  30

Ile Gln Pro Ser Thr Phe Arg Cys Val Tyr Val Arg Ser Ala Ile Gln
         35                  40                  45

Leu Gly Asn Tyr Lys Ser Arg
     50                  55
```

(2) INFORMATION FOR SEQ ID NO:61:

(i) SEQUENCE CHARACTERISTICS:
    (A) LENGTH: 168 base pairs
    (B) TYPE: nucleic acid
    (C) STRANDEDNESS: double
    (D) TOPOLOGY: linear (ii) MOLECULE TYPE: cDNA (xi) SEQUENCE DESCRIPTION: SEQ ID NO:61:

```
CTTAAGAGTT  CACTGAAGAG  GGGTGGACCT  GTGTTGTGGT  TTTTCCGAAG  AATAAGCCCA      60

CACTCAGAAA  AGTCGTTGGG  CCAGGTCATG  ACCCTCTATG  TCGGTAGGTG  GAAGTCTACA     120

CAGATGCACG  CGAGACGGTA  AGTTGAGCCT  TTGATATTCA  TTAGATCT                   168
```

(2) INFORMATION FOR SEQ ID NO:62:

(i) SEQUENCE CHARACTERISTICS:
    (A) LENGTH: 6 amino acids
    (B) TYPE: amino acid
    (D) TOPOLOGY: linear (ii) MOLECULE TYPE: protein (xi) SEQUENCE DESCRIPTION: SEQ ID NO:62:

```
His  Leu  Arg  Val  Val  Gln
 1                 5
```

DECORIN FRAGMENTS INHIBITING CELL REGULATORY FACTORS

This application is a continuation of application Ser. No. 07/865,652, filed Apr. 3, 1992, now abandoned which is a continuation-in-part of application Ser. No. 07/792,192, filed Nov. 14, 1991, now abandoned which is a continuation-in-part of Ser. No. 07/467,888, filed Jan. 22, 1990, now abandoned which is a continuation-in-part of Ser. No. 07/212,702, filed Jun. 28, 1988.

This invention was made with support of government grants CA 30199, CA 42507 and CA 28896 from the National Cancer Institute. Therefore, the United States government may have certain rights in the invention.

FIELD OF THE INVENTION

This invention relates to cell biology and more specifically to the control of cell proliferation by inhibiting cell regulatory factors.

BACKGROUND OF THE INVENTION

Proteoglycans are proteins that carry one or more glycosaminoglycan chains. The known proteoglycans carry out a wide variety of functions and are found in a variety of cellular locations. Many proteoglycans are components of extracellular matrix, where they participate in the assembly of cells and effect the attachment of cells to the matrix.

Decorin, also known as PG-II or PG-40, is a small proteoglycan produced by fibroblasts. Its core protein has a molecular weight of about 40,000 daltons. The core has been sequenced (Krusius and Ruoslahti, Proc. Natl. Acad. Sci. USA 83:7683 (1986); Day et al. Biochem. J. 248:801 (1987), both of which are incorporated herein by reference) and it is known to carry a single glycosaminoglycan chain of a chondroitin sulfate/dermatan sulfate type (Pearson, et al., J. Biol. Chem. 258:15101 (1983), which is incorporated herein by reference). The only previously known function for decorin is binding to type I and type II collagen and its effect on the fibril formation by these collagens (Vogel, et al., Biochem. J. 223:587 (1984); Schmidt et al., J. Cell Biol. 104:1683, (1987)). Two proteoglycans, biglycan (Fisher et al., J. Biol. Chem. 264:4571 (1989)) and fibromodulin, (Oldberg et al., EMBO J. 8:2601, (1989) have core proteins the amino acid sequences of which are closely related to that of decorin and they, together with decorin, can be considered a protein family. Each of their sequences is characterized by the presence of a leucine-rich repeat of about 24 amino acids. Several other proteins contain similar repeats. Together all of these proteins form a superfamily of proteins (Ruoslahti, Ann. Rev. Cell Biol. 4:229, (1988); McFarland et al., Science 245:494 (1989)).

Transforming growth factor β's (TGFβ) are a family of multi-functional cell regulatory factors produced in various forms by many types of cells (for review see Sporn et al., J. Cell Biol. 105:1039, (1987)). Five different TGFβ's are known, but the functions of only two, TGFβ-1 and TGFβ-2, have been characterized in any detail. TGFβ's are the subject of U.S. Pat. Nos. 4,863,899; 4,816,561; and 4,742,003 which are incorporated by reference. TGFβ-1 and TGFβ-2 are publicly available through many commercial sources (e.g. R & D Systems, Inc., Minneapolis, Minn.). These two proteins have similar functions and will be here collectively referred to as TGFβ. TGFβ binds to cell surface receptors possessed by essentially all types of cells, causing profound changes in them. In some cells, TGFβ promotes cell proliferation, in others it suppresses proliferation. A marked effect of TGFβ is that it promotes the production of extracellular matrix proteins and their receptors by cells (for review see Keski-Oja et al., J. Cell Biochem 33:95 (1987); Massague, Cell 49:437 (1987); Roberts and Sporn in "Peptides Growth Factors and Their Receptors" (Springer-Verlag, Heidelberg (1989)).

While TGFβ has many essential cell regulatory functions, improper TGFβ activity can be detrimental to an organism. Since the growth of mesenchyme and proliferation of mesenchymal cells is stimulated by TGFβ, some tumor cells may use TGFβ as an autocrine growth factor. Therefore, if the growth factor activity of TGFβ could be prevented, tumor growth could be controlled. In other cases the inhibition of cell proliferation by TGFβ may be detrimental, in that it may prevent healing of injured tissues. The stimulation of extracellular matrix production by TGFβ is important in situations such as wound healing. However, in some cases the body takes this response too far and an excessive accumulation of extracellular matrix ensues. An example of excessive accumulation of extracellular matrix is glomerulonephritis, a disease with a detrimental involvement of TGFβ.

Thus, a need exists to develop compounds that can modulate the effects of cell regulatory factors such as TGFβ. The present invention satisfies this need and provides related advantages.

SUMMARY OF THE INVENTION

The present invention provides active fragments of proteins having a cell regulatory factor binding domain. The invention further provides a method of inhibiting an activity of a cell regulatory factor comprising contacting the cell regulatory factor with a purified polypeptide, wherein the polypeptide comprises a cell regulatory factor binding domain of a protein and wherein the protein is characterized by a leucine-rich repeat of about 24 amino acids. In a specific embodiment, the present invention relates to the ability of decorin, a 40,000 dalton protein that usually carries a glycosaminoglycan chain, and more specifically to active fragments of decorin or a functional equivalent of decorin to bind TGFβ or other cell regulatory factors. The invention also provides a novel cell regulatory factor designated Morphology Restoring Factor, (MRF). Also provided are methods of identifying, detecting and purifying cell regulatory factors and proteins that bind and affect the activity of cell regulatory factors.

BRIEF DESCRIPTION OF THE FIGURES

(FIG. 2A) Fractionation of [$^{125}$I]-TGFβ1 to decorin-Sepharose affinity chromatography. [$^{125}$I] TGFβ1 (5×10$^5$ cpm) was incubated in BSA-coated polypropylene tubes with 0.2 ml of packed decorin-Sepharose (○) or gelatin-Sepharose (●) in 2 ml of PBS pH 7.4, containing 1M NaCl and 0.05% Tween 20. After overnight incubation, the affinity matrices were transferred into BSA-coated disposable columns (Bio Rad) and washed with the binding buffer. Elution was effected first with 3M NaCl in the binding buffer and then with 8M urea in the same buffer: (FIG. 2B) Analysis of eluents of decorin-Sepharose affinity chromatography by SDS-polyacrylamide gel under nonreducing conditions. Lane 1: the original [$^{125}$I]-labeled TGFβ1 sample; lanes 2–7: flow through and wash fractions; lanes 8–10: 3M NaCl fractions; lanes 11–14: 8M urea fractions. Arrows indicate the top and bottom of the 12% separating gel.

FIGS. 3A and 3B show the inhibition of binding of [$^{125}$I]TGFβ1 to decorin by proteoglycans and their core proteins: (FIG. 3A) Competition of [$^{125}$I]TGFβ1 binding to decorin-coated microtiter wells by recombinant decorin (●), decorin isolated from bovine skin (PGII) (■), biglycan isolated from bovine articular cartilage (PGI) (◐), chicken cartilage proteoglycan (○), and BSA (□). Each point represents the mean of duplicate determinants. (FIG 3B) Competition of [$^{125}$I]TGFβ1 binding with chondroitinase ABC-treated proteoglycans and BSA. The concentrations of competitors were expressed as intact proteoglycan. The symbols are the same as in FIG. 3A.

FIGS. 4A and 4B show neutralization of the growth regulating activity of TGFβ1 by decorin: (FIG. 4A) Shows inhibition of TGFβ1-induced proliferation of CHO cells by decorin. [$^3$H]Thymidine incorporation assay was performed in the presence of 5 ng/ml of TGFβ-1 and the indicated concentrations of purified decorin (○) or BSA (●). At the concentration used, TGFβ-1 induced a 50% increase of [$^3$H]thymidine incorporation in the CHO cells. The data represent percent neutralization of this growth stimulation; i.e. [$^3$H]thymidine incorporation in the absence of either TGFβ1 or decorin=0%, incorporation in the presence of TGFβ but not decorin=100%. Each point shows the mean ± standard deviation of triplicate samples. (FIG. 4B) Shows neutralization of TGFβ1-induced growth inhibition in Mv1Lu cells by decorin. The assay was performed as in A except that TGFβ-1 was added at 0.5 ng/ml. This concentration of TGFβ-1 induces 50% reduction of [$^3$H]thymidine incorporation in the Mv1Lu cells. The data represent neutralization of TGFβ-induced growth inhibition; i.e. [$^3$H] thymidine incorporation in the presence of neither TGFβ or decorin=100%; incorporation in the presence of TGFβ but not decorin=0%.

DETAILED DESCRIPTION OF THE INVENTION

Figure 1A:
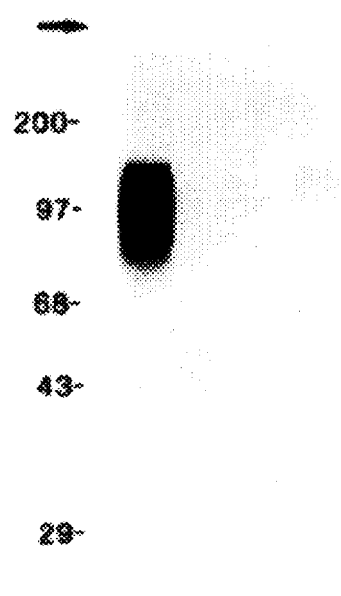
FIGS. 1A and 1B show expression of decorin cDNA containing a mutation of the serine acceptor site to alanine. COS-1 cultures were transfected with cDNA coding for wild-type decorin (lane 1), decorin in which the serine-4 residue was replaced by an alanine (lane 2), or decorin in which the serine-4 residue was replaced by a threonine (lane 3). Immunoprecipitations were performed with an anti-decorin antibody and medium which was labeled with $^{35}$S-sulfate (A) or -$^{3}$H-leucine (B). Lane 4 shows an immunoprecipitate from mock transfected COS-1 cultures. Arrow indicates top of gel. The numbers indicate $M_r \times 10^{-3}$ for molecular weight standards.

The invention provides a method of inhibiting an activity of a cell regulatory factor comprising contacting the cell regulatory factor with a purified polypeptide, wherein the polypeptide comprises the cell regulatory factor binding domain of a protein. The protein can be characterized by a leucine-rich repeat of about 24 amino acids. Since diseases such as cancer result from uncontrolled cell proliferation, the invention can be used to treat such diseases.

By "cell regulatory factor" is meant a molecule which can regulate an activity of a cell. The cell regulatory factors are generally proteins which bind cell surface receptors and include growth factors. Examples of cell regulatory factors include the five TGFβ's, platelet-derived growth factor (PDGF), epidermal growth factor, insulin like growth factor I and II, fibroblast growth factor, interleukin-2, nerve growth factor, hemopoietic cell growth factors (IL-3, GM-CSF, M-CSF, G-CSF, erythropoietin) and the newly discovered Morphology Restoring Factor, hereinafter "MRF". Different regulatory factors can be bound by different proteins which can affect the regulatory factor's activity. For example, TGFβ-1 is bound by decorin and biglycan, and MRF by decorin.

By "cell regulatory factor binding domain" is meant a fragment of a protein which binds to the cell regulatory factor. A protein fragment that retains the binding activity is included within the scope of the invention and is referred to herein as an active fragment. Fragments that retain such activity, such as active fragments of decorin or biglycan, can be recognized by their ability to competitively inhibit the binding of, for example, decorin to TGFβ, or of other polypeptides to their cognate growth factors.

Active fragments can be obtained by proteolytic digestion of the native polypeptide according to methods known in the art or as described, for example, in Example VIII. Alternatively, active fragments can be synthesized based on the known amino acid sequence by methods known to those skilled in the art or as described in Example VIII. The fragments can also be produced recombinantly by methods known in the art or as described in Example V. Examples of active fragments are included in Tables 4–15.

Such fragments can then be used in a competitive assay to determine whether they retain binding activity. For example, decorin can be attached to an affinity matrix, as by the method of Example II. Labelled TGFβ and an active fragment can then be contacted with the affinity matrix and the amount of TGFβ bound thereto determined.

As used herein, "decorin" refers to a proteoglycan having substantially the structural characteristics attributed to it in Krusius and Ruoslahti, supra. Human fibroblast decorin has substantially the amino acid sequence presented in Krusius and Ruoslahti, supra. "Decorin" refers both to the native composition and to modifications thereof which substantially retain the functional characteristics. Decorin core protein refers to decorin that no longer is substantially substituted with glycosaminoglycan and is included in the definition of decorin. Decorin can be rendered glycosaminoglycan-free by mutation or other means, such as by producing recombinant decorin in cells incapable of attaching glycosaminoglycan chains to a core protein.

Functional equivalents of decorin include modifications of decorin that retain its functional characteristics and molecules that are homologous to decorin, such as the decorin family members biglycan and fibromodulin, for example, that have the similar functional activity of decorin. Modifications can include, for example, the addition of one or more side chains that do not interfere with the functional activity of the decorin core protein.

Since the regulatory factor binding proteins each contain leucine-rich repeats of about 24 amino acids which can constitute 80% of the protein, it is likely that the fragments which retain the binding activity occur in the leucine-rich repeats. However, it is possible the binding activity resides elsewhere such as in the carboxy terminal amino acids or the junction of the repeats and the carboxy terminal amino acids.

The invention teaches a general method whereby one skilled in the art can identify proteins that can bind to cell regulatory factors or identify cell regulatory factors that bind to a certain family of proteins. The invention also teaches a general method in which these novel proteins or known existing proteins can be assayed to determine if they affect an activity of a cell regulatory factor. Specifically, the invention teaches the discovery that decorin and biglycan bind TGFβ-1 and MRF and that such binding can inhibit the cell regulatory functions of TGFβ-1. Further, both decorin and biglycan are about 80% homologous and contain a leucine-rich repeat of about 24 amino acids in which the arrangement of the leucine residues is conserved. As defined, each repeat generally contains at least two leucine residues and can contain five or more. These proteoglycans are thus considered members of the same protein family. See Ruoslahti, supra, Fisher et al., J. Biol. Chem., 264:4571–4576 (1989) and Patthy, J. Mol. Biol., 198:567–577 (1987), all of which are incorporated by reference. Other known or later discovered proteins having this leucine-rich repeat, i.e., fibromodulin, would be expected to have a similar cell regulatory activity. The ability of such proteins to bind cell regulatory factors could easily be tested, for example by affinity chromatography or microtiter assay as set forth in Example II, using known cell regulatory factors, such as TGFβ-1. Alternatively, any later discovered cell regulatory factor could be tested, for example by affinity chromatography using one or more regulatory factor binding proteins. Once it is determined that such binding occurs, the effect of the binding on the activity of all regulatory factors can be determined by methods such as growth assays as set forth in Example III. Moreover, one skilled in the art could simply substitute a novel cell regulatory factor for TGFβ-1 or a novel leucine-rich repeat protein for decorin or biglycan in the Examples to determine their activities. Thus, the invention provides general methods to identify and test novel cell regulatory factors and proteins which affect the activity of these factors.

The invention also provides a novel purified compound comprising a cell regulatory factor attached to a purified polypeptide wherein the polypeptide comprises the cell regulatory factor binding domain of a protein and the protein is characterized by a leucine-rich repeat of about 24 amino acids.

The invention further provides a novel purified protein, designated MRF, having a molecular weight of about 20 kd, which can be isolated from CHO cells, copurifies with decorin under nondissociating conditions, separates from decorin under dissociating conditions, changes the morphology of transformed 3T3 cells, and has an activity which is not inhibited with anti-TGFβ-1 antibody. Additionally, MRF separates from TGFβ-1 in HPLC.

The invention still further provides a method of purifying a cell regulatory factor comprising contacting the regulatory factor with a protein which binds the cell regulatory factor and has a leucine-rich repeat of about 24 amino acids and to purify the regulatory factor which becomes bound to the protein. The method can be used, for example, to purify TGFβ-1 by using decorin.

The invention additionally provides a method of treating a pathology caused by a TGFβ-regulated activity comprising contacting the TGFβ with a purified polypeptide, wherein the polypeptide comprises the TGFβ binding domain of a protein and wherein the protein is characterized by a leucine-rich repeat of about 24 amino acids, whereby the pathology-causing activity is prevented or reduced. While the method is generally applicable, specific examples of pathologies which can be treated include a cancer, a fibrotic disease, and glomerulonephritis. In cancer, for example, decorin can be used to bind TGFβ-1, destroying TGFβ-1's growth stimulating activity on the cancer cell.

Finally, a method of preventing the inhibition of a cell regulatory factor is provided. The method comprises contacting a protein which inhibits an activity of a cell regulator factor with a molecule which inhibits the activity of the protein. For example, decorin could be bound by a molecule, such as an antibody, which prevents decorin from binding TGFβ-1, thus preventing decorin from inhibiting the TGFβ-1 activity. Thus, the TGFβ-1 wound healing activity could be promoted by binding TGFβ-1 inhibitors.

It is understood that modifications which do not substantially affect the activity of the various molecules of this invention including TGFβ, MRF, decorin, biglycan and fibromodulin are also included within the definition of those molecules. It is also understood that the core proteins of decorin, biglycan and fibromodulin are also included within the definition of those molecules.

The following examples are intended to illustrate but not limit the invention.

EXAMPLE I

EXPRESSION AND PURIFICATION OF RECOMBINANT DECORIN AND DECORIN CORE PROTEIN

Expression system

The 1.8 kb full-length decorin cDNA described in Krusius and Ruoslahti, Proc. Natl. Acad. Sci. USA 83:7683 (1986), which is incorporated herein by reference, was used for the construction of decorin expression vectors. For the expression of decorin core protein, cDNA was mutagenized so the fourth codon, TCT, coding for serine, was changed to ACT coding for threonine, or GCT coding for alanine. This was engineered by site-directed mutagenesis according to the method of Kunkel, Proc. Natl. Acad. Sci USA 82:488 (1985), which is incorporated herein by reference. The presence of the appropriate mutation was verified by DNA sequencing.

The mammalian expression vectors pSV2-decorin and pSV2-decorin/CP-thr4 core protein were constructed by ligating the decorin cDNA or the mutagenized decorin cDNA into 3.4 kb HindIII-Bam HI fragment of pSV2 (Mulligan and Berg, Science 209:1423 (1980), which is incorporated herein by reference).

Dihydrofolate reductase (dhfr)-negative CHO cells (CHO-DG44) were cotransfected with pSV2-decorin or pSV2-decorin/CP and pSV2dhfr by the calcium phosphate coprecipitation method. The CHO-DG44 cells transfected with pSV2-decorin are deposited with the American Type Culture Collection under Accession Number ATCC No. CRL 10332. The transfected cells were cultured in nucleoside-minus alpha-modified minimal essential medium (α-MEM), (GIBCO, Long Island) supplemented with 9% dialyzed fetal calf serum, 2 mM glutamine, 100 units/ml penicillin and 100 µg/ml streptomycin. Colonies arising from transfected cells were picked using cloning cylinders, expanded and checked for the expression of decorin by immunoprecipitation from $^{35}SO_4$-labeled culture supernatants. Clones expressing a substantial amount of decorin were then subjected to gene amplification by stepwise increasing concentration of methotrexate (MTX) up to 0.64 µM (Kaufman and Sharp, J. Mol. Biol. 159:601 (1982), which is incorporated herein by reference). All the amplified cell lines were cloned either by limiting dilution or by picking single MTX resistant colonies. Stock cultures of these established cell lines were kept in MTX-containing medium. Before use in protein production, cells were subcultured in MTX-minus medium from stock cultures and passed at least once in this medium to eliminate the possible MTX effects.

Alternatively, the core protein was expressed in COS-1 cells as described in Adams and Rose, Cell 41:1007, (1985), which is incorporated herein by reference. Briefly, 6-well multiwell plates were seeded with $3–5 \times 10^5$ cells per 9.6 cm² growth area and allowed to attach and grow for 24 hours. Cultures were transfected with plasmid DNA when they were 50–70% confluent. Cell layers were washed briefly with Tris buffered saline (TBS) containing 50 mM Tris, 150 mM NaCl pH 7.2, supplemented with 1 mM CaCl and 0.5 mM $MgCl_2$ at 37° C. to prevent detachment. The wells were incubated for 30 minutes at 37° C. with 1 ml of the above solution containing 2 µg of closed circular plasmid DNA and 0.5 mg/ml DEAE-Dextran (Sigma) of average molecular mass of 500,000. As a control, cultures were transfected with the pSV2 expression plasmid lacking any decorin insert or mock transfected with no DNA. Culture were then incubated for 3 hours at 37° C. with Dulbecco's Modified Eagle's medium (Irvine Scientific) containing 10% fetal calf serum and 100 µM chloroquine (Sigma), after removing the DNA/TBS/DEAE-Dextran solution and rinsing the wells with TBS. The cell layers were then rinsed twice and cultured in the above medium, lacking any chloroquine, for approximately 36 hours. WI38 human embryonic lung fibroblasts were routinely cultured in the same medium.

COS-1 cultures were radiolabeled 36–48 hours after transfection with the plasmid DNAs. All radiolabeled metabolic precursors were purchased from New England Nuclear (Boston, Mass.). The isotopes used were $^{35}$S-sulfate (460 mCi/ml), L-[3,4,5-$^3$H(N)]-leucine (140 Ci/ml) and L-[$^{14}$C (U) ]—amino acid mixture (product number 445E). Cultures were labeled for 24 hours in Ham's F-12 medium (GIBCO Labs), supplemented with 10% dialyzed fetal calf serum, 2 mM glutamine and 1 mM pyruvic acid, and containing 200 µCi/ml $^{35}$S-sulfate or $^3$H-leucine, or 10 µCi/ml of the $^{14}$C-amino acid mixture. The medium was collected, supplemented with 5 mM EDTA, 0.5 mM phenylmethylsulfonylfluoride, 0.04 mg/ml aprotinin and 1 µg/ml pepstatin to inhibit protease activity, freed of cellular debris by centrifugation for 20 minutes at 2,000 ×G and stored at -20° C. Cell extracts were prepared by rinsing the cell layers with TBS and then scraping with a rubber policeman into 1 ml/well of ice cold cell lysis buffer: 0.05M Tris-HCl, 0.5M NaCl 0.1% BSA, 1% NP-40, 0.5% Triton X-100, 0.1% SDS, pH 8.3. The cell extracts were clarified by centrifugation for 1.5 hours at 13,000×G at 4° C.

Rabbit antiserum was prepared against a synthetic peptide based on the first 15 residues of the mature form of the human decorin core protein (Asp-Glu-Ala-Ser-Gly-Ile-Gly-Pro-Glu-Val-Pro-Asp-Asp-Arg-Asp(SEQ ID No. 1)). The synthetic peptide and the antiserum against it have been described elsewhere (Krusius and Ruoslahti, 1986 supra.) Briefly, the peptide was synthesized with a solid phase peptide synthesizer (Applied Biosystems, Foster City, Calif.) by using the chemistry suggested by the manufacturer. The peptide was coupled to keyhole limpet hemocyanin by using N-succinimidyl 3-(2-pyridyldithio) propionate (Pharmacia Fine Chemicals, Piscataway, N.J.) according to the manufacturer's instructions. The resulting conjugates were emulsified in Freund's complete adjuvant and injected into rabbits. Further injections of conjugate in Freund's incomplete adjuvant were given after one, two and three months. The dose of each injection was equivalent to 0.6 mg of peptide. Blood was collected 10 days after the third and fourth injection. The antisera were tested against the glutaraldehyde-cross linked peptides and isolated decorin in ELISA (Engvall, Meth. Enzymol. 70:419–439 (1980)), in immunoprecipitation and immunoblotting, and by staining cells in immunofluorescence, as is well known in the art.

Immunoprecipitations were performed by adding 20 µl of antiserum to the conditioned medium or cell extract collected from duplicate wells and then mixing overnight at 4° C. Immunocomplexes were isolated by incubations for 2 hours at 4° C. with 20 µl of packed Protein A-agarose (Sigma). The beads were washed with the cell lysis buffer, with three tube changes, and then washed twice with phosphate-buffered saline prior to boiling in gel electrophoresis sample buffer containing 10% mercaptoethanol. Immunoprecipitated proteins were separated by SDS-PAGE in 7.5–20% gradient gels or 7.5% non-gradient gels as is well known in the art. Fluorography was performed by using Enlightning (New England Nuclear) with intensification screens. Typical exposure times were for 7–10 days at –70° C. Autoradiographs were scanned with an LKB Ultroscan XL Enhanced Laser Densitometer to compare the relative intensities and mobilities of the proteoglycan bands.

SDS-PAGE analysis of cell extracts and culture medium from COS-1 cells transfected with the decorin-pSV2 construct and metabolically radiolabeled with $^{35}$S-sulfate revealed a sulfated band that was not present in mock-transfected cells. Immunoprecipitation with the antiserum raised against a synthetic peptide derived from the decorin core protein showed that the new band was decorin.

Expression of the construct mutated such that the serine residue which is normally substituted with a glycosaminoglycan (serine-4) was replaced by a threonine residue by SDS-PAGE revealed only about 10% of the level of proteoglycan obtained with the wild-type construct. The rest of the immunoreactive material migrated at the position of free core protein.

Figure 1B:
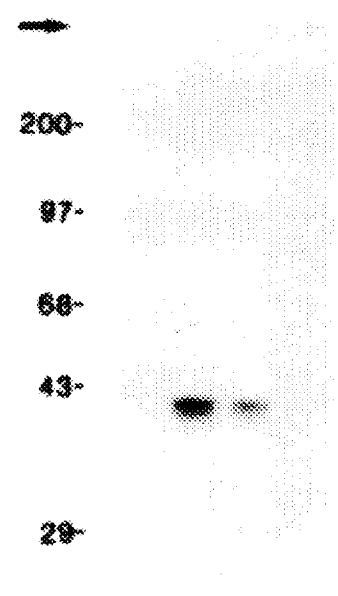

The alanine-mutated cDNA construct when expressed and analyzed in a similar manner yielded only core protein and no proteoglycan form of decorin. FIGS. 1A and 1B show the expression of decorin (lanes 1) and its threonine-4 (lanes 3) and alanine-4 (lanes 2) mutated core proteins expressed in COS cell transfectants. $^{35}SO_4$-labeled (FIG. 1A) and $^3$H-leucine labeled (FIG. 1 and B) culture supernatants were immunoprecipitated with rabbit antipeptide antiserum prepared against the $NH_2$-terminus of human decorin.

Purification of Decorin and Decorin Core Protein from Spent Culture Media

Cells transfected with pSV2-decorin vector and amplified as described above and in Yamaguchi and Ruoslahti, Nature 36:244-246 (1988), which is incorporated herein by reference, were grown to 90% confluence in eight culture flasks (175 cm$^2$) in nucleoside minus α-MEM supplemented with 9% dialyzed fetal calf serum, 2 mM glutamine, 100 units/ml penicillin and 100 µg/ml streptomycin. At 90% confluence culture media was changed to 25 ml per flask of nucleoside-free α-MEM supplemented with 6% dialyzed fetal calf serum which had been passed through a DEAE Sepharose Fast Flow column (Pharmacia) equilibrated with 0.25M NaCl in 0.05M phosphate buffer, pH 7.4. Cells were cultured for 3 days, spent media was collected and immediately made to 0.5 mM phenylmethylsulfonyl fluoride, 1 µg/ml pepstatin, 0.04 mg/ml aprotinin and 5 mM EDTA.

Four hundred milliliters of the spent media were first passed through gelatin-Sepharose to remove fibronectin and materials which would bind to Sepharose. The flow-through fraction was then mixed with DEAE-Sepharose preequilibrated in 50 mM Tris/HCl, pH 7.4, plus 0.2M NaCl and batch absorbed overnight at 4° C. with gentle mixing. The slurry was poured into a 1.6×24 cm column, washed extensively with 50 mM Tris/HCl, pH 7.4, containing 0.2M NaCl and eluted with 0.2M-0.8M linear gradient of NaCl in 50 mM Tris/HCl pH 7.4. Decorin concentration was determined by competitive ELISA as described in Yamaguchi and Ruoslahti, supra. The fractions containing decorin were pooled and further fractionated on a Sephadex gel filtration column equilibrated with 8M urea in the Tris-HCl buffer. Fractions containing decorin were collected.

The core protein is purified from cloned cell lines transfected with the pSV2-decorin/CP vector or the vector containing the alanine-mutated cDNA and amplified as described above. These cells are grown to confluency as described above. At confluency the cell monolayer is washed four times with serum-free medium and incubated in α MEM supplemented with 2 mM glutamine for 2 hours. This spent medium is discarded. Cells are then incubated with α MEM supplemented with 2 mM glutamine for 24 hours and the spent media are collected and immediately made to 0.5 mM phenylmethylsulfonyl fluoride, 1 µg/ml pepstatin, 0.04 mg/ml aprotinin and 5 mM EDTA as serum-free spent media. The spent media are first passed through gelatin-Sepharose and the flow-through fraction is then batch-absorbed to CM-Sepharose Fast Flow (Pharmacia Fine Chemicals, Piscataway, N.J.) preequilibrated in 50 mM Tris/HCl, pH 7.4 containing 0.1M NaCl. After overnight incubation at 4° C., the slurry is poured into a column, washed extensively with the preequilibration buffer and eluted with 0.1M-1M linear gradient of NaCl in 50 mM Tris/HCl, pH 7.4. The fractions containing decorin are pooled, dialyzed against 50 mM $NH_4HCO_3$ and lyophilized. The lyophilized material is dissolved in 50 mM Tris, pH 7.4, containing 8M urea and applied to a Sephacryl S-200 column (1.5×110 cm). Fractions containing decorin core proteins as revealed by SDS-polyacrylamide electrophoresis are collected and represent purified decorin core protein.

EXAMPLE II

BINDING OF TGFβ TO DECORIN

A. Affinity Chromatography of TGFβ on Decorin-Sepharose

Decorin and gelatin were coupled to cyanogen bromide-activated Sepharose (Sigma) by using 1 mg of protein per ml of Sepharose matrix according to the manufacturer's instructions. Commercially obtained TGFβ-1 (Calbiochem, La Jolla, Calif.) was $^{125}$I-labelled by the chloramine T method (Frolik et al., J. Biol. Chem. 259:10995–11000 (1984)) which is incorporated herein by reference and the labeled TGFβ was separated from the unreacted iodine by gel filtration on Sephadex G-25, equilibrated with phosphate buffered saline (PBS) containing 0.1% bovine serum albumin (BSA) (FIG. 2). [$^{125}$I]-TGFβ1 (5×10$^5$ cpm) was incubated in BSA-coated polypropylene tubes with 0.2 ml of packed decorin-Sepharose (○) or gelatin-Sepharose (●) in 2 ml of PBS pH 7.4, containing 1M NaCl and 0.05% Tween 20. After overnight incubation, the affinity matrices were transferred into BSA-coated disposable columns (Bio Rad) and washed with the binding buffer. Elution was effected first with 3M NaCl in the binding buffer and then with 8M urea in the same buffer. Fractions were collected, counted for radioactivity in a gamma counter and analyzed by SDS-PAGE under nonreducing condition using 12% gels.

Figure 2B:
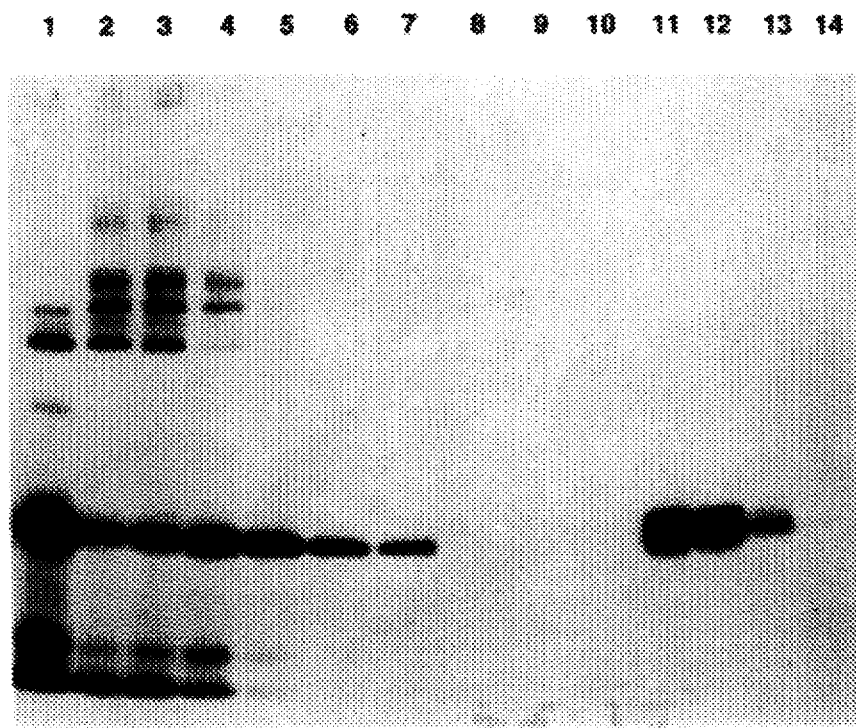
FIGS. 2A and 2B show binding of [$^{125}$I]TGFβ1 to decorin-Sepharose.
Figure 2A:
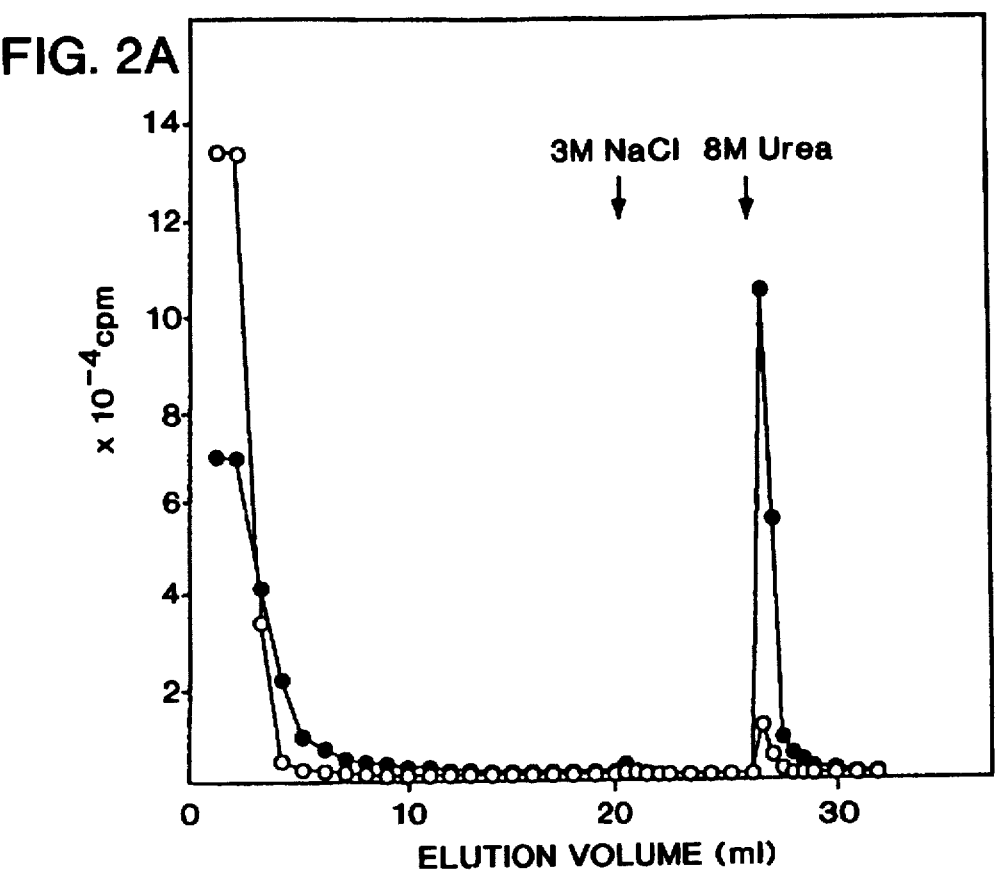

FIG. 2A shows the radioactivity profile from the two columns and the SDS-PAGE analysis of the fractions is shown in FIG. 2B. The TGFβ-1 starting material contains a major band at 25 kd. This band represents the native TGFβ-1 dimer. In addition, there are numerous minor bands in the preparation. About 20–30% of the radioactivity binds to the decorin column and elutes with 8M urea, whereas only about 2% of the radioactivity is present in the urea-eluted fraction in the control fractionation performed on gelatin-Sepharose (FIG. 2A). The decorin-Sepharose nonbound fraction contains all of the minor components and some of the 25 kd TGFβ-1, whereas the bound, urea-eluted fraction contains only TGFβ-1 (FIG. 2B). These results show that TGFβ-1 binds specifically to decorin, since among the various components present in the original TGFβ-1 preparation, only TGFβ-1 bound to the decorin-Sepharose affinity matrix and since there was very little binding to the control gelatin-Sepharose affinity matrix. The TGFβ-1 that did not bind to the decorin-Sepharose column may have been denatured by the iodination. Evidence for this possibility was provided by affinity chromatography of unlabeled TGFβ-1 as described below.

In a second experiment, unlabeled TGFβ-1 180 ng was fractionated on decorin-Sepharose as described above for $^{125}$I-TGFβ.

TGFβ-1 (180 ng) was incubated with decorin-Sepharose or BSA-agarose (0.2 ml packed volume) in PBS (pH 7.4) containing 1% BSA. After overnight incubation at 4° C., the resins were washed with 15 ml of the buffer and eluted first with 5 ml of 3M NaCl in PBS then with 5 ml of PBS containing 8M urea. Aliquots of each pool were dialyzed against culture medium without serum and assayed for the inhibition of [$^3$H]thymidine incorporation in Mv1Lu cells (Example III). The amounts of TGFβ-1 in each pool were calculated from the standard curve of [$^3$H]thymidine incorporation obtained from a parallel experiment with known concentration of TGFβ-1. The results show that the TGFβ-1 bound essentially quantitatively to the decorin column, whereas there was little binding to the control column (Table 1). The partial recovery of the TGFβ-1 activity may be due to loss of TGFβ-1 in the dialyses.

TABLE I

Decorin-Sepharose affinity chromatography of nonlabeled TGFβ-1 monitored by growth inhibition assay in MvlLu cells.

| | TGFβ-1 (ng) | |
|---|---|---|
| Elution | Decorin-Sepharose | BSA-Sepharose |
| Flow through & wash | 2.7 (2.3%) | 82.0 (93.9%) |
| 3 M NaCl | 2.2 (1.8%) | 1.3 (1.5%) |
| 8 M Urea | 116.0 (95.9%) | 4.0 (4.6%) |

B. Binding of TGFβ-1 to Decorin in a Microtiter Assay: Inhibition by Core Protein and Biglycan The binding of TGFβ-1 to decorin was also examined in a microtiter binding assay. To perform the assay, the wells of a 96-well microtiter plate were coated overnight with 2µg/ml of recombinant decorin in 0.1M sodium carbonate buffer, pH 9.5. The wells were washed with PBS containing 0.05% Tween (PBS/Tween) and samples containing 5×10$^4$ cpm of [$^{125}$I]-TGFβ-1 and various concentrations of competitors in PBS/Tween were added to each well. The plates were then incubated at 37° C. for 4 hours (at 4° C. overnight in experiments with chondroitinase ABC-digested proteoglycans), washed with PBS/Tween and the bound radioactivity was solubilized with 1% SDS in 0.2M NaOH. Total binding without competitors was about 4% under the conditions used. Nonspecific binding, determined by adding 100-fold molar excess of unlabeled TGFβ-1 over the labeled TGFβ-1 to the incubation mixture, was about 13% of total binding. This assay was also used to study the ability of other decorin preparations and related proteins to compete with the interaction.

Completion of the decorin binding was examined with the following proteins (FIG. 3A and 3B; symbols are indicated in the section of BRIEF DESCRIPTION OF THE FIGURES):

Decorin isolated from bovine skin and biglycan isolated from bovine articular cartilage (PGI and PGII, obtained from Dr. Lawrence Rosenberg, Montefiore Medical Center, N.Y.; and described in Rosenberg et al., J. Biol. Chem. 250:6304–6313, (1985), incorporated by reference herein), chicken cartilage proteoglycan (provided by Dr. Paul Goetinck, La Jolla Cancer Research Foundation, La Jolla, Calif., and described in Goetinck, P. F., in THE GLYCOCONJUGATES, Vol. III, Horwitz, M. I., Editor, pp. 197–217, Academic Press, NY). For the preparation of core proteins, proteoglycans were digested with chondroitinase ABC (Seikagaku, Tokyo, Japan) by incubating 500 µg of proteoglycan with 0.8 units of chondroitinase ABC in 250 µl of 0.1M Tris/Cl, pH 8.0, 30 mM sodium acetate, 2 mM PMSF, 10 mM N-ethylmalelmide, 10 mM EDTA, and 0.36 mM pepstatin for 1 hour at 37° C. Recombinant decorin and decorin isolated from bovine skin (PGII) inhibited the binding of [$^{125}$I]-TGFβ-1, as expected (FIG. 3A). Biglycan isolated from bovine articular cartilage was as effective an inhibitor as decorin. Since chicken cartilage proteoglycan, which carries many chondroitin sulfate chains, did not show any inhibition, the effect of decorin and biglycan is unlikely to be due to glycosaminoglycans. Bovine serum albumin did not shown any inhibition. This notion was further supported by competition experiments with the mutated decorin core protein (not shown) and chondroitinase ABC-digested decorin and biglycan (FIG. 3B). Each of these proteins was inhibitory, whereas cartilage proteoglycan core protein was not. The decorin and biglycan core proteins were somewhat more active than the intact proteoglycans. Bovine serum albumin treated with chondroitinase ABC did not shown any inhibition. Additional binding experiments showed that [$^{125}$I]-TGFβ-1 bound to microtiter wells coated with biglycan or its chondroitinase-treated core protein. These results show that TGFβ-1 binds to the core protein of decorin and biglycan and implicates the leucine-rich repeats these proteins share as the potential binding sites.

EXAMPLE III

ANALYSIS OF THE EFFECT OF DECORIN ON CELL PROLIFERATION STIMULATED OR INHIBITED BY TGFβ-1

The ability of decorin to modulate the activity of TGFβ-1 was examined in [$^3$H]thymidine incorporation assays. In one assay, an unamplified CHO cell line transfected only with pSV2dhfr (control cell line A in reference 1, called CHO cells here) was used. The cells were maintained in nucleoside-free alpha-modified minimal essential medium (e-MEM, GIBCO, Long Island, N.Y.) supplemented with 9% dialyzed fetal calf serum (dFCS) and [$^3$H]thymidine incorporation was assayed as described (Cheifetz et al., Cell 48:409–415 (1987)). TGFβ-1 was added to the CHO cell cultures at 5 ng/ml. At this concentration, it induced a 50% increase of [$^3$H]thymidine incorporation in these cells. Decorin or BSA was added to the medium at different concentrations. The results are shown in FIG. 4A. The data represent percent neutralization of the TGFβ-1-induced growth stimulation, i.e., [$^3$H]thymidine incorporation, in the absence of either TGFβ-1 or decorin=0%, incorporation in the presence of TGFβ-1 but not decorin=100%. Each point shows the mean ± standard deviation of triplicate samples. Decorin (●) BSA (○).

Decorin neutralized the growth stimulatory activity of TGFβ-1 with a half maximal activity at about 5 µg/ml. Moreover, additional decorin suppressed the [$^3$H]-thymidine incorporation below the level observed without any added TGFβ-1, demonstrating that decorin also inhibited TGFβ made by the CHO cells themselves. Both the decorin-expressor and control CHO cells produced an apparently active TGFβ concentration of about 0.25 ng/ml concentration into their conditioned media as determined by the inhibition of growth of the mink lung epithelial cells. (The assay could be performed without interference from the decorin in the culture media because, as shown below, the effect of TGFβ on the mink cells was not substantially inhibited at the decorin concentrations present in the decorin-producer media.)

Experiments in MvLu mink lung epithelial cells (American Type Culture Collection CCL64) also revealed an effect by decorin on the activity of TGFβ-1. FIG. 4B shows that in these cells, the growth of which is measured by thymidine incorporation, had been suppressed by TGFβ-1. Assay was performed as in FIG. 4A, except that TGFβ-1 was added at 0.5 ng/ml. This concentration of TGFβ induces 50% reduction of [$^3$H]-thymidine incorporation in the MvlLu cells. The data represent neutralization of TGFβ-induced growth inhibition; i.e., [$^3$H]-thymidine incorporation in the presence of neither TGFβ or decorin=100%; incorporation in the presence of TGFβ but not decorin=0%.

EXAMPLE IV

NEW DECORIN-BINDING FACTOR THAT CONTROLS CELL SPREADING AND SATURATION DENSITY

Figure 5B:
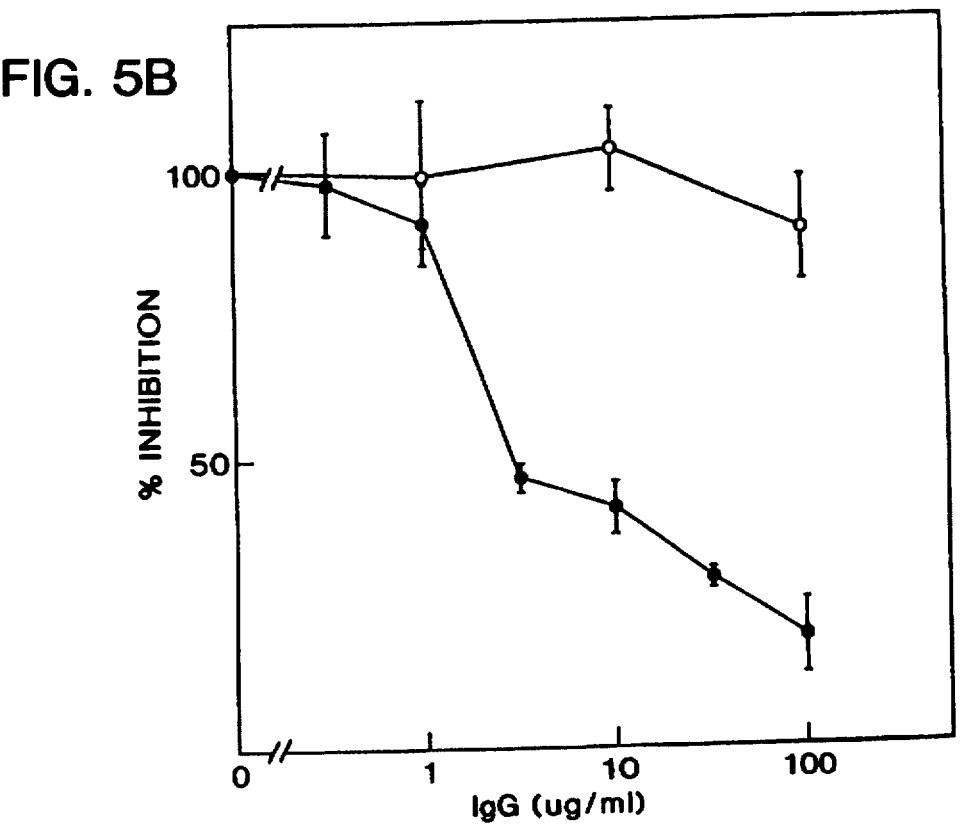
FIG. 5B shows identification of the growth stimulatory material from gel filtration as TGFβ1. The growth stimulatory activity from the late fractions from Sepharose 6B (bar in panel A) was identified by inhibiting the activity with protein A-purified IgG from an anti-TGFβ antiserum. Data represent percent inhibition of growth stimulatory activity in a [$^3$H]thymidine incorporation assay. Each point shows the mean ±standard deviation of triplicate determinations. Anti-TGFβ1 (○), normal rabbit IgG (●).
Figure 5A:
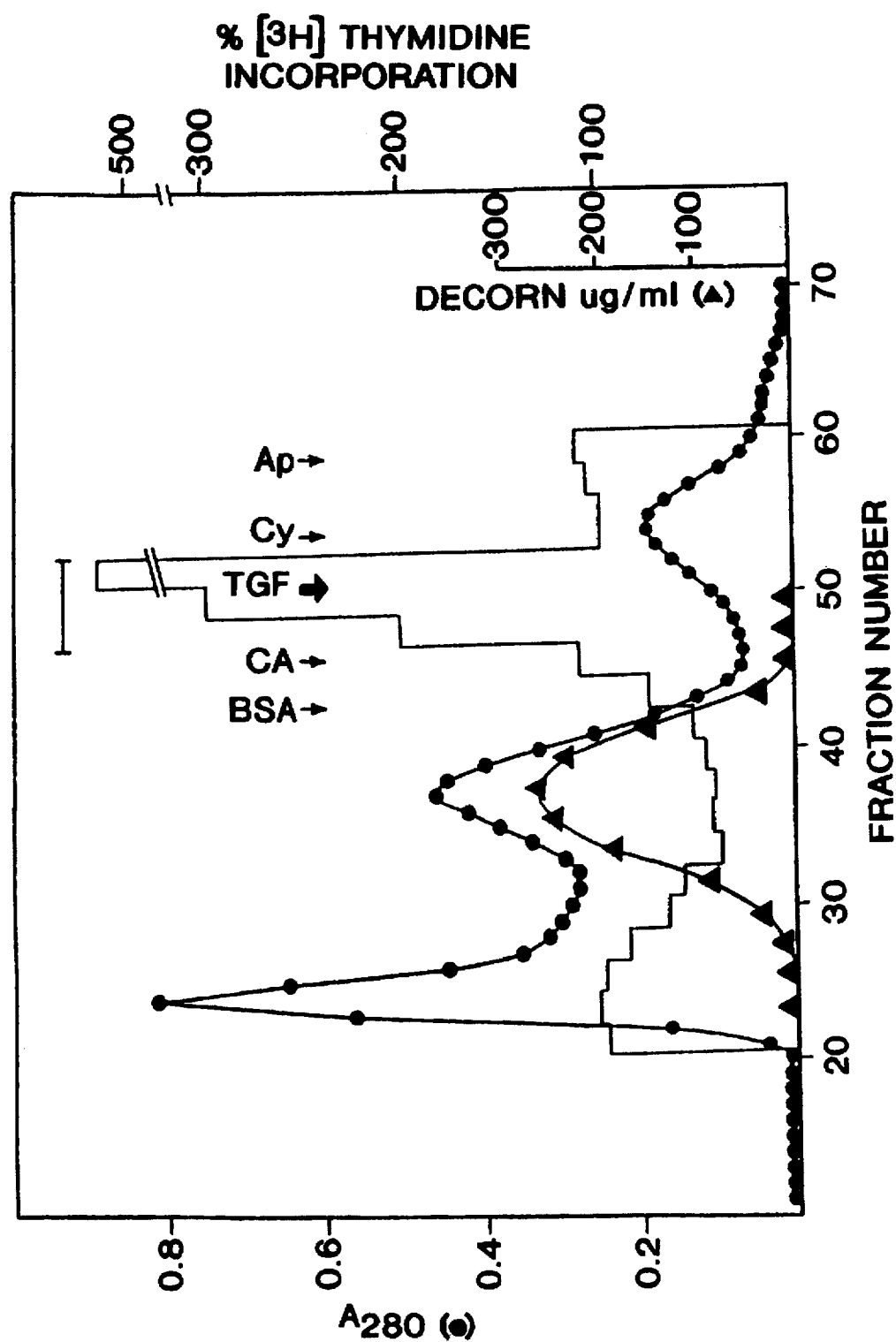
FIG. 5A shows separation of growth inhibitory activity from decorin-expressing CHO cells by gel filtration. Serum-free conditioned medium of decorin overexpressor cells was fractionated by DEAE-Sepharose chromatography in a neutral Tris-HCl buffer and fractions containing growth inhibitory activity were pooled, made 4M with guanidine-HCl and fractionated on a Sepharose CL-6B column equilibrated with the same guanidine-HCl solution. The fractions were analyzed for protein content, decorin content, and growth regulatory activities. Elution positions of marker proteins are indicated by arrows. BSA: bovine serum albumin (Mr=66,000); CA: carbonic anhydrase (Mr=29,000); Cy:cytochrome c (Mr=12,400); Ap:aprotinin (Mr=6,500); TGF: [$^{125}$I]TGFβ1(Mr=25,000).

Analysis of the decorin contained in the overexpressor culture media not only uncovered the activities of decorin described above, but also revealed the presence of other decorin-associated growth regulatory activities. The overexpressor media were found to contain a TGFβ-like growth inhibitory activity. This was shown by gel filtration of the DEAE-isolated decorin under dissociating conditions. Serum-free conditioned medium of decorin overexpressor CHO-DG44 cells transfected with decorin cDNA was fractionated by DEAE-Sepharose chromatography in a neutral Tris-HCl buffer and fractions containing growth inhibitory activity dialyzed against 50 mM $NH_4HCO_3$, lyophilized and dissolved in 4M with guanidine- HCl in a sodium acetate buffer, pH 5.9. The dissolved material was fractionated on a 1.5×70 cm Sepharose CL-6B column equilibrated with the same guanidine-HCl solution. The fractions were analyzed by SDS-PAGE, decorin ELISA and cell growth assays, all described above. Three protein peaks were obtained. One contained high molecular weight proteins such as fibronectin (m.w. 500,000) and no detectable growth regulatory activities, the second was decorin with the activities described under Example III and the third was a low molecular weight (10,000–30,000–dalton) fraction that had a growth inhibitory activity in the mink cell assay and stimulated the growth of the CHO cells. FIG. 5A summarizes these results. Shown are the ability of the gel filtration fractions to affect [$^3$H]-thymidine incorporation by the CHO cells and the concentration of decorin as determined by enzyme immunoassay. Shown also (arrows) are the elution positions of molecular size markers: BSA, bovine serum albumin (Mr=66,000); CA, carbonic anhydrase (Mr=29,000); Cy, cytochrome c (Mr=12,400); AP, aprotinin (Mr=6,500); TGF, [$^{125}$I]TGFβ-1 (Mr=25,000).

The nature of the growth regulatory activity detected in the low molecular weight fraction was examined with an anti-TGFβ-1 antiserum. The antiserum was prepared against a synthetic peptide from residues 78–109 of the human mature TGFβ-1. Antisera raised by others against a cyclic form of the same peptide, the terminal cysteine residues of which were disulfide-linked, have previously been shown to inhibit the binding of TGFβ-1 to its receptors (Flanders et al., Biochemistry 27:739–746 (1988), incorporated by reference herein). The peptide was synthesized in an Applied Biosystems solid phase peptide synthesizer and purified by HPLC. A rabbit was immunized subcutaneously with 2 mg per injection of the peptide which was mixed with 0.5 mg of methylated BSA (Sigma, St. Louis, Mo.) and emulsified in Freund's complete adjuvant. The injections were generally given four weeks apart and the rabbit was bled approximately one week after the second and every successive injection. The antisera used in this work has a titer (50% binding) of 1:6,000 in radioimmunoassay, bound to TGFβ-1 in immunoblots.

This antiserum was capable of inhibiting the activity of purified TGFβ-1 on the CHO cells. Moreover, as shown in FIG. 5B, the antiserum also inhibited the growth stimulatory activity of the low molecular weight fraction as determined by the [$^3$H]-thymidine incorporation assay on the CHO cells. Increasing concentrations of an IgG fraction prepared from the anti-TGFβ-1 antiserum suppressed the stimulatory effect of the low molecular weight fraction in a concentration-dependent manner (●). IgG from a normal rabbit serum had no effect in the assay (○).

The above result identified the stimulatory factor in the low molecular weight fraction as TGFβ-1. However, TGFβ-1 is not the only active compound in that fraction. Despite the restoration of thymidine incorporation by the anti-TGFβ-1 antibody shown in FIG. 5B, the cells treated with the low molecular weight fraction were morphologically different from the cells treated with the control IgG or cells treated with antibody alone. This effect was particularly clear when the antibody-treated, low molecular weight fraction was added to cultures of H-ras transformed NIH 3T3 cells (Der et al., Proc. Natl. Acad. Sci. USA 79:3637–3640 (1982)). Cells treated with the low molecular weight fraction and antibody appeared more spread and contact inhibited than the control cells. This result shows that the CHO cell-derived recombinant decorin is associated with a cell regulatory factor, MRF, distinct from the well characterized TGFβ's.

Additional evidence that the new factor is distinct from TGFβ-1 came from HPLC experiments. Further separations of the low molecular weight from the Sepharose CL-6B column was done on a Vydac C4 reverse phase column (1 ×25 cm, 5 μm particle size, the Separations Group, Hesperia, Calif.) in 0.1% trifluoroacetic acid. Bound proteins were eluted with a gradient of acetonitrite (22–40%) and the factions were assayed for growth-inhibitory activity in the mink lung epithelial cells and MRF activity in H-ras 3T3 cells. The result showed that the TGFβ-1 activity eluted at the beginning of the gradient, whereas the MRF activity eluted toward the end of the gradient.

EXAMPLE V

CONSTRUCTION AND EXPRESSION OF MBP-DECORIN FRAGMENT FUSION PROTEINS

Figure 6:
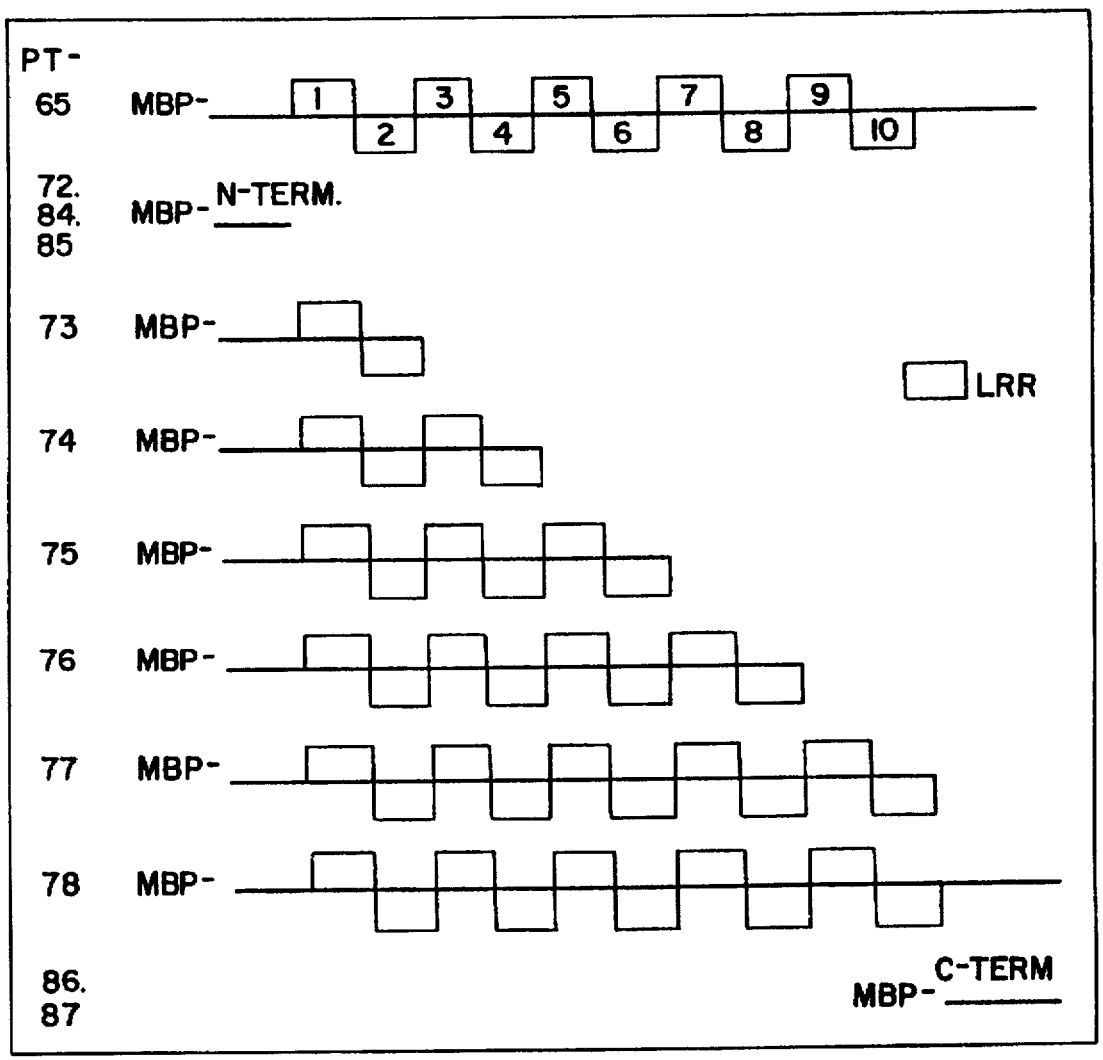
FIG. 6 is a schematic diagram of MBP-decorin fragment fusion proteins. LRR is a leucine rich repeat. MBP is maltose binding protein.

MBP-Decorin fragment fusion proteins of varying lengths were engineered such that the Maltose Binding Protein (MBP) was attached to the amino terminus of the gene encoding mature decorin as shown in FIG. 6. The techniques incorporated for such construction are described in F. M. Ausubel et al., *Current Protocols in Molecular Biology*, John Wiley and Sons (1987) and Maniatis et al., *Molecular Cloning: A Laboratory Manual*, Cold Spring Harbor Laboratory (1982), which are incorporated herein by reference.

The decorin-encoding DNA fragments were generated by polymerase chain reaction (PCR), Scharf et al., Science 233:1076–1078 (1986), which is incorporated herein by reference. The primers, synthetic oligonucleotides obtained from Genosys (Houston, Tex.), incorporate an Eco RI restriction site at the 5' end and an Xba I restriction site at the 3' end of the PCR product. In some instances, the primers also included a base change to code for a different amino acid. The primers used to generate specific inserts are identified in Table 2, while the primer sequences are identified in Table 3(SEQ ID Nos. 2 through 16). The template DNA was a large scale CsCl prep of pPG-40 described in Krusius and Ruoslahti, Proc. Natl. Acad. Sci. USA 83:7683–7687 (1986), incorporated herein by reference. The DNA amplification reaction was done in a thermal cycler according to manufacturer's recommendations (Perkin-Elmer Cetus; Norwalk, Conn.) using the Vent™ DNA Polymerase (New England Biolabs; Beverly, Mass.). The decorin-encoding DNA fragments cycled 35–40 times at 94°, 40°, and 72° C.

The PCR products were analyzed by agarose gel electrophoresis, Ausubel et al., supra, and Maniatis et al., supra, to identify and determine the decorin-encoding DNA fragments (see Table 2 under "Insert Size"). The PCR products less than 200 base pairs (bp) in size were purified by electrophoresis onto DEAE-cellulose paper, Ausubel et al., supra.; the PCR products greater than 200 bp were purified by using Prep-A-Gene™ DNA Purification Kit (Bio-Rad; Richmond, Calif.) according to manufacturer's instructions.

The decorin-encoding DNA fragments (insert) were ligated between the Eco RI and Xba I restriction sites of the polylinker in the vector pMAL-p (Protein Fusion and Purification Sytem; New England Biolabs). The ligation had a total of 500 ng of DNA and the molar ratio of insert:vector was 3:1. The ligations were then transformed into *Escherichia coli* (*E. coli*) DH5α cells (Gibco BRL; Gaithersburg, Md.), genotype: F⁻φ80dlacZΔM15, Δ(lacZYA-argF)U169, deoR, recA1, endA1, hsdR17(r$_k$⁻, m$_k$⁺), supE44 λ⁻¹ thi-1, gyrA96, relA1, or *E. coli* Sure™ cells (Stratagene, La Jolla, Calif.), genotype: e14-(mcrA), Δ(mcrCB-hsdSMR-mrr)171, sbcC, recB, recJ, umuC::Tn5 (kan'), uvrC, supE44, lac, gyrA96, relA1, thi-1, endA1 [F'proAB, lacI$^q$ZΔM15, Tn10, (tet')]. The φ80dlacZΔM15 marker of the *E. coli* DH5α strain provides α-complementation of the β-galactosidase gene from pMAL-p. Colonies containing pMAL-p with the decorin-encoding DNA fragments were colorless on plates containing 5-Bromo-4-chloro-3-indolyl-β-D-galactoside (X-gal) due to the interruption of the β-galatosidase gene. Host cells containing pMAL-p only produces blue colonies.

Minipreps of colorless colonies were then made as described in Ausubel et al., supra, and Maniatis et al., supra. Plasmids encoding MBP-decorin fragment fusion proteins PT-73, -74, -75, -77, and -78, were then digested with restriction endonucleases Eco RI and Xba I (both from Promega; Madison, Wis.) and the presence of specific inserts confirmed by agarose gel electrophoresis. The other plasmids encoding fusion proteins, PT-72, -76, -84, -85, -86, and -87, had inserts confirmed by sequencing using Sequenase® Version 2.0 DNA Sequencing Kit (U. S. Biochemical; Cleveland, Ohio) according to manufacturer's instructions.

Test expression of MBP-Decorin fragment fusion proteins were performed in the host bacterial strain (see Table 2). An overnight culture of *E. coli* DH5β or *E. coli* Sure™ cells containing the MBP-decorin fragment fusion protein plasmids were made by taking a stab of a frozen stock and inoculating L-Broth, Ausubel et al., supra, containing 100 µg/ml ampicillin at 37° C. with rapid shaking. The following morning, 1 ml was used to inoculate 10 ml of prewarmed medium (L-Broth containing ampicillin). After 1 hour at 37° C., 100 µl of 0.1M IPTG were added per culture and the induced cultures were allowed to incubate for an additional 2–3 hours. The cells were lysed by resuspending in PAGE Sample Buffer (Novex Experimental Technology; Encinitas, Calif.) with 0.8% β-mercaptoethanol and shearing 10 times with a 1 cc tuberculin syringe. The sample was run on an 8–16% gradient SDS-PAGE gel (Novex Experimental Technology) and a Western Blot (Novex Experimental Technology) was performed according to manufacturer's recommendations. The blot was developed, Ausubel et al., supra, with Rabbit anti-PG40 serum (Telios Pharmaceuticals, Inc.; La Jolla, Calif.) to test for PT-65, -73, -74, -75, -76, -77, and -78, and Rabbit anti-MBP serum (made in-house) to test for PT-72, -84, -85, -86, and -87. The results are indicated in Table 2 under "MW."

Large scale CsCl preps, Ausubel, et al., supra, and Maniatis, et al, supra, of the plasmids encoding MBP-Decorin fragment fusion proteins PT-84, -85, -86, and -87 were made and used to transform *E. coli* DH5β. Expression of the fusion proteins was confirmed by doing a test expression as described above.

Production batches of the fusion proteins were prepared as follows. An overnight culture of *E. coli* DH5β cells containing the MBP-Decorin fragment fusion protein plasmids was made by taking a stab of the frozen stock and inoculating L-Broth containing 100 µg/ml ampicillin at 37° C. with rapid shaking. From this culture, 5 ml were used to inoculate a larger 50 ml overnight culture. The following morning, 50 ml of the larger culture were added to 500 ml of pre-warmed media. Typically 1–4 liters were prepared for each batch. After 1 hour at 37° C., 5 ml of 0.1M IPTG were added per flask and the induced cultures were allowed to incubate for an additional 2–3 hours. The cells were harvested by centrifugation at 5,000 rpm for 10 minutes at 10° C. using either a GSA or GS-3 rotor in an RC5B centrifuge (DuPont Instruments; Wilmington, Del.). The pellets were resuspended in 0.1 volume of lysis buffer (50mM Tris-HCl, pH 7.4, 150 mM NaCl, 0.1M PMSF, and 0.25 mg/ml lysozyme) and incubated for 10–15 minutes on ice. The suspension was freeze/thawed three times by repeated cycling through a dry ice/ethanol bath and a room temperature shaking water bath. The suspension was sheared by homogenization using a dounce homogenizer. The lysate was pre-cleared by centrifugation at 12,000 rpm for 30 minutes in a SA-600 rotor (DuPont). The cleared supernatant was decanted and saved. A final clarification step was done by centrifuging for 30 minutes at 4° C. in an RC-80 ultracentrifuge using an AH-629 rotor (DuPont). The final cleared lysates were stored either at 4° C. or -20° C. until ready to be purified.

Affinity purifications of the MBP-Decorin fusion proteins were done using an amylose resin (New England Biolabs). Briefly, six to seven ml of resin were packed into a 2.5×10 cm glass column in MBP column buffer (10mM Tris-HCl, pH 8.4, 1 mM EDTA, 0.5M NaCl). The resin was pre-equilibrated with at least 3 column volumes of MBP column buffer containing 0.25% Tween 20. Cleared lysate as prepared above was diluted 1 part lysate to 1 part 2×MBP column buffer containing 0.5% Tween 20 and added to the column at a flow rate of 50–100 ml/hr. Typically, 100–150 ml of diluted lysate were passed over each column. Non-specific material was removed by washing with at least 3 column volumes each of MBP column buffer containing 0.25% Tween 20 and MBP column buffer. The purified MBP-Decorin fragment fusion protein was eluted with 5×4 ml aliquots of MBP column buffer containing 10 mM maltose. Peak fractions containing the fusion protein were pooled, assayed to determine protein quantity (Bio-Rad Protein Kit; Richmond, Calif. or Pierce BCA Protein Kit; Rockford, Ill.), run on an 8–16% SDS-PAGE gel (Novex Experimental Technology), and stained with Coomasie Blue (Novex Experimental Technology) to check for purity. The results of the fusion protein are in Table I under "MW". The purified fusion protein was stored at 4° C. or -20° C. in aliquots until ready to be tested for activity.

The pMAL-p vector also was engineered such that a termination codon was incorporated between the Eco RI and Xba I sites. During this process, the original Eco RI site in the vector was destroyed and replaced at a position downstream from a second Factor Xa cleavage site. The second Factor Xa site was incorporated to facilitate subsequent cleavage of the decorin fusion protein from the MBP carrier. The construction involved annealing complimentary oligos (OT-98 and OT-99; sequences in Table 3) and ligating into pMAL-p at the Eco RI and Xba I sites. Ausubel, et al., supra, and Maniatis, et al., supra. The ligation (PT-71) was transformed into *E. coli* DH5α cells, mini-preps were made from colorless colonies and the clones were sequenced for insert.

Expression of the protein followed the same procedure as the MBP-Decorin fragment fusion proteins above. The results are indicated in Table 2 under "MW."

TABLE 2

| CLONE | 5' PRIMER | 3' PRIMER | INSERT SIZE (bp) | HOST BACTERIAL STRAIN | # AA OF INSERT | MW (Kd) |
|---|---|---|---|---|---|---|
| PT-65 | OT-83 | OT-85 | 990 | DH5α | 330 | 76 |
| Mature Whole Decorin | (29mer) | (38mer) | | | | |
| PT-72 | OT-83 | OT-102 | 137 | DH5α | 46 | 45 |
| N-Terminal: | (29mer) | (31mer) | | | | |
| $C_1$ mutated to Y | | | | | | |
| PT-73 | OT-83 | OT-103 | 285 | DH5α | 95 | 50 |
| N-Term. to LRR 2 | (29mer) | (36mer) | | | | |
| PT-74 | OT-83 | OT-104 | 420 | DH5α | 140 | 55 |
| N-Term. to LRR 4 | (29mer) | (32mer) | | | | |
| PT-75 | OT-83 | OT-105 | 561 | DH5α | 187 | 60 |
| N-Term. to LRR 6 | (29mer) | (32mer) | | | | |
| PT-76 | OT-83 | OT-106 | 705 | DH5α | 235 | 65 |
| N-Term. to LRR 8 | (29mer) | (32mer) | | | | |
| PT-77 | OT-83 | OT-107 | 843 | DH5α | 281 | 70 |
| N-Term. to LRR 10 | (29mer) | (33mer) | | | | |
| PT-78 | OT-83 | OT-108 | 918 | DH5α | 306 | 73 |
| N-Term. to ½ C-Term. | (29mer) | (32mer) | | | | |
| PT-84 | OT-83 | OT-118 | 137 | Sure ™ | 46 | 45 |
| N-Term: | (29mer) | (77mer) | | | | |
| $C_{1-4}$ mutated to S | | | | | | |
| PT-85 | OT-83 | OT-119 | 137 | Sure ™ | 46 | 45 |
| N-Term: | (29mer) | (65mer) | | | | |
| $C_{2-3}$ mutated to S | | | | | | |
| PT-86 | OT-120 | OT-85 | 165 | Sure ™ | 54 | 46 |
| C-Terminal | (29mer) | (38mer) | | | | |
| PT-87 | OT-121 | OT-85 | 165 | Sure ™ | 54 | 46 |
| C-Term: | (29mer) | (38mer) | | | | |
| $C_1$ mutated to S | | | | | | |
| PT-71 | — | — | — | DH5α | — | 40 |
| MBP | | | | | | |

$C_1$ = the first cysteine
$C_{1-4}$ = the first through the fourth cysteine
$C_{2-3}$ = the second and third cysteine

TABLE 3

| | |
|---|---|
| OT-83 | 5'...GG.GAA.TTC.GAT.GAG.GCT.TCT.GGG.ATA.GGC...3' (SEQ ID NO. 2) |
| OT-85 | 5'...GG.TCT.AGA.CTA.CTT.ACT.TAT.AGT.TTC.CGA.GTT.GAA.TGG...3' (SEQ ID NO. 3) |
| OT-102 | 5'...GG.TCT.AGA.TTA.GTC.CAG.ACC.CAA.ATC.AGA.AC...3' (SEQ ID NO. 4) |
| OT-103 | 5'...GG.TCT.AGA.TTA.AGG.ACT.AAC.TTT.GCT.AAT.TTT.ATT.G...3' (SEQ ID NO. 5) |
| OT-104 | 5'...GG.TCT.AGA.TTA.TTT.TCG.CAC.TTT.GGT.GAT.CTC...3' (SEQ ID NO. 6) |
| OT-105 | 5'...GG.TCT.AGA.TTA.GCT.GGT.GAT.ATT.GGT.ATC.AGC...3' (SEQ ID NO. 7) |
| OT-106 | 5'...GG.TCT.AGA.TTA.ATT.GTC.AAC.AGC.AGA.GAT.GCT...3' (SEQ ID NO. 8) |
| OT-107 | 5'...GG.TCT.AGA.TTA.TCC.AAC.TAC.AGA.GAT.ATT.GTT.G...3' (SEQ ID NO. 9) |
| OT-108 | 5'...GG.TCT.AGA.TTA.CGG.GTT.GCT.GAA.AAG.ACT.CAC...3' (SEQ ID NO. 10) |
| OT-118 | 5'...GG.TCT.AGA.TTA.GTC.CAG.ACC.CAA.ATC.AGA.ACA.CTG.GAC.CAC.TCG.AAG.ATG.GGA.TTG.AGA.GCG.GAA.GGG.GGA.CAC.TGG...3' (SEQ ID NO. 11) |
| OT-119 | 5'...GG.TCT..AGA.TTA.GTC.CAG.ACC.CAA.ATC.AGA.ACA.CTG.GAC.CAC.TCG.AAG.ATG.GGA.TTG.AGA.GCG.GAA...3' (SEQ ID NO. 12) |
| OT-120 | 5'...GG.GAA.TTC.TCA.AGT.GAC.TTC.TGC.CCA.CCT...3' (SEQ ID NO. 13) |
| OT-121 | 5'...GG.GAA.TTC.TCA.AGT.GAC.TT.TCC.CCA.CCT...3' (SEQ ID NO. 14) |
| OT-98 | 5'...AA.TTT.ATC.GAG.GGT.AGG.GGT.GAA.TTC.TAA.T...3' (SEQ ID NO. 15) |
| OT-99 | 5'...CT.AGA.TTA.GAA.TTC.ACC.CCT.ACC.CTC.GAT.A...3' (SEQ ID NO. 16) |

Tables 4–15 below provide the nucleotide and corresponding amino acid sequences of the decorin fragment fusion proteins prepared as described above. Each table also identifies the Eco RI and Xba I ligation sites.

TABLE 4

(SEQ ID NOS. 26 through 28) PT-65 Sequence

```
                                                                                          100
5'...  GAATTCGATGAGGCTTCTGGGATAGGCCCAGAAGTTCCTGATGACCGCGACTTCGAGCCCTCCCTAGCCCCAGTGTGCCCCTTCCGCTGTCAATGCCATC
       ----+----|----+----|----+----|----+----|----+----|----+----|----+----|----+----|----+----|----+----|
       CTTAAGCTACTCCGAAGACCCTATCCGGGTCTTCAAGGACTACTGGCGCTGAAGCTCGGGAGGGATCCGGGGTCACACGGGAAGGCGACAGTTACGGTAG
        e  f  d  e  a  s  g  i  g  p  e  v  p  d  d  r  d  f  e  p  s  l  g  p  v  c  p  f  r  c  q  c  h  l
                                                                                          200
       TTCGAGTGGTCCAGTGTTCTGATTTGGGTCTGGACAAAGTGCCAAAGTGTCGACACAACTGTCTAGACCTGCAAACTGCAAAACAACAAATAACCGA
       ----+----|----+----|----+----|----+----|----+----|----+----|----+----|----+----|----+----|----+----|
       AAGCTCACCAGGTCACAAGACTAAACCCAGACTGTTTCACGGTTTCACAGCTGTGTTGACAGATCTGGACGTTTGACGTTTTGTGTTTATTGGCT
        r  v  v  q  c  s  d  l  g  l  d  k  v  p  k  d  l  p  p  d  t  t  l  d  q  n  n  k  i  t  e
                                                                                          300
       AATCAAAGATGGAGAGACTTTAAGAACCTGAAGAACCTTCACGCATTGATTCTTGTCAACAATAAAATTAGCAAAGTTAGTCCTGGAGCATTTACACCTTTG
       ----+----|----+----|----+----|----+----|----+----|----+----|----+----|----+----|----+----|----+----|
       TTAGTTTCTACCTCTGAAATTCTTGGACTTCTTGGAAGTGCGTAACTAAGAACAGTTGTTATTTTAATCGTTTCAATCAGGACCTCGTAAATGTGAAAC
        i  k  d  g  d  f  k  n  l  k  n  l  h  a  l  i  v  n  n  k  i  s  k  v  s  p  g  a  f  t  p  l
                                                                                          400
       GTGAAGTTGGAACGACTTTATCTGTCCAAGAATCAGCTGAACCAGATGATTGTCATAGAACCTGGGCACCAATCCGCTGAAGAGCTCAGGAATTGAAAATGGGGC
       ----+----|----+----|----+----|----+----|----+----|----+----|----+----|----+----|----+----|----+----|
       CACTTCAACCTTGCTGAAATGACAGGTTCTTAGTCGACTTGGTCTACTAACAGTATCTTGGACCCGTGTTAGGCGACTTCTCGAGTCTTAACTTTTACCCCG
        v  k  l  e  r  l  y  l  s  k  n  q  l  k  e  l  p  e  k  m  p  k  t  l  q  e  l  r  a  h  e  n  e  i
                                                                                          500
       TCACCAAAGTGCGAAAAGTACTTTCAATGGACTGAACCAGATTGCTGATACCAATATCACCAGCATTCCTCAAGGTCTTCCTCCTTCCCTTACGGAATTACATCTT
       ----+----|----+----|----+----|----+----|----+----|----+----|----+----|----+----|----+----|----+----|
       AGTGGTTTCACGCTTTCATGAAAGTTACCTGACTTGGTCTAACGACTATGGTTATAGTGGTCGTAAGGAGTTCCAGAAGGAGGAATGCCTTAATGTAGAA
        t  k  v  r  k  v  t  f  n  g  l  n  q  m  i  v  i  e  l  g  t  n  p  l  k  s  s  g  i  e  n  g  a
                                                                                          600
       TTTCCAGGGAATGAAGAAGCTCTCCTACATCCGATGCTGATGAAAGGACTGAAATAATTTGGCTAAGTTGGGATTGAGTTTCAACAGCATCTCTGCTGTTGACA
       ----+----|----+----|----+----|----+----|----+----|----+----|----+----|----+----|----+----|----+----|
       AAAGGTCCCTTACTTCTTCGAGAGGATAGTAGGCGTAACGACTATGGTGGTCGTAAGGAGTTCGTAAGGAGTTGTCGTAGAGACGACAACTGT
        f  q  g  m  k  k  l  s  y  i  r  i  a  d  t  n  i  t  s  i  p  q  g  l  p  p  s  l  t  e  l  h  l
                                                                                          700
       GATGGCAACAAAATCAGCAGAGTTGATGCAGCTTCAAAGCTAGCAGCTGAAAGGACTGAATAATTTGGCTAAGTTGGGATTGAGTTCAACAGCATCTCTGCTGTTGACA
       ----+----|----+----|----+----|----+----|----+----|----+----|----+----|----+----|----+----|----+----|
       CTACCGTTGTTTTAGTCGTCTCAACTACGACTCGATCGGACTTTCCTGACTTATTAAACCGATTCAACCTAACTGTCTGGCTTCTAGAGACGACAACTGT
        d  g  n  k  i  s  r  v  d  a  a  s  l  k  g  l  n  n  l  a  k  l  g  l  s  f  n  s  i  s  a  v  d  n
```

TABLE 4-continued (SEQ ID NOS. 26 through 28) PT-65 Sequence

```
ATGGCTCTCTGGCCAACACGCCTCATCTGAGGAGCTTCACTTGGACAACAACAAGCTTACCAGAGTACCTGGTGGGCTGGCAGAGCATAAGTACATCCA
-----+---------+---------+---------+---------+---------+---------+---------+---------+---------+  800
TACCGAGAGACCGGTTGTGCGGAGTAGACTCCCTCGAAGTGAACCTGTTGTTGTTCGAATGGTCTCATGGACCACCCGACCGTCTCGTATTCATGTAGGT
 g  s  l  a  n  t  p  h  r  e  l  h  l  d  n  k  l  t  r  v  p  g  g  l  a  e  h  k  y  i  q

GGTGTCTACCTTCATAACAACAATATCTCTGTAGTTGGATCAAGTAGTCAAGGCTTCTTATTCGGGTGTGAGT
-----+---------+---------+---------+---------+---------+---------+---------+---------+---------+  900
CCAACAGATGGAAGTATTGTTGTTATAGAGACATCAACCTAGTTCACTGAAGACGGGTGGACCTGTGTTGTTGGTTTTTCCGAAGAATAAGCCACACTCA
 v  v  y  l  h  n  n  n  i  s  v  v  g  s  s  d  f  c  p  p  g  h  n  t  k  k  a  s  y  s  g  v  s
                                                                                                    X
                                                                                                    B
                                                                                                    A
                                                                                                    1

CTTTTCAGCAACCCGGTTCCAGTACTGGGAGATACAGCCATCCACCTTCAGATGTGTCTACGTGCGCTCTGCCATTCAACTCGGAAACTATAAGTAATCTA
-----+---------+---------+---------+---------+---------+---------+---------+---------+---------+  1000
GAAAAGTCGTTGGGCCAGGTCATGACCCTCTATGTCGGTAGGTGGAAGTCTACACAGATGCACGCGAGACGGTAAGTTGAGCCTTTGATATTCATTAGAT
 l  f  s  n  p  v  q  y  w  e  i  q  p  s  t  f  r  c  v  y  v  r  s  a  i  q  l  g  n  y  k  .  s  r

GA
-----3' 1002
CT
```

TABLE 5

PT-72 Sequence (SEQ ID NOS. 29 through 31)

```
        E
        C
        R
        R
        1
        GAATTCGATGAGGCTTCTGGGATAGGCCCAGAAGTTCCTGATGACCGCG
5'...----.----+----.----+----.----+----.----+----.----
        CTTAAGCTACTCCGAAGACCCTATCCGGGTCTTCAAGGACTACTGGCGC
          e  f  d  e  a  s  g  i  g  p  e  v  p  d  d  r  d

ACTTCGAGCCCTCCCTAGGCCCAGTGTACCCCTTCCGCTGTCAATGCCATG
+----.----+----.----+----.----+----.----+----.----+ 100
TGAAGCTCGGGAGGGATCCGGGTCACATGGGGAAGGCGACAGTTACGGTAG
   f  e  p  s  l  g  p  v  y  p  f  r  c  q  c  h  l

X
                                              B
                                              A
                                              1
TTCGAGTGGTCCAGTGTTCTGATTTGGGTCTGGACTAATCTAGA
----.----+----.----+----.----+----+----...3' 144
AAGCTCACCAGGTCACAAGACTAAACCCAGACCRGATTAGATCT
   r  v  v  q  c  s  d  l  g  l  d  .  s  r
```

TABLE 6

(SEQ ID NOS. 32 through 34) PT-73 Sequence

```
        E
        C
        R
        1
        GAATTCGATGAGGCTTCTGGGATAGGCCCAGAAGTTCCTGATGACCGCGA
5'.....----.----+----.----+----.----+----.----+----.----+
        CTTAAGCTACTCCGAAGACCCTTTCCGGGTCTTCAAGGACTACTGGCGCT e  f  d  e  a  s  g  i  g  p  e  v  p  d  d  r  d

CTTCGAGCCCTCCCTAGGCCCAGTGTGCCCCTTCCGCTGTCAATGCCATC
        ----.----+----.----+----.----+----.----+----.----+ 100
        GAAGCTCGGGAGGGATCCGGGTCACACGGGGAAGGCGACAGTTACGGTAG f  e  p  s  l  g  p  v  c  p  f  r  c  q  c  h  l

TTCGAGTGGTCCAGTGTTCTGATTTGGGTCTGGACAAAGTGCCAAAGGAT
        ----.----+----.----+----.----+----.----+----.----+
        AAGCTCACCAGGTCACAAGACTAAACCCAGACCTGTTTCACGGTTTCCTA r  v  v  q  c  s  d  l  g  l  d  k  v  p  k  d

CTTCCCCCTGACACAACTCTGCTAGACCTGCAAAACAACAAAATAACCGA
        ----.----+----.----+----.----+----.----+----.----+ 200
        GAAGGGGGACTGTGTTGAGACGATCTGGACGTTTTGTTGTTTTATTGGCT l  p  p  d  t  t  l  l  d  l  q  n  n  k  i  t  e

AATCAAAGATGGAGACTTTAAGAACCTGAAGAACCTTCACGCATTGATTC
        ----.----+----.----+----.----+----.----+----.----+
        TTAGTTTCTACCTCTGAAATTCTTGGACTTCTTGGAAGTGCGTAACTAAG i  k  d  g  d  f  k  n  l  k  n  l  h  a  l  i  l
```

TABLE 6-continued (SEQ ID NOS. 32 through 34) PT-73 Sequence

```
                                            X
                                            B
                                            A
                                            1

TTGTCAACAATAAAATTAGCAAAGTTAGTCCTTAATCTAGA
----.----+----.----+----.----+----.----+-.....3'    291
AACAGTTGTTATTTTAATCGTTTCAATCAGGAATTAGATCT v  n  n  k  i  s  k  v  s  p  .  s  r
```

TABLE 7

(SEQ ID NOS. 35 through 37)
PT-74 Sequence

```
ECR1

GAATTCGATGAGGCTTCTGGGATAGGCCCAGAAGTTCCTGATGACCGACTTCGAGCCCTCCCTAGGCCCAGTGTGCCCCTTCCGCTG TCAATGCCATC
5'...---------+---------+---------+---------+---------+---------+---------+---------+---------+---------+    100
     CTTAAGCTACTCCGAAGACCCTATCCGGGTCTTCAAGGACTACTGGCTGAAGCTCGGGAGGATCCGGGGAGGATCCGGGAAGGCGACGTTACGGTAG
      e  f  d  e  a  s  g  i  g  p  e  v  p  d  d  r  d  f  e  p  s  l  g  p  v  c  p  f  r  c  q  c  h  l

TTCGAGTGGTCCAGTGTTC TGATTTGGGT CTGACAAAGTGCCAAAAGGATCTTCCCCCT GACACAACTCTGCTAGACTCTGCAAAACAACAAATAACCGA
     ---------+---------+---------+---------+---------+---------+---------+---------+---------+---------+    200
     AAGCTCACCAGGTCACAACAGACTAAACCCAGACCTGTTC ACGTTTCT AGAAGGGGGATGTGTTGACACGATCTGAGACGTTTGTTG TTTATTGGCT
      r  v  v  q  c  s  d  l  g  l  d  k  v  p  k  d  l  p  p  d  t  t  l  l  d  l  q  n  n  k  i  t  e

AATCAAAGATGGAGACTTT AAGAACCTGAAGAACCTTCACGCATTGATT CTTGTCAACA ATAAAATTAGCAAAGTTAGTCCTGAGCATTTACACCTTTG
     ---------+---------+---------+---------+---------+---------+---------+---------+---------+---------+    300
     TTAGTTTCT ACCCTCGAAATTCTTGGACT TCTTGGAAGTGCCTAACTAAGAACAGTTGTTATTTTAATC GTTCAATCA GGACCTCGTAAATGTGAAAC
      i  k  d  g  d  f  k  n  l  k  n  l  h  a  l  i  l  v  n  n  k  i  s  k  v  s  p  g  a  f  t  p  l

GTGAAGTTGGAACGACTTT ATCTGTCCAA GAATCAGCTGAAGGAATTG CCAGAAAAAATGCCCAAAACTCTTCAGGAGCTGCGTGCCCATGAGAATGAGA
     ---------+---------+---------+---------+---------+---------+---------+---------+---------+---------+    400
     CACTTCAACCTTGCTGAAATAGACAGGTTCTTAGTCGACTTCTTAAGTCGAAGTTCTTAAGAAGTCCTCGACGACGGGTACTCTTACTCT
      v  k  l  e  r  r  l  y  l  s  k  n  q  l  k  e  l  p  e  k  m  p  k  t  l  q  e  l  r  a  h  e  n  e  i

TCACCAAAGTGCGAAAATAATCTAGA
     ---------+---------+......3'   426
     AGTGGTTTCACGCTTTTATTAGATCT
      t  k  v  r  k  .  s  r
                                              X
                                              B
                                              A
                                              1
```

TABLE 8

(SEQ ID NOS. 38 through 40)
PT-75 Sequence

```
E
C
R
1
         GAATTCGATGAGGCTTCGCGATAGGCCCAGAAGTTCCTGATGACCGGCGACTTCGAGCCTTCCCTAGGCCCCTTCCGGCTGTCAATGCCATC
5'...    ----+----+----+----+----+----+----+----+----+----+----+----+----+----+----+----+----+----+   100
         CTTAAGCTACTCCGAAGCGCTATCCGGGTCTTCAAGGACTACTGGCCGCTGAAGCTCGGAGGGATCCGGGGAAGGCGACGTTACGGTAG
          e  f  d  e  a  s  g  i  g  p  e  v  p  d  d  r  d  f  e  p  s  l  g  p  v  c  p  f  r  c  q  e  h  l

TTCCAGTGGTCCAGTGTTC TGATTTGGGT CTGGACAAAGTGCAAAAGTCTTCCCCT GACACAACTCTGCTAGACCTGCAAAACAACAAAATAACCGA
         ----+----+----+----+----+----+----+----+----+----+----+----+----+----+----+----+----+----+   200
         AAGGTCACCAGGTCACAAGACTAAACCCAGACTAAACCCAGACCTGTTTC AGAAGGGGACTGTGTTGAGACGATCTGGACGTTTGTG TTTTATTGGCT
          r  v  v  q  c  s  d  l  g  l  d  k  v  p  k  d  l  p  p  d  t  t  l  d  l  q  n  n  k  i  t  e

AATCAAAGATGGAGACTTT AAGAACCTGAAGAACCTTCACGCATTGATTCTTGTCACAATAAAATTAGCAAAGTTAGTCCTGGAGCATTTACACCTTTG
         ----+----+----+----+----+----+----+----+----+----+----+----+----+----+----+----+----+----+   300
         TTAGTTTCT ACCTCTGAAATTCTTGGACT TCTTGGAAGTGCGTAACTAAGAACAGTGTTATTTTAATC GTTTCAATCA GGACCTCGTAAATGTGAAAC
          i  k  d  g  d  f  k  n  l  k  n  l  h  a  l  i  l  v  n  n  k  i  s  k  v  s  p  g  a  f  t  p  l

GTGAAAGTTGGAAACGACTTT ATCTGTCCAAGAATCAGCTGAAGGAATTGCCCAAAAAATGCCCAAAACTCTTCAGGAGCTGCGTGCCATGAGAATGAGA
         ----+----+----+----+----+----+----+----+----+----+----+----+----+----+----+----+----+----+   400
         CACTTCAACCTTGCGAAATAGACAGGTTCTTAGTCGACTTCCTAAGCG GTCTTTTTA CGGGTTTTGA GAAGTCCTGACGCACGGTACTCTTACTCT
          v  k  l  e  r  l  y  l  s  k  n  q  l  k  e  l  p  e  e  k  m  p  k  t  l  q  e  l  r  a  h  e  n  e  i

TCACCAAAAGTGCGAAAAGTTACTTTCAAT GGACTGAACCAGATGATTGTCATAGAACTGGGCACCAATCCGCTGAAGAGTCAGGAATTGAAAATGGGGC
         ----+----+----+----+----+----+----+----+----+----+----+----+----+----+----+----+----+----+   500
         AGTGGTTTCACGCTTTTCA ATGAAAGTTACCTGACTTGGTCTACTAACAGTATCTTGAC CCGTGGTTAGGCGACTTCTCGAGTCGTTAACTTTTACCCCG
          t  k  v  r  k  v  t  f  n  g  l  n  q  m  i  v  i  e  l  g  t  n  p  l  k  s  s  g  i  e  n  g  a

X
                                                                                                     B
                                                                                                     A
                                                                                                     1

TTTTCCAGGG AATGAAGAAGCTCTCCTACA TCCGCATTGC TGATACCAATATCACCACCAGCTAATCTAGA
         ----+----+----+----+----+----+----+----+----+----+----+----+----+...3'   567
         AAAGGTCCCTTACTTCTTC GAGAGGATGTAGGCGTAACGACTATGGTTATAGTGGTCGATTAGATCT
          f  q  g  m  k  k  l  s  y  i  r  i  a  d  t  n  t  t  s  .  s  r
```

TABLE 9

(SEQ ID NOS. 41 through 43)
PT-76 Sequence

```
E
C
R
1
    GAATTCGATCAGGCTTCTGGGATAGGCCCAGAAGTTCCTGATGACCCGCGACTTCGAGCCCTCCCTAGGCCCAGTGTGCCCTTCCGCTG TCAATGCCATC
5'...---------+---------+---------+---------+---------+---------+---------+---------+---------+---------+ 100
    CTTAAGCTACTCCGAAGACCCTATCCGGGTCTTCAAGGACTACTGGGCGCTGAAGCTCGGGAGGGATCCGGTCACACGGGAAGGCGACGTTACGGTAG
     e f d e a s g i g p e v p d d r d f e p  s l g p v c p f r c  q c h l
```

```
    TTCGAGTGGTCCAGTGTTC TGATTTGGGT CTGGACAAAGTGCCAAAGGTC TCTAGACCT GACACAACTCTGCCCCT GACACAACTCTCCCCT GCAAAAACAAATAACCGA
    ---------+---------+---------+---------+---------+---------+---------+---------+---------+---------+ 200
    AAGCTCACCAGGTCACAAGACTAAACCCAGACCTGTTC ACGGTTTCCT AGAAGGGGACTGTGTTGAGACGATCTGACGTTTTGTTG TTTATTGGCT
     r v v q c s g d l g l d k v p k d  l p p d t t l d l  q n n k i t e
```

```
    AATCAAAGATGGAAGAACTTT AAGAACCTGAAGAACAACCTTCACGCATTGATT CTTGTCAACA AATAAAATTAGCAAAGTTAGTCCTGGAGCATTTACACCTTTG
    ---------+---------+---------+---------+---------+---------+---------+---------+---------+---------+ 300
    TTAGTTCT ACCTCTGAAATTCTTGACT TCTTGGAAGT GCGTAACTAACAGTTGTTATTTAAATC GTTCAATCA GGACCTCGTAAATGTGAAAC
     i k g d f k n l k n l h a l i  l v n n k i s k v s p g a f t p l
```

```
    GTGAAAGTTGGAACGACTTT ATCTGTCCAA GAATCAGCTGAAGGAATGGCCCAAAAAATGCCCAAAACTCTTCAGGAGCTGCGTGCCATGAGAATGAGA
    ---------+---------+---------+---------+---------+---------+---------+---------+---------+---------+ 400
    CACTTCAACCTTGCTGAAATAGACAGGTTCTTAGTCGAC TTCTTTA CGGGTTTTGAAGTCCTGACGCACGGGTACTCTTACTCT
     v k l e r f y l s k n q l k e l p e k m p k t  q e l r a h e n e i
```

```
    TCACCAAAGTGCGAAAAGTTACTTTCAAT GGACTGAACCAGATGATTGTCATAGAACTGGGCACCAATCCGCTGAAGAGCTCAGGAATTGAAAATGGGGC
    ---------+---------+---------+---------+---------+---------+---------+---------+---------+---------+ 500
    AGTGGTTTCACGCTTTTCAA ATGAAAGTTACCTGACTTGGTCTACTAACAGTATCTGACCGTGGTTAGGCGACTTCTCGAGTCGTTCTTAACTTTACCCCG
     t k v r k v t f n g l n q  m i v d e l g t n p l k s s g i e n g a
```

```
    TTTCCAGGG AATGAAGAAC ETCTCCTACA TCCGGCATTGC TGATACCATGTTGT AAGGAGTTCCAGAAGGAGGAGGAATGCCTTAATGTAGAA
    ---------+---------+---------+---------+---------+---------+---------+---------+---------+---------+ 600
    AAAGGTCCCTTACTTCTTC GAGAGGATGTAGCCGTAACGACTATGGTTA TAGTGGTCAT TCCCTTACG AATTACATCTT
     f q g m k k l s y i r i a  d t n i t s i p q g l p p s l t e  l h l
```

```
    GATGGCAACAAAATCAGCAGAGTTGATCAGCTAGCCTGAAAGGACTAGCCTGAATAATTTGGCTAAGGTGGGATTGAGTTTCA ACAGCATCTGCTGTTGACA
    ---------+---------+---------+---------+---------+---------+---------+---------+---------+---------+ 700
    CTACCGTTG TTTTAGTCGT CTCAACTACGTAGCGATCGGACTTTCCTGACT TATTAAACCCATTCAACCCTA ACTCAAAGTTGTCGTAGAGACGACAACTGT
     d g n k i s r v d a s l  k g l n n l s k l g l s f n s i s  a v d n
``` x

TABLE 9-continued (SEQ ID NOS. 41 through 43)
PT-76 Sequence

```
     B
     A
     1
ATTAATCTAGA
-----+----.3'  711
TAATTAGATCT
     s     r
```

TABLE 10

PT-77 Sequence (SEQ ID NOS. 44 through 46)

```
      GAATTCGATGAGGCTTCTGGGATAGGCCCAGAAGTTCCTGATGACCGCGACTTCGAGCCTCCCTAGGCCCAGTGTGCCCCTTCCGCTGTCAATGCCATC
      ----+----+----+----+----+----+----+----+----+----+----+----+----+----+----+----+----+----+----+----+   100
      CTTAAGCTACTCCGAAGACCCTATCCGGGTCTTCAAGGACTACTGGCGCTGAAGCTCGGAGGGATCCGGGTCACACGGGGAAGGCGACAGTTACGGTAG
       e  f  d  e  a  s  g  i  g  p  e  v  p  d  d  r  d  f  e  p  s  l  g  p  v  c  p  f  f  r  c  q  c  h  l

TTCGAGTGGTCCAGTGTCTCTGATTTGGGTCTGAACAAAGTGCCAAAGGATCTTCCCCCTGACACAACTCTGTCTAGACCTGCAAACAACAAAATAACCGA
      ----+----+----+----+----+----+----+----+----+----+----+----+----+----+----+----+----+----+----+----+   200
      AAGCTCACCAGGTCACAGAGACTAAACCCAGACTTGTTTCACGGTTTCCTAGAAGGGGACTGTGTTGAGACGATCTGGACGTTTTGTTGTTTTATTGGCT
       r  v  v  q  c  s  d  i  g  l  d  k  v  p  k  d  l  p  p  d  t  t  l  d  q  n  n  k  i  t  e

AATCAAAGATGGAGACTTTAAGAACCTTGACGCATTCTGTCAACAATAAAATTAGCAAAGTTAGTCCTGGAGCATTTACACCTTTG
      ----+----+----+----+----+----+----+----+----+----+----+----+----+----+----+----+----+----+----+----+   300
      TTAGTTTCTACCTCTGAAATTCTTGGACTTCTTGGAAGTGCGTAACTAAGAACAGTTGTTATTTTAATCATTCAGGACCTCGTAAATGTGGAAAC
       i  k  d  g  d  f  k  n  l  h  a  l  i  v  n  n  k  i  s  k  v  s  p  g  a  f  t  p  l

GTGAAGTTGGAACGACTTTATCTGTCCAAGAATCAGCTGAAGGAATTGCCAGAAAAAAATGCCCAAAACTCTTGAGGAGCTGCGTGCCATGAGAATGAGA
      ----+----+----+----+----+----+----+----+----+----+----+----+----+----+----+----+----+----+----+----+   400
      CACTTCAACCTTGCTGAAATAGACAGTTCTTAGTCGACTTCTTAACGGTCTTTTTTACGGGTTTTGAGAAGTCCTGACGCACGGTACTCTTACTCT
       v  k  l  e  r  r  l  y  l  s  k  n  q  l  k  e  l  p  e  k  m  p  k  t  l  q  e  l  r  a  h  e  n  e  i

TCACCAAAGTGCGAAAGTTACTTTCAATGGACTGAACCAGATGATTGTCATAGAACTGGGCACCAATCGCTGAAGAGCTCAGGAATTGAAAATGGGGC
      ----+----+----+----+----+----+----+----+----+----+----+----+----+----+----+----+----+----+----+----+   500
      AGTGGTTTCACGCTTTTCAATGAAAGTTACCTGACTTGGTCTACTAACAGTATCTTGACCCGTGGTTAGGCGACTTCTCGAGTCCTTAACTTTTACCCCG
       t  k  v  r  k  v  t  f  n  g  l  n  q  m  i  v  i  e  l  g  t  n  p  l  k  s  s  g  i  e  n  g

TTTCCAGGGAATGAAGAAGCTCTCCTACATCCGGCATTGCTGATACCAATATCACCAGGTCTCCCTCCTCAAGGTCTTCCTCCTTCCTTACGGAATTACATCTT
      ----+----+----+----+----+----+----+----+----+----+----+----+----+----+----+----+----+----+----+----+   600
      AAAGGTCCCTTACTTCTTCGAGAGGATGAAACGACTATGGCCGTAACGACTATGGTTATAGTGGTCGTAAGGAGTTCCAGAAGAGTTCCAGGAAGGAAGGAAGGACTTAATGTAGAA
       f  q  g  m  k  k  l  s  y  i  r  a  d  t  n  i  t  s  i  p  p  q  g  l  p  p  s  l  t  e  l  h  l

GATGGCAACAAAATCAGCAGAGTTGATGCAGCTAGCCTGAAAGGACTGAATAATTTGCTAAGTTGGGATTGAGTTTCAACAGCATCTCTGCTGTTGACA
      ----+----+----+----+----+----+----+----+----+----+----+----+----+----+----+----+----+----+----+----+   700
      CTACCGTTGTTTTAGTCGTCTCAACTACGTCGATCGGACTTTCCTGACTTTATGATTTAAACCGATTACTTAAACCGATTCAACCCTAACTCAAAGTTGTCGTAGAGACGACAACTGT
       d  g  n  k  i  s  r  v  d  a  a  s  l  k  g  l  n  n  l  k  l  g  l  s  f  n  s  i  s  a  v  d  n

ATGGCTCTCTGGCCAACACGCCTCATCTGAGGAGCTTCACTTGACAACAACAAGCTTACCAGAGTACCTGGTGGCTGGCTGGCAGAGCATAAGTACATCCA
      ----+----+----+----+----+----+----+----+----+----+----+----+----+----+----+----+----+----+----+----+   800
      TACCGAGAGACCGGTTGTGCGGAGTAGACTCCCTCGAAGTAGAACTGTTGTTGTTCGAATGGTCTCATGGACCACCGACCGTCCATGGACGCATTCATGTAGGT
       g  s  l  a  n  t  p  h  l  r  e  l  h  l  d  n  n  k  l  t  r  v  p  g  g  l  a  e  h  k  y  i  q
```

5'
E
C
R
1

TABLE 10-continued

PT-77 Sequence (SEQ ID NOS. 44 through 46)

```
                                                    X
                                                    B
                                                    A
                                                    1
GGTTGTCTACCTTCATAACAACAATATCTCTCTGTAGTTGGATAATCTAGA
----+----.----+----.----+----.----+----.----+----.----3'   849
CCAACAGATGGAAGTATTGTTGTTATAGAGACATCAACCTATTAGATCT
 v  v  y  l  h  n  n  n  i  s  v  v  g  .  s  r
```

TABLE 11

(SEQ ID Nos. 47 through 49)
PT-78 Sequence

```
        GAATTCGATGAGGCTTCTGGGATAGGCCGACTTCGAGTTCCTGATGACCGCGACTTCGAGCCCTCCTAGGCCGACTTCGAGCCCTCCTAGGCCGACTTCGAGCCCTCCTAGGCCGACTTCGAGCCCTCC   100
5' ... CTTAAGCTACTCCGAAGACCCTATCCGGTCTTCAAGGACTACTGGCCTGAAGCTCGGAGGGATCCGGGTCACACGGGAAGGCGACAGTTACGGTAG
        e  f  d  e  a  s  g  i  g  p  e  v  p  d  d  r  d  f  e  p  s  l  g  p  v  c  p  f  r  c  q  c  h  l

TTCGAGTGGTCCAGTGTTCTGATTTGGGTCTGACAAAGTGCCAAAAGGATCTCCCCCTGACACAACTCTGCTAGAACTCTGCAAAACAACAAATAACCGA   200
        AAGCTCACCAGGTCACAAGACTAAACCCAGACTGTTTCACGGTTCCTAGAGGGGGACTGTGTTGAGACGATCTGAGACGTTTGTTGTTTATTGGCT
        r  v  v  q  c  s  d  l  g  l  d  k  v  p  k  d  l  p  p  d  t  t  i  d  l  q  n  n  k  i  t  e

AATCAAAGATGGAGACTTTAAGAACCTTGAAGAATTCTTGTCACGCATTGATTCTTGTCAACAATAAATTAGCAAAGTTAGTCCTGGAGCATTACACCTTTG   300
        TTAGTTTCTACCTCTGAAATTCTTGGAACTTCTTAAGAACTTCTTAAGAACAGTTGTTATTTAATCGTTTAATCGTTCAATCAGGACCTCGTAAATGTGAAAC
        i  k  d  g  d  f  k  n  l  h  a  l  i  l  v  n  n  k  i  s  k  v  s  p  g  a  f  t  p  l

GTGAAGTTGGAACGACTTTATCTGTCCAAGAATCAGCTGAAGGAATTGCCAGAAAAAAATGCCCAAAACTCTTCAGGAGCTGCGTGCCATGAGAATGAGA   400
        CACTTCAACCTTGCTGAAATAGACAGGTTCTTAGTCGACTTCCTTAACGGTCTTTTTACGGGTTTTTGAAAGTCCTCGACGCACGGTACTCTTACTCT
        v  k  l  e  r  l  y  l  s  k  n  q  l  k  e  l  p  e  k  m  p  k  t  l  q  e  l  r  a  h  e  n  e  i

TGACCAAAGTGCGAAAAGTTACTTTCAATGGACTGGCCACCAATGATGTCATAGAACTGGCACATGATGTTGACCCGTGGTTAGGCGACTTCTGAGTCTAAGAGAGACTCTAACTTTTACCCCG   500
        ACTGGTTTCACGCTTTTCAATGAAAGTTACCTGACCGGTGGTTACTACAGTATGTTGACCGTGGTTAGGCGACTTCTGAGTCTAAGAGTTCCTAACTTTTACCCCG
        t  k  v  r  k  v  t  f  n  g  l  n  q  m  i  v  i  e  l  g  t  n  p  l  k  s  s  g  i  e  n  g  a

TTTCCAGGGAATGAAGAAGCTCTCGAGAGGATGATGTAGGCGTAACGACGTAACGACGTTATGTGGTCGTAAGGAGTTCCAGAAGGAGGAGGAAATGCCTTAATGCTTAGAA   600
        AAAGGTCCCTTACTTCTTCGAGAGCTCTCCTACTACATCACGATTGCTGCAATTACGATTACGAAGTGGAATTACCAAGGTCTCCTCCTCCTCCTTACGGAATTACATCTT
        f  q  g  m  k  k  l  s  y  i  r  i  a  d  t  n  i  t  s  i  p  q  g  l  p  p  s  l  t  e  l  h  l

GATGGCAACAAAATCAGCAGAGTTGATGCAGCTAGCCTGAAAGGACTGAAATAATTGGCTAAGTTGGATTGAGTTCAACAGCATCTCTGCTGTTGACA   700
        CTACCGTTGTTTTAGTCGTCTCAACTACGTCGATCGGACTTCCTGACTTATTAAACCGATTCAACCTAACTCAAGTTGTCGTAGAGACGACAACTGT
        d  g  n  k  i  s  r  v  d  a  a  s  l  k  g  l  n  n  l  a  k  l  g  l  s  f  n  i  s  a  v  d  n

ATGGCTCTCTGGCCAACACGCCTCATCTGAGGGAGCTTCACTTGGACAACAACAAGCTTACCAGAGTACCTGGTGGGCTGCAGACATAAGTACATCCA   800
        TACCGAGAgACCGGTTGTGCGGAGTAGACTCCCTCGAAGTGAACCTGTTGTTGTTCGAATGGTCTCATGGACACCTTACAACACATAAGTACATCCA
        t  a  c  c  g  a  g  a  c  c  g  g  t  t  g  t  g  c  g  g  a  g  t  a  g  a  c  t  c  c  c  t
        g  s  l  a  n  t  p  h  l  r  e  l  h  l  d  n  n  k  l  t  r  v  p  g  g  l  a  e  h  k  y  i  q

GGTTGTCTACCTTCATAACACAATATCTCGTAGTTGGATCAAGTGACTTCTGCCACCTGACACAACAACAACCAAAAGGTTCTTATTCGGGTGTGAGT   900
        CCAACAGATGGAAGTATTGTGTTATAGAGACATCAACCTAGTTCACTGAAGACGGGTGACCTGTGTTGTGGTTTTCCAAGAATAAGCCACACTCA
        v  v  y  l  h  n  n  i  s  v  v  g  s  s  d  f  c  p  p  g  g  h  n  t  k  k  a  s  y  s  g  v  s
```

TABLE 11-continued (SEQ ID Nos. 47 through 49)
PT-78 Sequence

```
              X
              B
              A
              1
CTTTTCAGCAACCCGTAATCTAGA
-----.----+----.----+----...3' 924
GAAAAGTCGTTGGGCATTAGATCT
    l  f  s  n  p  .  s  r
```

TABLE 12

(SEQ ID Nos. 50 through 52)
PT-84 Sequence

```
  E
  C
  R
  1
     GAATTCGATGAGGCTTCTGGGATAGGCCCAGAAGTTCCTGATGACCGCG
5'...----.----+----.----+----.----+----.----+----.----
     CTTAAGCTAATCCGAAGACCCTATCCGGGTCTTCAAGGACTACTGGCGC
      e  f  d  e  a  s  g  i  g  p  e  v  p  d  d  r  d

ACTTCGAGCCCTCCCTAGGCCCAGTGTCCCCCTTCCGCTCTCAATCCCATC
+----.----+----.----+----.----+----.----+----.----+ 100
TGAAGCTCGGGAGGGATCCGGGTCACAGGGGGAAGGCGAGAGTTAGGGTAG
 f  e  p  s  l  g  p  v  s  p  f  r  s  q  s  h  l

X
                                          B
                                          A
                                          1
TTCGAGTGGTCCAGTCTTCTGATTTGGGTCTGGACTAATCTAGA
----.----+----.----+----.----+----.----+----...3' 144
AAGCTCACCAGGTCAGAAGACTAAACCCAGACCTGATTAGATCT
  r  v  v  q  s  s  d  l  g  l  d  .  s  r
```

TABLE 13

(SEQ ID Nos. 53 through 55)
PT-85 Sequence

```
  E
  C
  R
  1
     GAATTCGATGAGGCTTCTGGGATAGGCCCAGAAGTTCCTGATGACCGCG
5'...----.----+----.----+----.----+----.----+----.----
     CTTAAGCTAATCCGAAGACCCTATCCGGGTCTTCAAGGACTACTGGCGC
      e  f  d  e  a  s  g  i  g  p  e  v  p  d  d  r  d

ACTTCGAGCCCTCCCTAGGCCCAGTGTGCCCCTTCCGCTCTCAATCCCATC
+----.----+----.----+----.----+----.----+----.----+ 100
TGAAGCTCGGGAGGGATCCGGGTCACACGGGGAAGGCGAGAGTTAGGGTAG
 f  e  p  s  l  g  p  v  c  p  f  r  s  q  s  h  l

X
                                          B
                                          A
                                          1
TTCGAGTGGTCCAGTGTTCTGATTTGGGTCTGGACTAATCTAGA
----.----+----.----+----.----+----.----+----...3' 144
AAGCTCACCAGGTCACAAGACTAAACCCAGACCTGATTAGATCT
  r  v  v  q  c  s  d  l  g  l  d  .  s  r
```

TABLE 14

(SEQ ID Nos. 56 through 58)
PT-86 Sequence

```
E
C
R
1
      GAATTCTCAAGTGACTTCTGCCCACCTGGACACAACACCAAAAAGGCTT
5'...----.----+----.----+----.----+----.----+----.----
      CTTAAGAGTTCACTGAAGACGGGTGGACCGTGTTGTGG TTTTTCCGAA
       e  f  s  s  d  f  c  p  p  g  h  n  t  k  k  a  s

CTTATTCGGGTGTGAGTCTTTTCAGCAACCCGGTCCAGTACTGGGAGATAC
+----.----+----.----+----.----+----.----+----.----+  100
GAATAAGCCCACACTCAGAAAAGTCGTTGGGCCAGGTCATGACCCTCTATG
 y  s  g  v  s  l  f  s  n  p  v  q  y  w  e  i  q

X
                                                  B
                                                  A
                                                  1
AGCCATCCACCTTCAGATGTGTCTACGTCCGCTCTGCCATTCAACTCGGAAACTATAAGTAATCTAGA
----.----+----.----+----.----+----.----+----.----+----.----+----.----...3' 168
TCGGTAGGTGGAAGTCTACACAGATGCACGCGAGACGGTAAGTTGAGCCTTTGATATTCATTAGATCT
  p  s  t  f  r  c  v  y  v  r  s  a  i  q  l  g  n  y  k  .  s  r
```

TABLE 15

(SEQ ID Nos. 59 through 61)
PT-87 Sequence

```
E
C
R
1
      GAATTCTCAAGTGACTTCTCCCCACCTGGACACAACACCAAAAAGGCTT
5'...----.----+----.----+----.----+----.----+----.----
      CTTAAGAGTTCACTGAAGAGGGGTGGACCGTGTTGTGG TTTTTCCGAA
       e  f  s  s  d  f  s  p  p  g  h  n  t  k  k  a  s

CTTATTCGGGTGTGAGTCTTTTCAGCAACCCGGTCCAGTACTGGGAGATAC
+----.----+----.----+----.----+----.----+----.----+  100
GAATAAGCCCACACTCAGAAAAGTCGTTGGGCCAGGTCATGACCCTCTATG
 y  s  g  v  s  l  f  s  n  p  v  q  y  w  e  i  q

X
                                                  B
                                                  A
                                                  1
AGCCATCCACCTTCAGATGTGTCTACGTCCGCTCTGCCATTCAACTCGGAAACTATAAGTAATCTAGA
----.----+----.----+----.----+----.----+----.----+----.----+----.----...3' 168
TCGGTAGGTGGAAGTCTACACAGATGCACGCGAGACGGTAAGTTGAGCCTTTGATATTCATTAGATCT
  p  s  t  f  r  c  v  y  v  r  s  a  i  q  l  g  n  y  k  .  s  r
```

EXAMPLE VI

BINDING STUDIES OF $^{125}$I-TGF-$\beta$ TO IMMOBILIZED DECORIN AND FRAGMENTS Immulon wells were coated with 0.5 µg/ml recombinant decorin at 50 µl/well. The wells were placed in a 37° C. incubator overnight and thereafter washed 3 times with 200 µl PBS (0.15M NaCl) per well to remove unbound decorin. TGF-$\beta$ labeled with $^{125}$I (400 pM, New England Nuclear, Bolton-Hunter Labeled) was pre-incubated with or without competitors in 200 µl PBS/0.05% Tween-20 for 1 hour and 45 minutes at room temperature. Competitors included recombinant human decorin preparations (DC-13 and DC-18v), decorin fragments, and MBP as a negative control. DC-13 and DC-18v are different preparations of recombinant human decorin; PT-71 or MBP (maltose-binding protein) is a negative control; PT-65 is MBP-whole decorin; PT-72 is MBP-decorin N-terminus; PT-73 is PT-72 +2 LRR; PT-84 and PT-85 are cysteine to serine mutant of PT-72; PT-86 is decorin C terminus; PT-87 is cysteine to serine mutant of PT-86.

Fifty µl/well of the pre-incubated $^{125}$I-TGF-$\beta$ mixture or control were added and incubated overnight at 0° C. Following the incubation, 50 µl of the free TGF-$\beta$ supernatants were transferred to labeled tubes. The plate was washed 3 times with 0.05% Tween-20 in PBS (200 µl/well). The wells were then transferred into tubes for counting in a gamma counter. The results of the binding studies with immobilized decorin are summarized in FIGS. 7 and 8.

Figure 7:
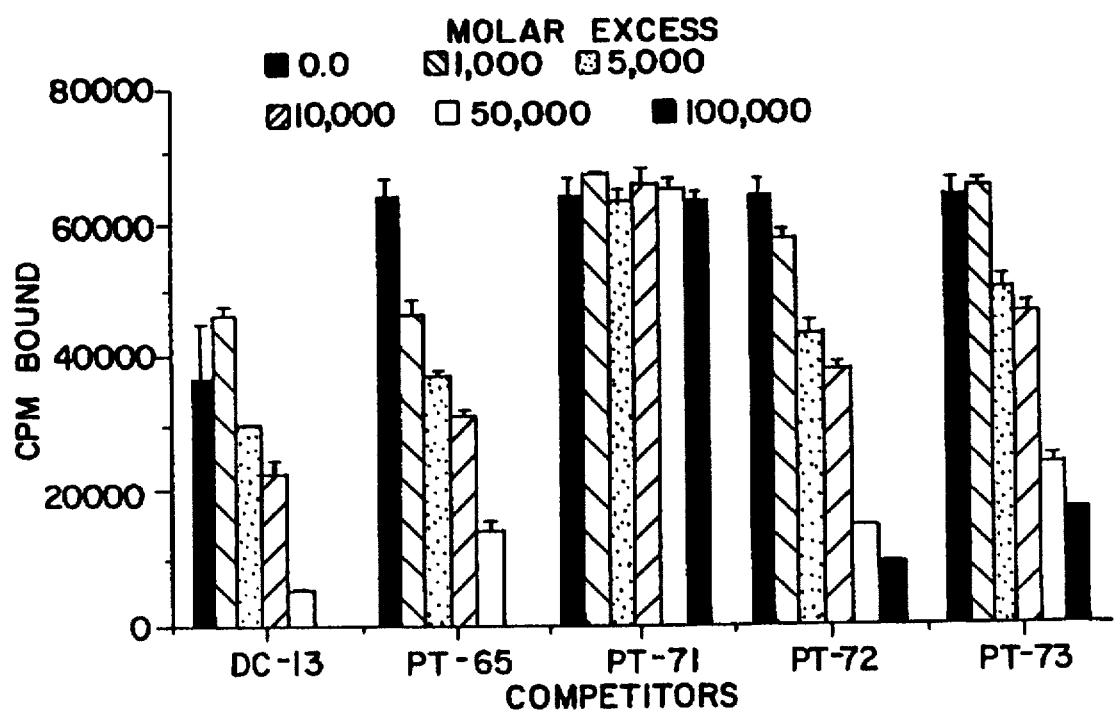
FIG. 7 shows the results of binding studies of $^{125}$I-TGFβ to immobilized recombinant decorin (DC13) and MBP-decorin fragments PT-65, PT-71, PT-72 and PT-73.

Recombinant human decorin (DC-13), MBP-whole decorin (PT-65), MBP-decorin N-terminus (PT-72) and MBP-decorin N-terminus+2 leucine rich repeats (PT-73) inhibited $^{125}$I-TGF-β binding to immobilized decorin as shown in FIG. 7. MBP alone (PT-71) had no effect on $^{125}$I-TGF-β binding to immobilized decorin. These results demonstrate that the N-terminus of decorin is capable of binding TGF-β in solution and preventing it from binding to immobilized decorin. Thus, two portions of the molecule appear to contain part of the binding site in decorin for TGF-β.

Figure 8:
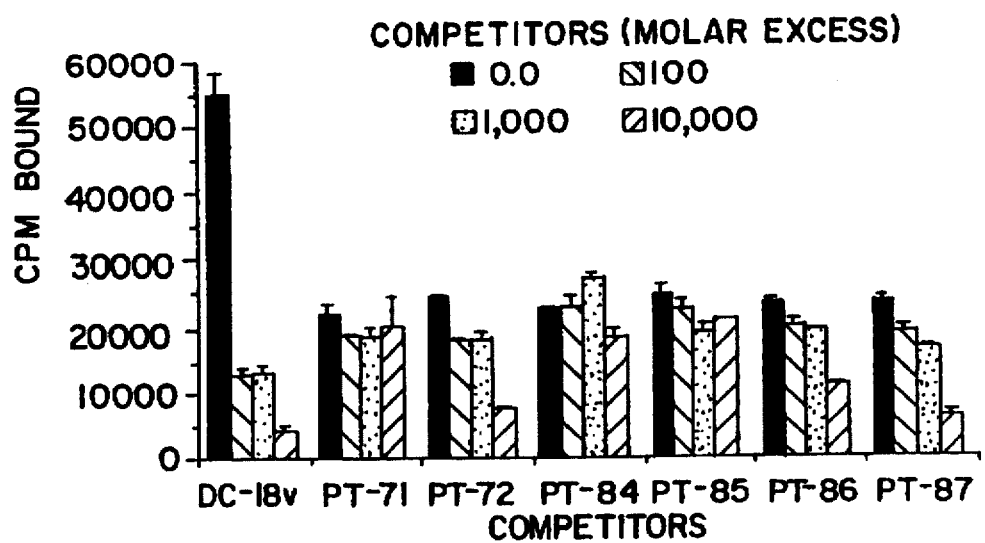
FIG. 8 shows the results of binding studies of $^{125}$I-TGFβ to immobilized decorin (DC-18v) and MBP-decorin fragments PT-71, PT-72, PT-84, PT-85, PT-86 and PT-87.

As shown in FIG. 8, recombinant human decorin (DC-18V)+MBP-decorin N-terminus (PT-72) inhibited $^{125}$I-TGF-β binding to immobilized decorin. In addition, cysteine to serine mutants of PT-72, (C-24, C-28, C-30, C-37 to serine, PT-84; C-28 and C-30 to serine, PT-85) did not inhibit $^{125}$I-TGF-β binding to decorin. MBP-decorin C-terminus (PT-86) and a cysteine to serine mutant (PT-87) of PT-86 also inhibited $^{125}$I-TGF-β binding to decorin. These results demonstrate that the C-terminus of decorin is also capable of binding TGF-β and that the first cysteine residue in the C-terminus is not required for TGF-β binding.

EXAMPLE VII

BINDING OF $^{125}$I-TGF-β TO HEPG2 CELLS

Figure 9:
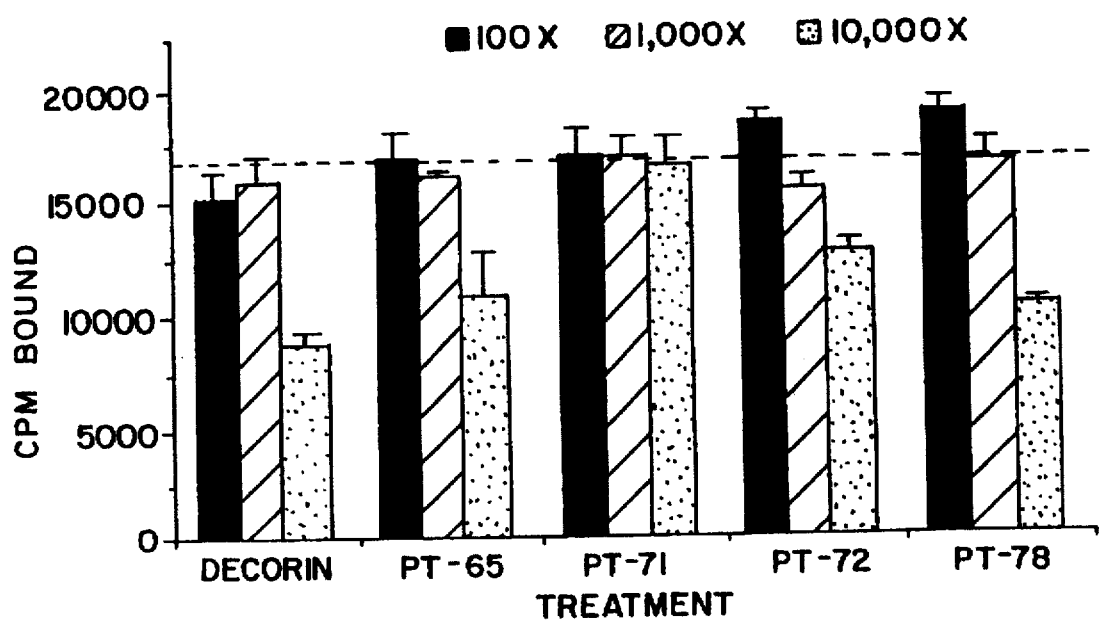
FIG. 9 shows the results of binding studies of $^{125}$I-TGFβ1 to HepG2 cells in the presence of decorin fragments PT-65, PT-71, PT-72 and PT-78.

About $2.5 \times 10^4$ HepG2 cells or L-M(tk-) cells were incubated with 250 pM[$^{125}$I]TGF-β in the presence of recombinant human decorin (DC-12), PT-71 (MBP), decorin fragments (PT-72, -73, -84, -85, -86 and -87) or anti-TGF-β antibodies for 2 hours at room temperature. Cells were washed with washing buffer (128 mM NaCl, 5 mM KCl, 5 mM Mg$_2$SO$_4$, 1.2 mM CaCl$_2$, 50 mM HEPES, pH 7.5) four times before determination of bound CPM. The results are summarized in FIGS. 9, 10 and 11.

Recombinant human decorin, MBP-whole decorin (PT-65), MBP-decorin N-terminus (PT-72) and MBP-decorin N-terminus +2 leucine rich repeats (PT-78) inhibited $^{125}$I-TGF-β binding to HepG2 cells. MBP alone (PT-71) had no effect on $^{125}$I-TGF-β binding to HepG2. These results shown in FIG. 9 demonstrate that the N-terminus of decorin is capable of preventing TGF-β from binding to its receptor on HepG2 cells.

Figure 10:
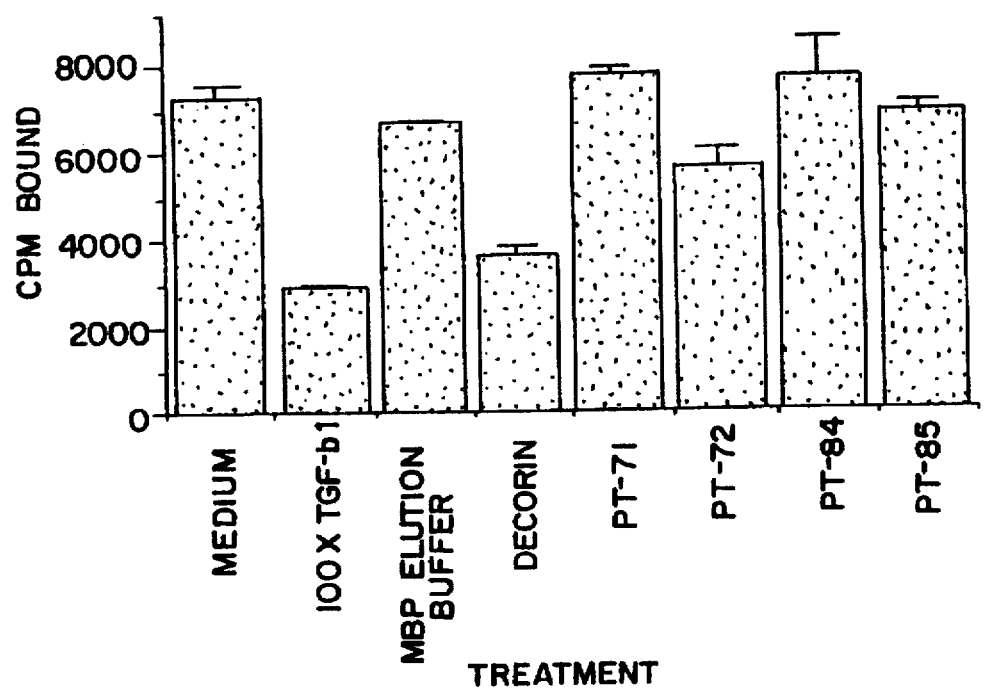
FIG. 10 shows the results of binding studies of $^{125}$I-TGFβ to L-M(tk-) cells in the presence of decorin and decorin fragments PT-71, PT-72, PT-84 and PT-85.

As shown in FIG. 10, recombinant human decorin and MBP-decorin N-terminus (PT-72) inhibited $^{125}$I-TGF-β binding to L-M(tk-) cells. An anti-TGF-β1 antibody also inhibited TGF-β binding to these cells. Cysteine to serine mutants of PT-72 (C-24, C-28, C-30, C-37 to serine, PT-84; C-28 and C-30 to serine, PT-85) did not inhibit $^{125}$I-TGF-β binding to L-M(tk-) cells.

Figure 11:
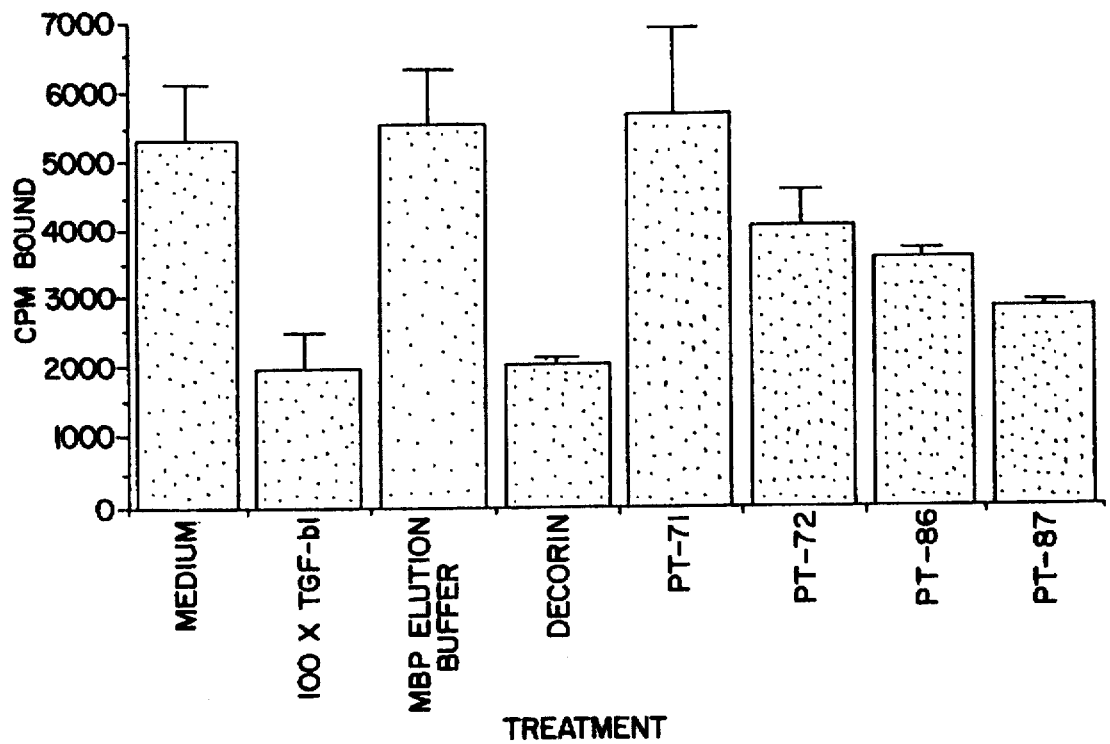
FIG. 11 shows the results of binding studies of $^{125}$I-TGFβ1 to L-M(tk-) cells in the presence of decorin and recombinant decorin fragments PT-71, PT-72, PT-86 and PT-87.

Recombinant human decorin, MBP-decorin N-terminus (PT-72) and anti-TGF-β antibodies inhibited $^{125}$I-TGF-β binding to L-M(tk-) cells. MBP-decorin C-terminus (PT-86) and a cysteine to serine mutant (PT-87) of PT-86 also inhibited $^{125}$I-TGF-β binding to L-M(tk-) cells. As shown in FIG. 11, these results demonstrate that the C-terminus of decorin also is capable of inhibiting TGF-β binding to its receptor, and that the first cysteine residue of the C-terminus is not required for inhibition.

EXAMPLE VIII

SYNTHETIC PEPTIDES

The following peptides were synthesized and tested for their ability to inhibit binding of TGFβ1 to L-M(tk-) cells:

TABLE 16

| Name | Sequence |
|---|---|
| $H_{31}$—$S_{37}$ | HLRVVQS (SEQ ID NO. 17) |
| $P_{25}$—$Q_{36}$ | PFRSQSHLRVVQ (SEQ ID NO. 18) |
| $H_{31}$—$L_{42}$ | HLRVVQSSDLGL (SEQ ID NO. 19) |
| $nP_{25}$—$Q_{36}$ | PFRCQCHLRVVQ (SEQ ID NO. 20) |

Peptide $H_{31}$-$S_{37}$ corresponds to the same decorin sequence between His-31 and Cys-37 except the Cysteine at position 37 is replaced with a serine. Peptide $P_{25}$-$Q_{36}$ corresponds to the sequence reported in Krusius and Ruoslahti, supra, from position Pro-25 through Gln-36, except the native Cysteine residues at positions 28 and 30 are each replaced with a serine. Peptide $H_{31}$ - $L_{42}$ also corresponds to decorin between His-31 and Leu-42 except the cysteine at position 37 is replaced with a serine. Peptide $nP_{25}$-$Q_{36}$ corresponds exactly with decorin from position Pro-25 through Gln-36.

The peptides were synthesized using the applied Biosystems, Inc. Model 430A or 431A automatic peptide synthesizer and the chemistry provided by the manufacturer.

The activity of the peptides was evaluated using the L-M(tk-) TGFβ1 binding inhibition assay described in Example VII, except various concentrations of peptide were incubated with the cells and TGFβ1 instead of decorin and recombinant decorin fragments. The negative control was a synthetic peptide corresponding to the first 15 amino acids of decorin, which has the sequence DEASGIGPEVPDDRD (SEQ ID NO. 21).

Figure 12:
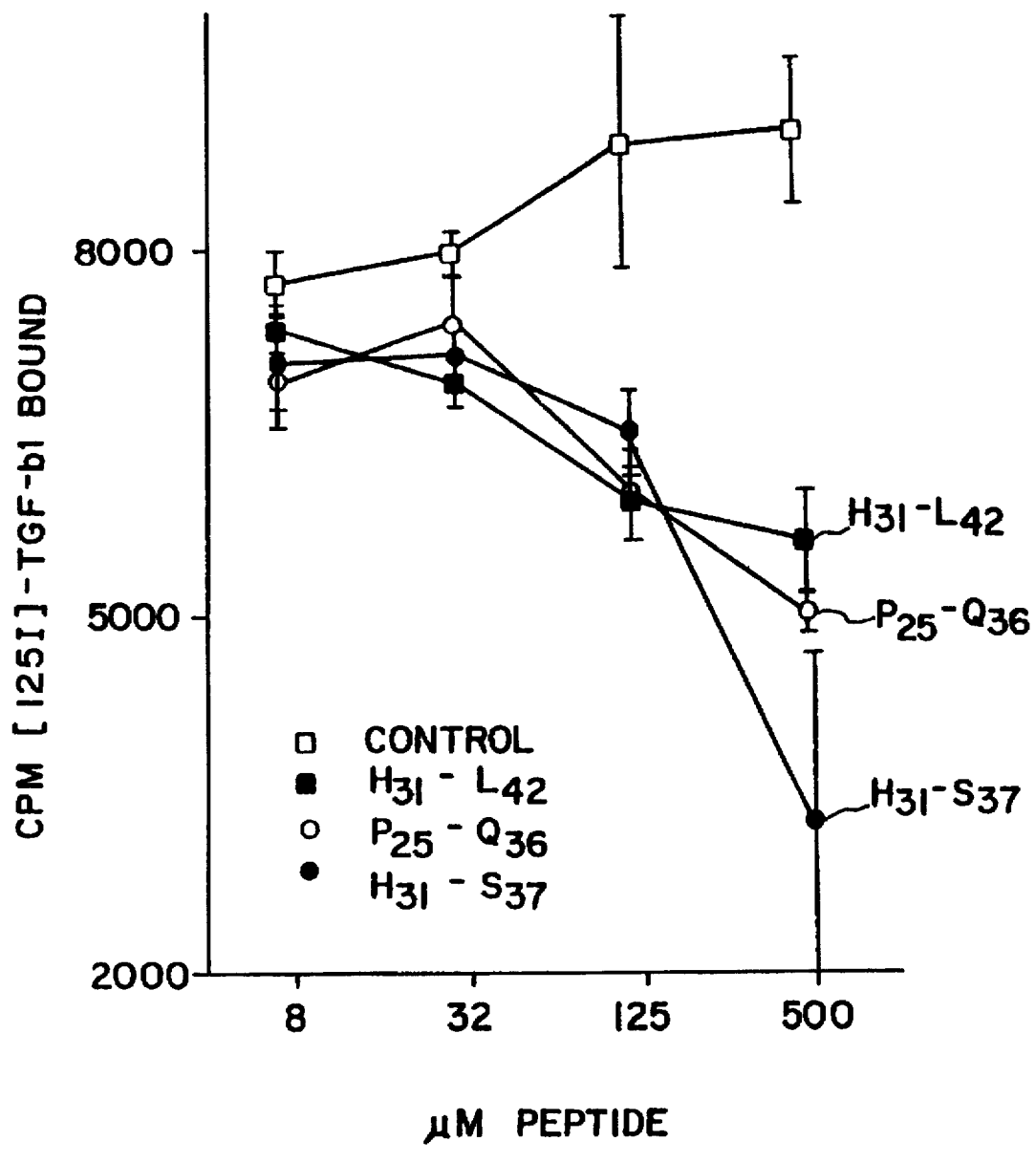
FIG. 12 shows the results of binding studies of $^{125}$I-TGFβ1 to L-M(tk-) cells in the presence of synthetic decorin peptide fragments $P_{25}$-$Q_{36}$, $H_{31}$-$S_{37}$ and $H_{31}$-$L_{42}$ and a control peptide corresponding to the N-terminal 15-mer.

FIG. 12 provides the binding data for peptides $P_{25}$-$Q_{36}$, $H_{31}$-$S_{37}$, and $H_{31}$-$L_{42}$ and the control peptide. All three test peptides inhibited binding of TGFβ1 to L-M(tk-) cells. Peptide $nP_{25}$-$Q_{36}$, in which the native Cys residues remain, also demonstrated inhibitory activity, albeit to a lesser extent. Table 16 lists the test peptides in the order of decreasing inhibitory activity, i.e., peptide $H_{31}$-$S_{37}$ was found to show the highest inhibitory activity.

Further binding studies were conducted with soluble N-terminal decorin peptide fragments synthesized and tested for their ability to inhibit TGF-β1 binding to immobilized decorin as described above. The N-terminal peptide fragments are listed in Table 17.

TABLE 17

| Peptide | Sequence |
|---|---|
| 16D | VPDDRDFEPSLG (SEQ ID NO. 22) |
| 16E | FEPSLGPVCPFR (SEQ ID NO. 23) |
| 16G | HLRVVQCSDLGL (SEQ ID NO. 24) |
| 16H | CSDLGLDKVPKDLPPD (SEQ ID NO. 25) |

Figure 13:
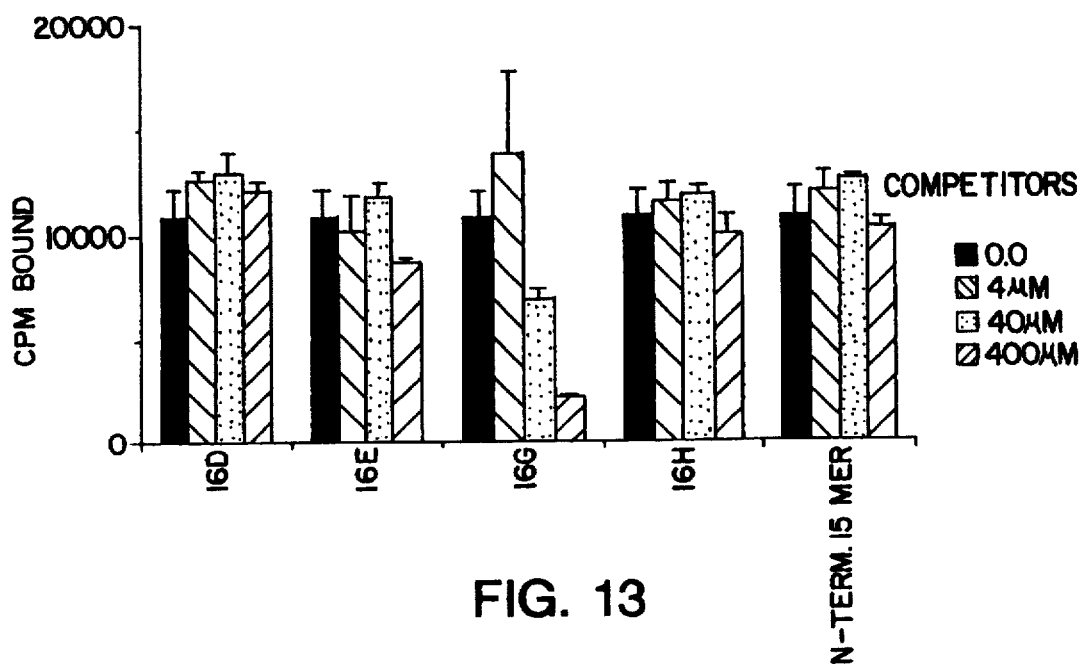
FIG. 13 shows the results of $^{125}$I-TGFβ binding to immobilized decorin with or without the presence of synthetic decorin peptide fragments 16D, 16E, 16G and 16H as well as a control peptide corresponding to the N-terminal 15-mer.

The results of the binding studies are shown in FIG. 13, which shows that the peptide 16G inhibited TGF-β binding to immobilized decorin.

Although the invention has been described with reference to the presently-preferred embodiments, it should be understood that various modifications can be made without departing from the spirit of the invention. Accordingly, the invention is limited only by the following claims.

We claim:

1. A polypeptide comprising the sequence His-Leu-Arg-Val-Val-Gln (SEQ ID NO: 62), wherein the polypeptide is between 6 and 95 amino acids in length.

2. The polypeptide of claim 1 selected from the group consisting of PT 72 (SEQ ID NO: 31), PT 73 (SEQ ID NO: 34), $P_{25}$-$Q_{36}$(SEQ ID NO: 18), $H_{31}$-$S_{37}$(SEQ ID NO: 17), $H_{31}$-$L_{42}$(SEQ ID NO: 19), and 16G (SEQ ID NO: 24).

3. The polypeptide of claim 1 having the sequence His-Leu-Arg-Val-Val-Gln-Cys-Ser-Asp-Leu-Gly-Leu (SEQ ID NO: 24).

4. A polypeptide whose amino acid sequence is: Ser-Ser-Asp-Phe-Cys-Pro-Pro-Gly-His-Asn-Thr-Lys-Lys-Ala-Ser-Tyr-Ser-Gly-Val-Ser-Leu-Phe-Ser-Asn-Pro-Val-Gln-Tyr-Trp-Glu-Ile-Gln-Pro-Ser-Thr-Phe-Arg-Cys-Val-Tyr-Val-Arg-Ser-Ala-Ile-Gln-Leu-Gly-Asn-Tyr-Lys (SEQ ID NO: 57, residues 3 to 53).

5. A polypeptide whose amino acid sequence is: Ser-Ser-Asp-Phe-Ser-Pro-Pro-Gly-His-Asn-Thr-Lys-Lys-Ala-Ser-Tyr-Ser-Gly-Val-Ser-Leu-Phe-Ser-Asn-Pro-Val-Gln-Tyr-Trp-Glu-Ile-Gln-Pro-Ser-Thr-Phe-Arg-Cys-Val-Tyr-Val-Arg-Ser-Ala-Ile-Gln-Leu-Gly-Asn-Tyr-Lys (SEQ ID NO: 60, residues 3 to 53).

* * * * *

UNITED STATES PATENT AND TRADEMARK OFFICE
CERTIFICATE OF CORRECTION

PATENT NO. : 5,705,609
DATED : Jan. 6, 1998
INVENTOR(S) : Ruoslahti et al.

It is certified that error appears in the above-identified patent and that said Letters Patent is hereby corrected as shown below:

Column 1, line 10, please delete "1988." and replace therefor with --1988, now abandoned.--

Column 2, line 66, please delete "(○)" and replace therefor with --(●)--.

Column 2, line 67, please delete "(●)" and replace therefor with --(○)--.

Column 3, line 18, please delete "(■)" and replace therefor with --(▲)--.

Column 3, line 30, please delete "(○)" and replace therefor with --(●)--.

Column 3, line 30, please delete "(●)" and replace therefor with --(○)--.

Column 4, line 2, please delete "(○)" and replace therefor with --(●)--.

Column 4, line 2, please delete "(●)" and replace therefor with --(○)--.

Column 7, line 49, please delete "CaCland" and replace therefor with --$CaCl_2$ and--.

UNITED STATES PATENT AND TRADEMARK OFFICE
CERTIFICATE OF CORRECTION

PATENT NO. : 5,705,609
DATED : Jan. 6, 1998
INVENTOR(S) : Ruoslahti et al.

It is certified that error appears in the above-identified patent and that said Letters Patent is hereby corrected as shown below:

Column 15, line 65, please delete "DH5β" and replace therefor with --DH5α--

Column 16, line 2, please delete "DH5β" and replace therefor with --DH5α--.

Column 16, line 31, please delete "amylose" and replace therefor with --amylase--.

In Claim 2, column 97, line 36, please delete "(SEQ ID NO:31)" and replace therefor with --(SEQ ID NO:29)--.

In Claim 2, column 97, line 37, please delete "(SEQ ID NO:34)" and replace therefor with --(SEQ ID NO:32)--.

UNITED STATES PATENT AND TRADEMARK OFFICE
CERTIFICATE OF CORRECTION

PATENT NO. : 5,705,609
DATED : Jan. 6, 1998
INVENTOR(S) : Ruoslahti et al.

It is certified that error appears in the above-identified patent and that said Letters Patent is hereby corrected as shown below:

Column 9, line 12, please delete "(FIG. 1 and B)" and replace therefor with --(FIG 1B)--.

Column 10, line 5, please insert --gel-- before "electrophoresis".

Column 10, line 25, please delete "(○)" and replace therefor with --(●)--.

Column 10, line 25, please delete "(●)" and replace therefor with --(○)--.

UNITED STATES PATENT AND TRADEMARK OFFICE
CERTIFICATE OF CORRECTION

PATENT NO. : 5,705,609
DATED : January 6, 1998
INVENTOR(S) : Ruoslahti et al.

It is certified that error appears in the above-identified patent and that said Letters Patent is hereby corrected as shown below:

Column 12, line 9, please delete "shown" and replace therefor with --show--.

Column 12, line 27, please delete "e-MEM" and replace therefor with --α-MEM--.

Column 13, line 17, please delete "guanidine- HCl" and replace therefor with --guanidine-HCl--.

Column 15, line 40, please delete "DH5β" and replace therefor with --DH5α--

Signed and Sealed this

Twentieth Day of July, 1999

*Attest:*

Q. TODD DICKINSON

*Attesting Officer*      *Acting Commissioner of Patents and Trademarks*